United States Patent [19]
Murai et al.

[11] Patent Number: 5,190,959
[45] Date of Patent: Mar. 2, 1993

[54] PIPERIDINE COMPOUNDS WHICH HAVE USEFUL PHARMACEUTICAL ACTIVITY

[75] Inventors: Satoshi Murai; Masanao Shimano; Hiroshi Yamamoto; Toshihiro Koyama; Tsutomu Nakamura; Masaru Ogawa; Mitsuru Watanuki; Taira Okamoto; Toshimitsu Hori, all of Kyoto, Japan

[73] Assignee: Kaken Pharmaceutical Co. Ltd., Tokyo, Japan

[21] Appl. No.: 925,017

[22] Filed: Aug. 5, 1992

[30] Foreign Application Priority Data

Aug. 8, 1991 [JP] Japan .................................. 3-199649
Apr. 16, 1992 [JP] Japan .................................. 4-96418

[51] Int. Cl.$^5$ .......................................... A61K 31/445
[52] U.S. Cl. ...................................... 514/318; 514/326; 514/327; 546/194; 546/213; 546/242
[58] Field of Search ...................... 546/194, 213, 242; 514/318, 326, 327

[56] References Cited

U.S. PATENT DOCUMENTS 4,942,238 7/1990 Rytz et al. .......................... 546/242

*Primary Examiner*—Alan L. Rotman
*Assistant Examiner*—Zinna N. Davis
*Attorney, Agent, or Firm*—Armstrong, Westerman, Hattori, McLeland & Naughton

[57] ABSTRACT

A piperidine derivative having the formula (I):

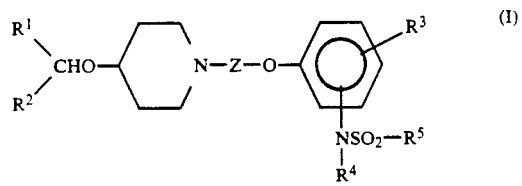

wherein $R^1$ and $R^2$, which may be the same or different from each other, are (i) a not-substituted phenyl group or a phenyl group substituted by a halogen atom, trifluoromethyl group, a $C_{1-5}$ alkyl group or a $C_{1-5}$ alkoxyl group, (ii) a $C_{3-7}$ cycloalkyl group, (iii) pyridyl group or (iv) thienyl group, $R^3$ is (i) hydrogen atom, (ii) a halogen atom, (iii) a $C_{1-4}$ alkyl group or (iv) a $C_{1-4}$ alkoxyl group, $R^4$ is (i) hydrogen atom or (ii) a $C_{1-4}$ alkyl group. $R^5$ is (i) a not-substituted $C_{1-5}$ alkyl group or a $C_{1-5}$ alkyl group substituted by a halogen atom, (ii) phenyl group or (iii) thienyl group and Z is (i) a $C_{1-6}$ alkylene group, (ii) a $C_{2-6}$ alkenylene group or (iii) a $C_{3-6}$ alkynylene group or a pharmacologically acceptable salt thereof. According to the present invention, an anti-allergic agent and a therapeutic agent for ischemic heart disease without toxicity can be provided.

10 Claims, No Drawings

PIPERIDINE COMPOUNDS WHICH HAVE USEFUL PHARMACEUTICAL ACTIVITY

BACKGROUND OF THE INVENTION

The present invention relates to a piperidine derivative having the formula (I):

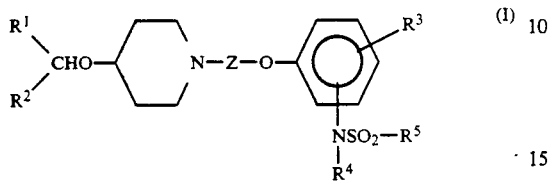

wherein $R^1$ and $R^2$, which may be the same or different from each other, are (i) a not-substituted phenyl group or a phenyl group substituted by a halogen atom, trifluoromethyl group, a $C_{1-5}$ alkyl group or a $C_{1-5}$ alkoxyl group, (ii) a $C_{3-7}$ cycloalkyl group, (iii) pyridyl group or (iv) thienyl group, $R^3$ is (i) hydrogen atom, (ii) a halogen atom, (iii) a $C_{1-4}$ alkyl group or (iv) a $C_{1-4}$ alkoxyl group, $R^4$ is (i) hydrogen atom or (ii) a $C_{1-4}$ alkyl group, $R^5$ is (i) a not-substituted $C_{1-5}$ alkyl group or a $C_{1-5}$ alkyl group substituted by a halogen atom, (ii) phenyl group or (iii) thienyl group and Z is (i) a $C_{1-6}$ alkylene group, (ii) a $C_{2-6}$ alkenylene group or (iii) a $C_{3-6}$ alkynylene group or a pharmacologically acceptable salt thereof and a compound useful as an intermediate for synthesizing the compound having the formula (I).

Many factors participate in the onset or the exacerbation of allergic diseases. Above all, the chemical mediators which are released with allergic reactions play particularly significant role.

Drugs for inhibiting the biosynthesis or release of chemical mediators, drugs for degradating or antagonizing chemical mediators and the like have been studied and applied for clinical use as anti-allergic drugs.

There have been found many piperidine derivatives having anti-allergic action. As compounds whose structure is partly similar to that of the compound of the present invention, for example, there are those compounds described in Japanese Unexamined Patent Publication No. 94962/1985, Japanese Unexamined Patent Publication No. 194068/1986, Japanese Unexamined Patent Publication No. 242574/1989, Japanese Unexamined Patent Publication No. 25465/1990 and Japanese Unexamined Patent Publication No. 108689/1990. However there are no compounds having sulfonamide group in molecule among the compounds disclosed in the above-mentioned publications. Furthermore, as to the pharmacological action of those compounds, there are no description that those compounds may have the inhibitory activity of mediator release.

An object of the present invention is to provide a novel compound having the inhibitory activity of mediator release, antihistaminic activity and the like, an anti-allergic agent comprising the same as an effective ingredient, a treatment agent for ischemic heart disease comprising the same as an effective ingredient and an intermediate compound for synthesizing the same.

This and the other objects of the present invention will become apparent from the description hereinafter.

SUMMARY OF THE INVENTION

It has now been found that a piperizine derivative having sulfonamide group in its molecule shows the inhibitory activity of mediator release, antihistaminic activity and therapeutic activity for ischemic heart disease.

That is, the present invention relates to a piperidine derivative having the formula (I):

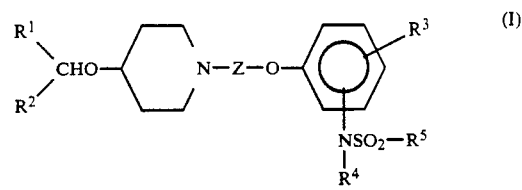

wherein $R^1$ and $R^2$, which may be the same or different from each other, are (i) a not-substituted phenyl group or a phenyl group substituted by a halogen atom, trifluoromethyl group, a $C_{1-5}$ alkyl group or a $C_{1-5}$ alkoxyl group, (ii) a $C_{3-7}$ cycloalkyl group, (iii) pyridyl group or (iv) thienyl group, $R^3$ is (i) hydrogen atom, (ii) a halogen atom, (iii) a $C_{1-4}$ alkyl group or (iv) a $C_{1-4}$ alkoxyl group, $R^4$ is (i) hydrogen atom or (ii) a $C_{1-4}$ alkyl group, $R^5$ is (i) a not-substituted $C_{1-5}$ alkyl group or a $C_{1-5}$ alkyl group substituted by a halogen atom, (ii) phenyl group or (iii) thienyl group and Z is (i) a $C_{1-6}$ alkylene group, (ii) a $C_{2-6}$ alkenylene group or (iii) a $C_{3-6}$ alkynylene group or a pharmacologically acceptable salt thereof, an anti-allergic agent comprising as an effective ingredient the above-mentioned piperidine derivative or a pharmacologically acceptable salt thereof, a therapeutic agent for ischemic heart disease comprising as an effective ingredient the above-mentioned piperidine derivative or a pharmacologically acceptable salt thereof, a piperidine derivative having the formula (II):

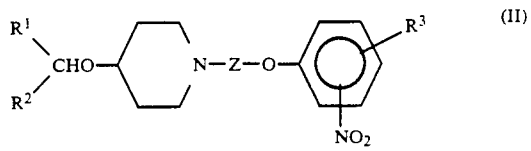

wherein $R^1$ and $R^2$, which may be the same or different from each other, are (i) a not-substituted phenyl group or a phenyl group substituted by a halogen atom, trifluoromethyl group, a $C_{1-5}$ alkyl group or a $C_{1-5}$ alkoxyl group, (ii) a $C_{3-7}$ cycloalkyl group, (iii) pyridyl group or (iv) thienyl group, $R^3$ is (i) hydrogen atom, (ii) a halogen atom, (iii) a $C_{1-4}$ alkyl group or (iv) a $C_{1-4}$ alkoxyl group, and Z is (i) a $C_{1-6}$ alkylene group, (ii) a $C_{2-6}$ alkenylene group or (iii) a $C_{3-6}$ alkynylene group, which is an intermediate for preparing the above-mentioned piperidine derivative, and a piperidine derivative having the formula (III):

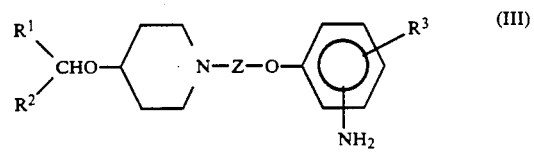

wherein $R^1$ and $R^2$, which may be the same or different from each other, are (i) a not-substituted phenyl group or a phenyl group substituted by a halogen atom, trifluoromethyl group, a $C_{1-5}$ alkyl group or a $C_{1-5}$ alkoxyl group, (ii) a $C_{3-7}$ cycloalkyl group, (iii) pyridyl group or (iv) thienyl group, $R^3$ is (i) hydrogen atom, (ii) a halogen atom, (iii) a $C_{1-4}$ alkyl group or (iv) a $C_{1-4}$ alkoxyl group, and Z is (i) a $C_{1-6}$ alkylene group, (ii) a $C_{2-6}$ alkenylene group or (iii) a $C_{3-6}$ alkynylene group, which is an intermediate for preparing the above-mentioned piperidine derivative.

DETAILED DESCRIPTION

The piperidine derivative having the formula (I), (II) or (III) are explained below.

As substituted phenyl groups represented by $R^1$ and $R^2$ in the above-mentioned formula (I), (II) or (III), there are, for example, phenyl groups substituted by one or more halogen atoms, such as 2-fluoro-, 3-fluoro-, 4-fluoro-, 2,4-difluoro-, 2,5-difluoro-, 3,4-difluoro-, 2-chloro-, 3-chloro-, 4-chloro-, 3,4-dichloro-, 4-bromo- and 4-iodo- phenyl groups, phenyl groups substituted by trifluoromethyl group, such as 2-trifluoromethyl-, 3-trifluoromethyl- and 4-trifluoromethyl- phenyl groups, phenyl groups substituted by one or more straight chain or branched chain $C_{1-5}$ alkyl groups, such as 2-methyl-, 3-methyl-, 4-methyl-, 2,4-dimethyl-, 3,4-dimethyl-, 4-ethyl-, 4-n-propyl-, 4-isopropyl-, 4-n-butyl-, 4-isobutyl-, 4-tert-butyl- and 4-n-pentyl- phenyl groups and phenyl groups substituted by one or more straight chain or branched chain $C_{1-5}$ alkoxyl group, such as 4-methoxy-, 3,4-dimethoxy-, 4-ethoxy-, 4-n-propoxy-, 4-isopropoxy-, 4-n-butoxy-, 4-isobutoxy- and 4-n-pentyloxy- phenyl groups.

As cycloalkyl groups represented by $R^1$ and $R^2$, there are, for example, $C_{3-7}$ cycloalkyl groups such as cyclopropyl, cyclobutyl, cyclopentyl, cyclohexyl and cycloheptyl.

As pyridyl groups represented by $R^1$ and $R^2$, there are, for example, pyridyl groups such as 2-pyridyl, 3-pyridyl and 4-pyridyl.

As thienyl groups represented by $R^1$ and $R^2$, there are, for example, thienyl groups such as 2-thienyl and 3-thienyl.

As $R^3$, there are, for example, hydrogen atom, halogen atoms such as fluorine, chlorine, bromine and iodine, $C_{1-4}$ alkyl groups such as methyl, ethyl, n-propyl, isopropyl and butyl, $C_{1-4}$ alkoxyl groups such as methoxy, ethoxy, n-propoxy, isopropoxy and butoxy and the like.

As $R^4$, there are, for example, hydrogen atom, $C_{1-4}$ alkyl groups such as methyl, ethyl, n-propyl, isopropyl and butyl and the like.

As $R^5$, there are, for example, $C_{1-5}$ alkyl groups which may be substituted by one or more halogen atoms such as methyl, ethyl, n-propyl, isopropyl, n-butyl, n-pentyl, fluoromethyl, difluoromethyl, trifluoromethyl, chloromethyl, trichloromethyl, 2,2,2-trifluoroethyl and 2-chloroethyl, phenyl group, thienyl groups such as 2-thienyl and 3-thienyl and the like.

As Z, there are, for example, straight chain or branched chain $C_{1-6}$ alkylene groups such as methylene, ethylene, trimethylene, 1-methylethylene, 2-methylethylene, tetramethylene, 1-methyltrimethylene, 2-methyltrimethylene, 3-methyltrimethylene, 1-ethylethylene, pentamethylene, 1-methyltetramethylene, 2-methyltetramethylene, 3-methyltetramethylene, 4-methyltetramethylene, 1,1-dimethyltrimethylene and hexamethylene, straight chain or branched chain $C_{2-6}$ alkenylene groups such as vinylene, 1-propenylene, 1-butenylene, 2-butenylene, 2-methylprop-1-enylene, 3-methylprop-1-enylene and 2-pentenylene, straight chain or branched chain $C_{3-6}$ alkynylene groups such as 1-propynylene, 1-butynylene, 2-butynylene, 3-methylprop-1-ynylene and 2-pentynylene and the like.

When there are one or more asymmetric carbon atoms in the compounds having the formula (I), (II) or (III), a racemate, a diastereoisomer and each optical isomer thereof are all included in the present invention. If there are geometrical isomers, (E)-form, (Z)-form and the mixture thereof are also included in the present invention.

As concrete examples of the piperidine derivatives of the present invention having the formula (I), the piperidine derivative wherein $R^1$, $R^2$, Z, $R^3$, $R^4$ and $R^5$ are respectively the groups shown in the following Table 1 can be exemplified.

However, it is to be understood that the present invention is not limited to those compounds.

TABLE 1

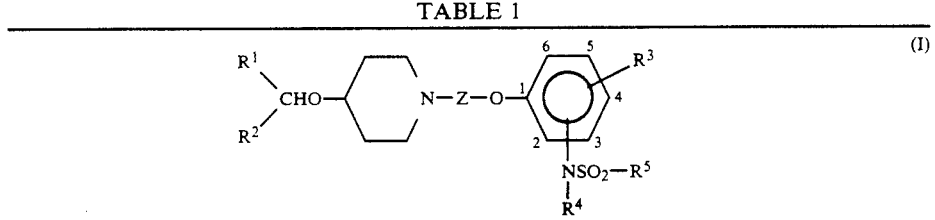

| No. | $R^1$ | $R^2$ | Z | $R^3$ | $-NSO_2-R^5$ $R^4$ |
|---|---|---|---|---|---|
| 1 | $C_6H_5$ | $C_6H_5$ | $-CH_2-$ | H | 2-NHSO$_2$CH$_3$ |
| 2 | $C_6H_5$ | $C_6H_5$ | $-(CH_2)_2-$ | H | 2-NHSO$_2$CH$_3$ |
| 3 | $C_6H_5$ | $C_6H_5$ | $-(CH_2)_3-$ | H | 2-NHSO$_2$CH$_3$ |
| 4 | $C_6H_5$ | $C_6H_5$ | $-(CH_2)_3-$ | H | 3-NHSO$_2$CH$_3$ |
| 5 | $C_6H_5$ | $C_6H_5$ | $-(CH_2)_3-$ | H | 4-NHSO$_2$CH$_3$ |
| 6 | $C_6H_5$ | $C_6H_5$ | $-(CH_2)_3-$ | H | 2-NHSO$_2$C$_2$H$_5$ |
| 7 | $C_6H_5$ | $C_6H_5$ | $-(CH_2)_3-$ | H | 2-NHSO$_2$C$_3$H$_7$ |
| 8 | $C_6H_5$ | $C_6H_5$ | $-(CH_2)_3-$ | H | 2-NHSO$_2$CF$_3$ |
| 9 | $C_6H_5$ | $C_6H_5$ | $-(CH_2)_3-$ | H | 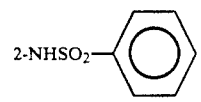 |

TABLE 1-continued

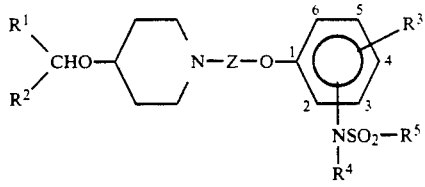

(I)

| No. | R¹ | R² | Z | R³ | $-\underset{R^4}{N}SO_2-R^5$ |
|---|---|---|---|---|---|
| 10 | $C_6H_5$ | $C_6H_5$ | $-(CH_2)_3-$ | H | 2-NHSO₂-⟨thiophene⟩ |
| 11 | $C_6H_5$ | $C_6H_5$ | $-(CH_2)_3-$ | H | 2-N(CH₃)SO₂CH₃ |
| 12 | $C_6H_5$ | $C_6H_5$ | $-(CH_2)_3-$ | 5-F | 2-NHSO₂CH₃ |
| 13 | $C_6H_5$ | $C_6H_5$ | $-(CH_2)_3-$ | 4-Cl | 2-NHSO₂CH₃ |
| 14 | $C_6H_5$ | $C_6H_5$ | $-(CH_2)_3-$ | 5-Cl | 2-NHSO₂CH₃ |
| 15 | $C_6H_5$ | $C_6H_5$ | $-(CH_2)_3-$ | 3-CH₃ | 2-NHSO₂CH₃ |
| 16 | $C_6H_5$ | $C_6H_5$ | $-(CH_2)_3-$ | 4-CH₃ | 2-NHSO₂CH₃ |
| 17 | $C_6H_5$ | $C_6H_5$ | $-(CH_2)_3-$ | 5-CH₃ | 2-NHSO₂CH₃ |
| 18 | $C_6H_5$ | $C_6H_5$ | $-(CH_2)_3-$ | 4-OCH₃ | 2-NHSO₂CH₃ |
| 19 | $C_6H_5$ | $C_6H_5$ | $-CH(CH_3)-CH_2-CH_2-$ | H | 2-NHSO₂CH₃ |
| 20 | $C_6H_5$ | $C_6H_5$ | $-CH_2-CH(CH_3)-CH_2-$ | H | 2-NHSO₂CH₃ |
| 21 | $C_6H_5$ | $C_6H_5$ | $-CH_2-CH_2-CH(CH_3)-$ | H | 2-NHSO₂CH₃ |
| 22 | $C_6H_5$ | $C_6H_5$ | $-(CH_2)_4-$ | H | 2-NHSO₂CH₃ |
| 23 | $C_6H_5$ | $C_6H_5$ | $-CH_2-CH=CH-CH_2-$ [(E) form] | H | 2-NHSO₂CH₃ |
| 24 | $C_6H_5$ | $C_6H_5$ | $-CH_2-CH=CH-CH_2-$ [(Z) form] | H | 2-NHSO₂CH₃ |
| 25 | $C_6H_5$ | $C_6H_5$ | $-CH_2-C\equiv C-CH_2-$ | H | 2-NHSO₂CH₃ |
| 26 | $C_6H_5$ | $C_6H_5$ | $-C(CH_3)_2-CH_2-CH_2-$ | H | 2-NHSO₂CH₃ |
| 27 | $C_6H_5$ | $C_6H_5$ | $-CH_2-C(CH_3)_2-CH_2-$ | H | 2-NHSO₂CH₃ |
| 28 | $C_6H_5$ | $C_6H_5$ | $-(CH_2)_5-$ | H | 2-NHSO₂CH₃ |
| 29 | $C_6H_5$ | $4-FC_6H_4$ | $-(CH_2)_3-$ | H | 2-NHSO₂CH₃ |
| 30 | $C_6H_5$ | $2,4-F_2C_6H_3$ | $-(CH_2)_3-$ | H | 2-NHSO₂CH₃ |
| 31 | $C_6H_5$ | $2-ClC_6H_4$ | $-(CH_2)_3-$ | H | 2-NHSO₂CH₃ |
| 32 | $C_6H_5$ | $4-ClC_6H_4$ | $-(CH_2)_3-$ | H | 2-NHSO₂CH₃ |
| 33 | $C_6H_5$ | $3-CF_3C_6H_4$ | $-(CH_2)_3-$ | H | 2-NHSO₂CH₃ |
| 34 | $C_6H_5$ | $4-CF_3C_6H_4$ | $-(CH_2)_3-$ | H | 2-NHSO₂CH₃ |
| 35 | $C_6H_5$ | $2-CH_3C_6H_4$ | $-(CH_2)_3-$ | H | 2-NHSO₂CH₃ |
| 36 | $C_6H_5$ | $3-CH_3C_6H_4$ | $-(CH_2)_3-$ | H | 2-NHSO₂CH₃ |
| 37 | $C_6H_5$ | $4-CH_3C_6H_4$ | $-(CH_2)_3-$ | H | 2-NHSO₂CH₃ |
| 38 | $C_6H_5$ | $4-C_2H_5C_6H_4$ | $-(CH_2)_3-$ | H | 2-NHSO₂CH₃ |
| 39 | $C_6H_5$ | $4-CH_3OC_6H_4$ | $-(CH_2)_3-$ | H | 2-NHSO₂CH₃ |
| 40 | $4-FC_6H_4$ | $4-FC_6H_4$ | $-(CH_2)_3-$ | H | 2-NHSO₂CH₃ |
| 41 | $4-ClC_6H_4$ | $4-ClC_6H_4$ | $-(CH_2)_3-$ | H | 2-NHSO₂CH₃ |
| 42 | $4-CH_3C_6H_4$ | $4-CH_3C_6H_4$ | $-(CH_2)_3-$ | H | 2-NHSO₂CH₃ |
| 43 | $4-CH_3OC_6H_4$ | $4-CH_3OC_6H_4$ | $-(CH_2)_3-$ | H | 2-NHSO₂CH₃ |
| 44 | cyclopentyl | $C_6H_5$ | $-(CH_2)_3-$ | H | 2-NHSO₂CH₃ |
| 45 | cyclohexyl | $C_6H_5$ | $-(CH_2)_3-$ | H | 2-NHSO₂CH₃ |
| 46 | 2-pyridyl | $C_6H_5$ | $-(CH_2)_3-$ | H | 2-NHSO₂CH₃ |
| 47 | 2-pyridyl | $C_6H_5$ | $-CH(CH_3)-CH_2-CH_2-$ | H | 2-NHSO₂CH₃ |

TABLE 1-continued $$\text{(I)}$$

Structure: $R^1R^2CH$-O-(piperidine with N)-Z-O-(phenyl with positions 1-6, $R^3$ at 4, $NSO_2-R^5$ with $R^4$ at 2)

| No. | $R^1$ | $R^2$ | Z | $R^3$ | $-NSO_2-R^5$ / $R^4$ |
|---|---|---|---|---|---|
| 48 | 2-pyridyl | $C_6H_5$ | $-CH_2-CH=CH-CH_2-$ [(E) form] | H | 2-$NHSO_2CH_3$ |
| 49 | 2-pyridyl | $C_6H_5$ | $-CH_2-CH=CH-CH_2-$ [(Z) form] | H | 2-$NHSO_2CH_3$ |
| 50 | 2-pyridyl | 4-$ClC_6H_4$ | $-(CH_2)_3-$ | H | 2-$NHSO_2CH_3$ |
| 51 | 3-pyridyl | $C_6H_5$ | $-(CH_2)_3-$ | H | 2-$NHSO_2CH_3$ |
| 52 | 3-pyridyl | $C_6H_5$ | $-CH(CH_3)-CH_2-CH_2-$ | H | 2-$NHSO_2CH_3$ |
| 53 | 3-pyridyl | $C_6H_5$ | $-CH_2-CH=CH-CH_2-$ [(E) form] | H | 2-$NHSO_2CH_3$ |
| 54 | 3-pyridyl | $C_6H_5$ | $-CH_2-CH=CH-CH_2-$ [(Z) form] | H | 2-$NHSO_2CH_3$ |
| 55 | 4-pyridyl | $C_6H_5$ | $-(CH_2)_3-$ | H | 2-$NHSO_2CH_3$ |
| 56 | 4-pyridyl | $C_6H_5$ | $-CH_2-CH=CH-CH_2-$ [(E) form] | H | 2-$NHSO_2CH_3$ |
| 57 | 4-pyridyl | $C_6H_5$ | $-CH_2-CH=CH-CH_2-$ [(Z) form] | H | 2-$NHSO_2CH_3$ |
| 58 | 2-thienyl | $C_6H_5$ | $-(CH_2)_2-$ | H | 2-$NHSO_2CH_3$ |
| 59 | 2-thienyl | $C_6H_5$ | $-(CH_2)_3-$ | H | 2-$NHSO_2CH_3$ |
| 60 | 2-thienyl | $C_6H_5$ | $-CH(CH_3)-CH_2-CH_2-$ | H | 2-$NHSO_2CH_3$ |
| 61 | 2-thienyl | $C_6H_5$ | $-CH_2-CH_2-CH(CH_3)-$ | H | 2-$NHSO_2CH_3$ |
| 62 | 2-thienyl | $C_6H_5$ | $-(CH_2)_4-$ | H | 2-$NHSO_2CH_3$ |
| 63 | 2-thienyl | $C_6H_5$ | $-CH_2-CH=CH-CH_2-$ [(E) form] | H | 2-$NHSO_2CH_3$ |
| 64 | 2-thienyl | $C_6H_5$ | $-CH_2-CH=CH-CH_2-$ [(E) form] | H | 2-$NHSO_2CH_3$ |
| 65 | 2-thienyl | $C_6H_5$ | $-C(CH_3)_2-CH_2-CH_2-$ | H | 2-$NHSO_2CH_3$ |
| 66 | 2-thienyl | $C_6H_5$ | $-CH_2-C(CH_3)_2-CH_2-$ | H | 2-$NHSO_2CH_3$ |
| 67 | 3-thienyl | $C_6H_5$ | $-(CH_2)_2-$ | H | 2-$NHSO_2CH_3$ |
| 68 | 3-thienyl | $C_6H_5$ | $-(CH_2)_3-$ | H | 2-$NHSO_2CH_3$ |
| 69 | 3-thienyl | $C_6H_5$ | $-CH(CH_3)-CH_2-CH_2-$ | H | 2-$NHSO_2CH_3$ |
| 70 | 3-thienyl | $C_6H_5$ | $-(CH_2)_4-$ | H | 2-$NHSO_2CH_3$ |
| 71 | 3-thienyl | $C_6H_5$ | $-CH_2-CH=CH-CH_2-$ [(E) form] | H | 2-$NHSO_2CH_3$ |
| 72 | 3-thienyl | $C_6H_5$ | $-CH_2-CH=CH-CH_2-$ [(Z) form] | H | 2-$NHSO_2CH_3$ |
| 73 | 3-thienyl | $C_6H_5$ | $-C(CH_3)_2-CH_2-CH_2-$ | H | 2-$NHSO_2CH_3$ |
| 74 | 2-thienyl | 2-thienyl | $-(CH_2)_2-$ | H | 2-$NHSO_2CH_3$ |
| 75 | 2-thienyl | 2-thienyl | $-(CH_2)_3-$ | H | 2-$NHSO_2CH_3$ |
| 76 | 2-thienyl | 2-thienyl | $-CH(CH_3)-CH_2-CH_2-$ | H | 2-$NHSO_2CH_3$ |
| 77 | 2-thienyl | 2-thienyl | $-(CH_2)_4-$ | H | 2-$NHSO_2CH_3$ |
| 78 | 2-thienyl | 2-thienyl | $-CH_2-CH=CH-CH_2-$ [(E) form] | H | 2-$NHSO_2CH_3$ |
| 79 | 2-thienyl | 2-thienyl | $-CH_2-CH=CH-CH_2-$ [(Z) form] | H | 2-$NHSO_2CH_3$ |

TABLE 1-continued $$\text{(I)}$$

Structure: R¹R²CH(OH) attached to piperidine ring, N—Z—O—phenyl (positions 1,2,3,4,5,6) with R³ and NSO₂—R⁵ / R⁴ substituents.

| No. | R¹ | R² | Z | R³ | —NSO₂—R⁵ / R⁴ |
|---|---|---|---|---|---|
| 80 | 2-thienyl | 2-thienyl | —C(CH₃)(CH₃)—CH₂—CH₂— | H | 2-NHSO₂CH₃ |
| 81 | 2-thienyl | 3-thienyl | —(CH₂)₂— | H | 2-NHSO₂CH₃ |
| 82 | 2-thienyl | 3-thienyl | —(CH₂)₃— | H | 2-NHSO₂CH₃ |
| 83 | 2-thienyl | 3-thienyl | —CH(CH₃)—CH₂—CH₂— | H | 2-NHSO₂CH₃ |
| 84 | 2-thienyl | 3-thienyl | —(CH₂)₄— | H | 2-NHSO₂CH₃ |
| 85 | 2-thienyl | 3-thienyl | —CH₂—CH=CH—CH₂—[(E) form] | H | 2-NHSO₂CH₃ |
| 86 | 2-thienyl | 3-thienyl | —CH₂—CH=CH—CH₂—[(Z) form] | H | 2-NHSO₂CH₃ |
| 87 | 2-thienyl | 3-thienyl | —C(CH₃)(CH₃)—CH₂—CH₂— | H | 2-NHSO₂CH₃ |
| 88 | 3-thienyl | 3-thienyl | —(CH₂)₂— | H | 2-NHSO₂CH₃ |
| 89 | 3-thienyl | 3-thienyl | —(CH₂)₃— | H | 2-NHSO₂CH₃ |
| 90 | 3-thienyl | 3-thienyl | —CH(CH₃)—CH₂—CH₂— | H | 2-NHSO₂CH₃ |
| 91 | 3-thienyl | 3-thienyl | —(CH₂)₄— | H | 2-NHSO₂CH₃ |
| 92 | 3-thienyl | 3-thienyl | —CH₂—CH=CH—CH₂—[(E) form] | H | 2-NHSO₂CH₃ |
| 93 | 3-thienyl | 3-thienyl | —CH₂—CH=CH—CH₂—[(Z) form] | H | 2-NHSO₂CH₃ |
| 94 | 3-thienyl | 3-thienyl | —C(CH₃)(CH₃)—CH₂—CH₂— | H | 2-NHSO₂CH₃ |
| 95 | 3-thienyl | 3-thienyl | —CH₂—C(CH₃)(CH₃)—CH₂— | H | 2-NHSO₂CH₃ |
| 96 | 2-pyridyl | 2-pyridyl | —(CH₂)₂— | H | 2-NHSO₂CH₃ |
| 97 | 2-pyridyl | 2-pyridyl | —(CH₂)₃— | H | 2-NHSO₂CH₃ |
| 98 | 2-pyridyl | 2-pyridyl | —CH(CH₃)—CH₂—CH₂— | H | 2-NHSO₂CH₃ |
| 99 | 2-pyridyl | 2-pyridyl | —(CH₂)₄— | H | 2-NHSO₂CH₃ |
| 100 | 2-pyridyl | 2-pyridyl | —CH₂—CH=CH—CH₂—[(E) form] | H | 2-NHSO₂CH₃ |
| 101 | 2-pyridyl | 2-pyridyl | —CH₂—CH=CH—CH₂—[(Z) form] | H | 2-NHSO₂CH₃ |
| 102 | 2-pyridyl | 2-pyridyl | —C(CH₃)(CH₃)—CH₂—CH₂— | H | 2-NHSO₂CH₃ |
| 103 | 3-pyridyl | 3-pyridyl | —(CH₂)₂— | H | 2-NHSO₂CH₃ |
| 104 | 3-pyridyl | 3-pyridyl | —(CH₂)₃— | H | 2-NHSO₂CH₃ |

TABLE 1-continued $$\text{(I)} \quad \begin{array}{c} R^1 \\ | \\ R^2 \end{array} \text{CH-O-} \underset{\phantom{N}}{\bigcirc} \text{-N-Z-O-} \underset{\substack{| \\ NSO_2-R^5 \\ | \\ R^4}}{\bigcirc} \begin{array}{c} R^3 \\ \end{array}$$

| No. | R¹ | R² | Z | R³ | $-NSO_2-R^5$ / $R^4$ |
|---|---|---|---|---|---|
| 105 | 3-pyridyl | 3-pyridyl | —CH(CH₃)—CH₂—CH₂— | H | 2-NHSO₂CH₃ |
| 106 | 3-pyridyl | 3-pyridyl | —(CH₂)₄— | H | 2-NHSO₂CH₃ |
| 107 | 3-pyridyl | 3-pyridyl | —CH₂—CH=CH—CH₂—[(E) form] | H | 2-NHSO₂CH₃ |
| 108 | 3-pyridyl | 3-pyridyl | —CH₂—CH=CH—CH₂—[(Z) form] | H | 2-NHSO₂CH₃ |
| 109 | 3-pyridyl | 3-pyridyl | —C(CH₃)₂—CH₂—CH₂— | H | 2-NHSO₂CH₃ |
| 110 | 2-pyridyl | 2-thienyl | —(CH₂)₂— | H | 2-NHSO₂CH₃ |
| 111 | 2-pyridyl | 2-thienyl | —(CH₂)₃— | H | 2-NHSO₂CH₃ |
| 112 | 2-pyridyl | 2-thienyl | —CH(CH₃)—CH₂—CH₂— | H | 2-NHSO₂CH₃ |
| 113 | 2-pyridyl | 2-thienyl | —(CH₂)₄— | H | 2-NHSO₂CH₃ |
| 114 | 2-pyridyl | 2-thienyl | —CH₂—CH=CH—CH₂—[(E) form] | H | 2-NHSO₂CH₃ |
| 115 | 2-pyridyl | 2-thienyl | —CH₂—CH=CH—CH₂—[(Z) form] | H | 2-NHSO₂CH₃ |
| 116 | 2-pyridyl | 2-thienyl | —C(CH₃)₂—CH₂—CH₂— | H | 2-NHSO₂CH₃ |
| 117 | 2-pyridyl | 3-thienyl | —(CH₂)₂— | H | 2-NHSO₂CH₃ |
| 118 | 2-pyridyl | 3-thienyl | —(CH₂)₃— | H | 2-NHSO₂CH₃ |
| 119 | 2-pyridyl | 3-thienyl | —CH(CH₃)—CH₂—CH₂— | H | 2-NHSO₂CH₃ |
| 120 | 2-pyridyl | 3-thienyl | —(CH₂)₄— | H | 2-NHSO₂CH₃ |
| 121 | 2-pyridyl | 3-thienyl | —CH₂—CH=CH—CH₂—[(E) form] | H | 2-NHSO₂CH₃ |
| 122 | 2-pyridyl | 3-thienyl | —CH₂—CH=CH—CH₂—[(Z) form] | H | 2-NHSO₂CH₃ |
| 123 | 2-pyridyl | 3-thienyl | —C(CH₃)₂—CH₂—CH₂— | H | 2-NHSO₂CH₃ |
| 124 | 3-pyridyl | 2-thienyl | —(CH₂)₂— | H | 2-NHSO₂CH₃ |
| 125 | 3-pyridyl | 2-thienyl | —(CH₂)₃— | H | 2-NHSO₂CH₃ |
| 126 | 3-pyridyl | 2-thienyl | —CH(CH₃)—CH₂—CH₂— | H | 2-NHSO₂CH₃ |
| 127 | 3-pyridyl | 2-thienyl | —(CH₂)₄— | H | 2-NHSO₂CH₃ |
| 128 | 3-pyridyl | 2-thienyl | —CH₂—CH=CH—CH₂—[(E) form] | H | 2-NHSO₂CH₃ |
| 129 | 3-pyridyl | 2-thienyl | —CH₂—CH=CH—CH₂—[(Z) form] | H | 2-NHSO₂CH₃ |
| 130 | 3-pyridyl | 2-thienyl | —C(CH₃)₂—CH₂—CH₂— | H | 2-NHSO₂CH₃ |
| 131 | 3-pyridyl | 3-thienyl | —(CH₂)₂— | H | 2-NHSO₂CH₃ |
| 132 | 3-pyridyl | 3-thienyl | —(CH₂)₃— | H | 2-NHSO₂CH₃ |

TABLE 1-continued $$\begin{array}{c} R^1 \\ \diagdown \\ R^2 \diagup \end{array} CHO-\boxed{\phantom{X}N}-Z-O-\boxed{\phantom{X}}\begin{array}{c} R^3 \\ NSO_2-R^5 \\ | \\ R^4 \end{array} \quad (I)$$

| No. | $R^1$ | $R^2$ | Z | $R^3$ | $-NSO_2-R^5$<br>$\|$<br>$R^4$ |
|-----|-------|-------|---|-------|--------|
| 133 | 3-pyridyl | 3-thienyl | $-CH-CH_2-CH_2-$<br>$\|$<br>$CH_3$ | H | 2-NHSO$_2$CH$_3$ |
| 134 | 3-pyridyl | 3-thienyl | $-(CH_2)_4-$ | H | 2-NHSO$_2$CH$_3$ |
| 135 | 3-pyridyl | 3-thienyl | $-CH_2-CH=CH-CH_2-$ [(E) form] | H | 2-NHSO$_2$CH$_3$ |
| 136 | 3-pyridyl | 3-thienyl | $-CH_2-CH=CH-CH_2-$ [(Z) form] | H | 2-NHSO$_2$CH$_3$ |
| 137 | 3-pyridyl | 3-thienyl | $CH_3$<br>$\|$<br>$-C-CH_2-CH_2-$<br>$\|$<br>$CH_3$ | H | 2-NHSO$_2$CH$_3$ |
| 138 | 4-pyridyl | 2-thienyl | $-(CH_2)_2-$ | H | 2-NHSO$_2$CH$_3$ |
| 139 | 4-pyridyl | 2-thienyl | $-(CH_2)_3-$ | H | 2-NHSO$_2$CH$_3$ |
| 140 | 4-pyridyl | 2-thienyl | $-CH-CH_2-CH_2-$<br>$\|$<br>$CH_3$ | H | 2-NHSO$_2$CH$_3$ |
| 141 | 4-pyridyl | 2-thienyl | $-(CH_2)_4-$ | H | 2-NHSO$_2$CH$_3$ |
| 142 | 4-pyridyl | 2-thienyl | $-CH_2-CH=CH-CH_2-$ [(E) form] | H | 2-NHSO$_2$CH$_3$ |
| 143 | 4-pyridyl | 2-thienyl | $-CH_2-CH=CH-CH_2-$ [(Z) form] | H | 2-NHSO$_2$CH$_3$ |
| 144 | 4-pyridyl | 2-thienyl | $CH_3$<br>$\|$<br>$-C-CH_2-CH_2-$<br>$\|$<br>$CH_3$ | H | 2-NHSO$_2$CH$_3$ |
| 145 | 4-pyridyl | 3-thienyl | $-(CH_2)_2-$ | H | 2-NHSO$_2$CH$_3$ |
| 146 | 4-pyridyl | 3-thienyl | $-(CH_2)_3-$ | H | 2-NHSO$_2$CH$_3$ |
| 147 | 4-pyridyl | 3-thienyl | $-CH-CH_2-CH_2-$<br>$\|$<br>$CH_3$ | H | 2-NHSO$_2$CH$_3$ |
| 148 | 4-pyridyl | 3-thienyl | $-(CH_2)_4-$ | H | 2-NHSO$_2$CH$_3$ |
| 149 | 4-pyridyl | 3-thienyl | $-CH_2-CH=CH-CH_2-$ [(E) form] | H | 2-NHSO$_2$CH$_3$ |
| 150 | 4-pyridyl | 3-thienyl | $-CH_2-CH=CH-CH_2-$ [(Z) form] | H | 2-NHSO$_2$CH$_3$ |
| 151 | 4-pyridyl | 3-thienyl | $CH_3$<br>$\|$<br>$-C-CH_2-CH_2-$<br>$\|$<br>$CH_3$ | H | 2-NHSO$_2$CH$_3$ |

The present invention also includes a pharmacologically acceptable salt of the piperidine derivatives having the formula (I).

As such salts, there are, for example, a salt with hydrohalogenic acid such as hydrofluoric acid, hydrochloric acid, hydrobromic acid or hydroiodic acid, a salt with an inorganic acid such as nitric acid, perchloric acid, sulfuric acid, phosphoric acid or carbonic acid, a salt with a lower alkyl sulfonic acid such as methanesulfonic acid, trifluoromethanesulfonic acid or ethanesulfonic acid, a salt with an arylsulfonic acid such as benzenesulfonic acid or p-toluenesulfonic acid, a salt with an organic acid such as fumaric acid, succinic acid, citric acid, tartaric acid, oxalic acid or maleic acid, a salt with an amino acid such as glycine, alanine, glutamic acid or aspartic acid and the like.

When $R^4$ in the formula (I) is hydrogen atom, a salt with alkaline metal such as sodium or pottasium can be exemplified.

As concrete examples of the piperidine derivatives of the present invention having the formula (II) or (III), the piperidine derivatives wherein $R^1$, $R^2$, Z and $R^3$ in the formula (II) or (III) are respectively the groups shown in the following Table 2 can be exemplified.

However, it is to be understood that the present invention is not limited to those compounds.

TABLE 2

$$\text{R}^1\text{R}^2\text{CHO-piperidine-N-Z-O}^1\text{-C}_6\text{H}_3(\text{R}^3)(\text{NO}_2) \quad (II)$$

$$\text{R}^1\text{R}^2\text{CHO-piperidine-N-Z-O}^1\text{-C}_6\text{H}_3(\text{R}^3)(\text{NH}_2) \quad (III)$$

| No. | R$^1$ | R$^2$ | Z | R$^3$ | position substituted by —NO$_2$ in (II) or —NH$_2$ in (III) |
|---|---|---|---|---|---|
| 1 | C$_6$H$_5$ | C$_6$H$_5$ | —CH$_2$— | H | 2- |
| 2 | C$_6$H$_5$ | C$_6$H$_5$ | —(CH$_2$)$_2$— | H | 2- |
| 3 | C$_6$H$_5$ | C$_6$H$_5$ | —(CH$_2$)$_3$— | H | 2- |
| 4 | C$_6$H$_5$ | C$_6$H$_5$ | —(CH$_2$)$_3$— | H | 3- |
| 5 | C$_6$H$_5$ | C$_6$H$_5$ | —(CH$_2$)$_3$— | H | 4- |
| 6 | C$_6$H$_5$ | C$_6$H$_5$ | —(CH$_2$)$_3$— | 5-F | 2- |
| 7 | C$_6$H$_5$ | C$_6$H$_5$ | —(CH$_2$)$_3$— | 4-Cl | 2- |
| 8 | C$_6$H$_5$ | C$_6$H$_5$ | —(CH$_2$)$_3$— | 3-CH$_3$ | 2- |
| 9 | C$_6$H$_5$ | C$_6$H$_5$ | —(CH$_2$)$_3$— | 4-CH$_3$ | 2- |
| 10 | C$_6$H$_5$ | C$_6$H$_5$ | —(CH$_2$)$_3$— | 5-CH$_3$ | 2- |
| 11 | C$_6$H$_5$ | C$_6$H$_5$ | —(CH$_2$)$_3$— | 4-OCH$_3$ | 2- |
| 12 | C$_6$H$_5$ | C$_6$H$_5$ | —CH(CH$_3$)—CH$_2$—CH$_2$— | H | 2- |
| 13 | C$_6$H$_5$ | C$_6$H$_5$ | —CH$_2$—CH(CH$_3$)—CH$_2$— | H | 2- |
| 14 | C$_6$H$_5$ | C$_6$H$_5$ | —CH$_2$—CH$_2$—CH(CH$_3$)— | H | 2- |
| 15 | C$_6$H$_5$ | C$_6$H$_5$ | —(CH$_2$)$_4$— | H | 2- |
| 16 | C$_6$H$_5$ | C$_6$H$_5$ | —CH$_2$—CH=CH—CH$_2$— [(E) form] | H | 2- |
| 17 | C$_6$H$_5$ | C$_6$H$_5$ | —CH$_2$—CH=CH—CH$_2$— [(Z) form] | H | 2- |
| 18 | C$_6$H$_5$ | C$_6$H$_5$ | —CH$_2$—C≡C—CH$_2$— | H | 2- |
| 19 | C$_6$H$_5$ | C$_6$H$_5$ | —C(CH$_3$)$_2$—CH$_2$—CH$_2$— | H | 2- |
| 20 | C$_6$H$_5$ | C$_6$H$_5$ | —CH$_2$—C(CH$_3$)$_2$—CH$_2$— | H | 2- |
| 21 | C$_6$H$_5$ | C$_6$H$_5$ | —(CH$_2$)$_5$— | H | 2- |
| 22 | C$_6$H$_5$ | 4-FC$_6$H$_4$ | —(CH$_2$)$_3$— | H | 2- |
| 23 | C$_6$H$_5$ | 2,4-F$_2$C$_6$H$_3$ | —(CH$_2$)$_3$— | H | 2- |
| 24 | C$_6$H$_5$ | 2-ClC$_6$H$_4$ | —(CH$_2$)$_3$— | H | 2- |
| 25 | C$_6$H$_5$ | 4-ClC$_6$H$_4$ | —(CH$_2$)$_3$— | H | 2- |
| 26 | C$_6$H$_5$ | 3-CF$_3$C$_6$H$_4$ | —(CH$_2$)$_3$— | H | 2- |
| 27 | C$_6$H$_5$ | 4-CF$_3$C$_6$H$_4$ | —(CH$_2$)$_3$— | H | 2- |
| 28 | C$_6$H$_5$ | 2-CH$_3$C$_6$H$_4$ | —(CH$_2$)$_3$— | H | 2- |
| 29 | C$_6$H$_5$ | 3-CH$_3$C$_6$H$_4$ | —(CH$_2$)$_3$— | H | 2- |
| 30 | C$_6$H$_5$ | 4-CH$_3$C$_6$H$_4$ | —(CH$_2$)$_3$— | H | 2- |
| 31 | C$_6$H$_5$ | 4-C$_2$H$_5$C$_6$H$_4$ | —(CH$_2$)$_3$— | H | 2- |
| 32 | C$_6$H$_5$ | 4-CH$_3$OC$_6$H$_4$ | —(CH$_2$)$_3$— | H | 2- |
| 33 | 4-FC$_6$H$_4$ | 4-FC$_6$H$_4$ | —(CH$_2$)$_3$— | H | 2- |
| 34 | 4-ClC$_6$H$_4$ | 4-ClC$_6$H$_4$ | —(CH$_2$)$_3$— | H | 2- |
| 35 | 4-CH$_3$C$_6$H$_4$ | 4-CH$_3$C$_6$H$_4$ | —(CH$_2$)$_3$— | H | 2- |
| 36 | 4-CH$_3$OC$_6$H$_4$ | 4-CH$_3$OC$_6$H$_4$ | —(CH$_2$)$_3$— | H | 2- |
| 37 | cyclopentyl | C$_6$H$_5$ | —(CH$_2$)$_3$— | H | 2- |
| 38 | cyclohexyl | C$_6$H$_5$ | —(CH$_2$)$_3$— | H | 2- |
| 39 | 2-pyridyl | C$_6$H$_5$ | —(CH$_2$)$_3$— | H | 2- |

TABLE 2-continued

| | | | | | |
|---|---|---|---|---|---|
| 40 | 2-pyridyl | $C_6H_5$ | $-\underset{\underset{CH_3}{\vert}}{CH}-CH_2-CH_2-$ | H | 2- |
| 41 | 2-pyridyl | $C_6H_5$ | $-CH_2-CH=CH-CH_2-$ [(E) form] | H | 2- |
| 42 | 2-pyridyl | $C_6H_5$ | $-CH_2-CH=CH-CH_2-$ [(Z) form] | H | 2- |
| 43 | 2-pyridyl | $4-ClC_6H_4$ | $-(CH_2)_3-$ | H | 2- |
| 44 | 3-pyridyl | $C_6H_5$ | $-(CH_2)_3-$ | H | 2- |
| 45 | 3-pyridyl | $C_6H_5$ | $-\underset{\underset{CH_3}{\vert}}{CH}-CH_2-CH_2-$ | H | 2- |
| 46 | 3-pyridyl | $C_6H_5$ | $-CH_2-CH=CH-CH_2-$ [(E) form] | H | 2- |
| 47 | 3-pyridyl | $C_6H_5$ | $-CH_2-CH=CH-CH_2-$ [(Z) form] | H | 2- |
| 48 | 4-pyridyl | $C_6H_5$ | $-(CH_2)_3-$ | H | 2- |
| 49 | 4-pyridyl | $C_6H_5$ | $-CH_2-CH=CH-CH_2-$ [(E) form] | H | 2- |
| 50 | 4-pyridyl | $C_6H_5$ | $-CH_2-CH=CH-CH_2-$ [(Z) form] | H | 2- |
| 51 | 2-thienyl | $C_6H_5$ | $-(CH_2)_2-$ | H | 2- |
| 52 | 2-thienyl | $C_6H_5$ | $-(CH_2)_3-$ | H | 2- |
| 53 | 2-thienyl | $C_6H_5$ | $-\underset{\underset{CH_3}{\vert}}{CH}-CH_2-CH_2-$ | H | 2- |
| 54 | 2-thienyl | $C_6H_5$ | $-CH_2-CH_2-\underset{\underset{CH_3}{\vert}}{CH}-$ | H | 2- |
| 55 | 2-thienyl | $C_6H_5$ | $-(CH_2)_4-$ | H | 2- |
| 56 | 2-thienyl | $C_6H_5$ | $-CH_2-CH=CH-CH_2-$ [(E) form] | H | 2- |
| 57 | 2-thienyl | $C_6H_5$ | $-CH_2-CH=CH-CH_2-$ [(Z) form] | H | 2- |
| 58 | 2-thienyl | $C_6H_5$ | $-\overset{\overset{CH_3}{\vert}}{\underset{\underset{CH_3}{\vert}}{C}}-CH_2-CH_2-$ | H | 2- |
| 59 | 2-thienyl | $C_6H_5$ | $-CH_2-\overset{\overset{CH_3}{\vert}}{\underset{\underset{CH_3}{\vert}}{C}}-CH_2-$ | H | 2- |
| 60 | 3-thienyl | $C_6H_5$ | $-(CH_2)_2-$ | H | 2- |
| 61 | 3-thienyl | $C_6H_5$ | $-(CH_2)_3-$ | H | 2- |
| 62 | 3-thienyl | $C_6H_5$ | $-\underset{\underset{CH_3}{\vert}}{CH}-CH_2-CH_2-$ | H | 2- |
| 63 | 3-thienyl | $C_6H_5$ | $-(CH_2)_4-$ | H | 2- |
| 64 | 3-thienyl | $C_6H_5$ | $-CH_2-CH=CH-CH_2-$ [(E) form] | H | 2- |
| 65 | 3-thienyl | $C_6H_5$ | $-CH_2-CH=CH-CH_2-$ [(Z) form] | H | 2- |
| 66 | 3-thienyl | $C_6H_5$ | $-\overset{\overset{CH_3}{\vert}}{\underset{\underset{CH_3}{\vert}}{C}}-CH_2-CH_2-$ | H | 2- |
| 67 | 2-thienyl | 2-thienyl | $-(CH_2)_2-$ | H | 2- |
| 68 | 2-thienyl | 2-thienyl | $-(CH_2)_3-$ | H | 2- |
| 69 | 2-thienyl | 2-thienyl | $-\underset{\underset{CH_3}{\vert}}{CH}-CH_2-CH_2-$ | H | 2- |
| 70 | 2-thienyl | 2-thienyl | $-(CH_2)_4-$ | H | 2- |
| 71 | 2-thienyl | 2-thienyl | $-CH_2-CH=CH-CH_2-$ [(E) form] | H | 2- |
| 72 | 2-thienyl | 2-thienyl | $-CH_2-CH=CH-CH_2-$ [(Z) form] | H | 2- |
| 73 | 2-thienyl | 2-thienyl | $-\overset{\overset{CH_3}{\vert}}{\underset{\underset{CH_3}{\vert}}{C}}-CH_2-CH_2-$ | H | |
| 74 | 2-thienyl | 3-thienyl | $-(CH_2)_2-$ | H | 2- |
| 75 | 2-thienyl | 3-thienyl | $-(CH_2)_3-$ | H | 2- |

TABLE 2-continued

| | | | | | |
|---|---|---|---|---|---|
| 76 | 2-thienyl | 3-thienyl | —CH—CH$_2$—CH$_2$—<br>\|<br>CH$_3$ | H | 2- |
| 77 | 2-thienyl | 3-thienyl | —(CH$_2$)$_4$— | H | 2- |
| 78 | 2-thienyl | 3-thienyl | —CH$_2$—CH=CH—CH$_2$—[(E) form] | H | 2- |
| 79 | 2-thienyl | 3-thienyl | —CH$_2$—CH=CH—CH$_2$—[(Z) form] | H | 2- |
| 80 | 2-thienyl | 3-thienyl | CH$_3$<br>\|<br>—C—CH$_2$—CH$_2$—<br>\|<br>CH$_3$ | H | 2- |
| 81 | 3-thienyl | 3-thienyl | —(CH$_2$)$_2$— | H | 2- |
| 82 | 3-thienyl | 3-thienyl | —(CH$_2$)$_3$— | H | 2- |
| 83 | 3-thienyl | 3-thienyl | —CH—CH$_2$—CH$_2$—<br>\|<br>CH$_3$ | H | 2- |
| 84 | 3-thienyl | 3-thienyl | —(CH$_2$)$_4$— | H | 2- |
| 85 | 3-thienyl | 3-thienyl | —CH$_2$—CH=CH—CH$_2$—[(E) form] | H | 2- |
| 86 | 3-thienyl | 3-thienyl | —CH$_2$—CH=CH—CH$_2$—[(Z) form] | H | 2- |
| 87 | 3-thienyl | 3-thienyl | CH$_3$<br>\|<br>—C—CH$_2$—CH$_2$—<br>\|<br>CH$_3$ | H | 2- |
| 88 | 3-thienyl | 3-thienyl | CH$_3$<br>\|<br>—CH$_2$—C—CH$_2$—<br>\|<br>CH$_3$ | H | 2- |
| 89 | 2-pyridyl | 2-pyridyl | —(CH$_2$)$_2$— | H | 2- |
| 90 | 2-pyridyl | 2-pyridyl | —(CH$_2$)$_3$— | H | 2- |
| 91 | 2-pyridyl | 2-pyridyl | —CH—CH$_2$—CH$_2$—<br>\|<br>CH$_3$ | H | 2- |
| 92 | 2-pyridyl | 2-pyridyl | —(CH$_2$)$_4$— | H | 2- |
| 93 | 2-pyridyl | 2-pyridyl | —CH$_2$—CH=CH—CH$_2$—[(E) form] | H | 2- |
| 94 | 2-pyridyl | 2-pyridyl | —CH$_2$—CH=CH—CH$_2$—[(Z) form] | H | 2- |
| 95 | 2-pyridyl | 2-pyridyl | CH$_3$<br>\|<br>—C—CH$_2$—CH$_2$—<br>\|<br>CH$_3$ | H | 2- |
| 96 | 3-pyridyl | 3-pyridyl | —(CH$_2$)$_2$— | H | 2- |
| 97 | 3-pyridyl | 3-pyridyl | —(CH$_2$)$_3$— | H | 2- |
| 98 | 3-pyridyl | 3-pyridyl | —CH—CH$_2$—CH$_2$—<br>\|<br>CH$_3$ | H | 2- |
| 99 | 3-pyridyl | 3-pyridyl | —(CH$_2$)$_4$— | H | 2- |
| 100 | 3-pyridyl | 3-pyridyl | —CH$_2$—CH=CH—CH$_2$—[(E) form] | H | 2- |
| 101 | 3-pyridyl | 3-pyridyl | —CH$_2$—CH=CH—CH$_2$—[(Z) form] | H | 2- |
| 102 | 3-pyridyl | 3-pyridyl | CH$_3$<br>\|<br>—C—CH$_2$—CH$_2$—<br>\|<br>CH$_3$ | H | 2- |
| 103 | 2-pyridyl | 2-thienyl | —(CH$_2$)$_2$— | H | 2- |
| 104 | 2-pyridyl | 2-thienyl | —(CH$_2$)$_3$— | H | 2- |
| 105 | 2-pyridyl | 2-thienyl | —CH—CH$_2$—CH$_2$—<br>\|<br>CH$_3$ | H | 2- |
| 106 | 2-pyridyl | 2-thienyl | —(CH$_2$)$_4$— | H | 2- |
| 107 | 2-pyridyl | 2-thienyl | —CH$_2$—CH=CH—CH$_2$—[(E) form] | H | 2- |
| 108 | 2-pyridyl | 2-thienyl | —CH$_2$—CH=CH—CH$_2$—[(Z) form] | H | 2- |

TABLE 2-continued

| | | | | | |
|---|---|---|---|---|---|
| 109 | 2-pyridyl | 2-thienyl | −C(CH₃)(CH₃)−CH₂−CH₂− | H | 2- |
| 110 | 2-pyridyl | 3-thienyl | −(CH₂)₂− | H | 2- |
| 111 | 2-pyridyl | 3-thienyl | −(CH₂)₃− | H | 2- |
| 112 | 2-pyridyl | 3-thienyl | −CH(CH₃)−CH₂−CH₂− | H | 2- |
| 113 | 2-pyridyl | 3-thienyl | −(CH₂)₄− | H | 2- |
| 114 | 2-pyridyl | 3-thienyl | −CH₂−CH=CH−CH₂−[(E) form] | H | 2- |
| 115 | 2-pyridyl | 3-thienyl | −CH₂−CH=CH−CH₂−[(Z) form] | H | 2- |
| 116 | 2-pyridyl | 3-thienyl | −C(CH₃)(CH₃)−CH₂−CH₂− | H | 2- |
| 117 | 3-pyridyl | 2-thienyl | −(CH₂)₂− | H | 2- |
| 118 | 3-pyridyl | 2-thienyl | −(CH₂)₃− | H | 2- |
| 119 | 3-pyridyl | 2-thienyl | −CH(CH₃)−CH₂−CH₂− | H | 2- |
| 120 | 3-pyridyl | 2-thienyl | −(CH₂)₄− | H | 2- |
| 121 | 3-pyridyl | 2-thienyl | −CH₂−CH=CH−CH₂−[(E) form] | H | 2- |
| 122 | 3-pyridyl | 2-thienyl | −CH₂−CH=CH−CH₂−[(Z) form] | H | 2- |
| 123 | 3-pyridyl | 2-thienyl | −C(CH₃)(CH₃)−CH₂−CH₂− | H | 2- |
| 124 | 3-pyridyl | 3-thienyl | −(CH₂)₂− | H | 2- |
| 125 | 3-pyridyl | 3-thienyl | −(CH₂)₃− | H | 2- |
| 126 | 3-pyridyl | 3-thienyl | −CH(CH₃)−CH₂−CH₂− | H | 2- |
| 127 | 3-pyridyl | 3-thienyl | −(CH₂)₄− | H | 2- |
| 128 | 3-pyridyl | 3-thienyl | −CH₂−CH=CH−CH₂−[(E) form] | H | 2- |
| 129 | 3-pyridyl | 3-thienyl | −CH₂−CH=CH−CH₂−[(Z) form] | H | 2- |
| 130 | 3-pyridyl | 3-thienyl | −C(CH₃)(CH₃)−CH₂−CH₂− | H | 2- |
| 131 | 4-pyridyl | 2-thienyl | −(CH₂)₂− | H | 2- |
| 132 | 4-pyridyl | 2-thienyl | −(CH₂)₃− | H | 2- |
| 133 | 4-pyridyl | 2-thienyl | −CH(CH₃)−CH₂−CH₂− | H | 2- |
| 134 | 4-pyridyl | 2-thienyl | −(CH₂)₄− | H | 2- |
| 135 | 4-pyridyl | 2-thienyl | −CH₂−CH=CH−CH₂−[(E) form] | H | 2- |
| 136 | 4-pyridyl | 2-thienyl | −CH₂−CH=CH−CH₂−[(Z) form] | H | 2- |
| 137 | 4-pyridyl | 2-thienyl | −C(CH₃)(CH₃)−CH₂−CH₂− | H | 2- |
| 138 | 4-pyridyl | 3-thienyl | −(CH₂)₂− | H | 2- |
| 139 | 4-pyridyl | 3-thienyl | −(CH₂)₃− | H | 2- |
| 140 | 4-pyridyl | 3-thienyl | −CH(CH₃)−CH₂−CH₂− | H | 2- |
| 141 | 4-pyridyl | 3-thienyl | −(CH₂)₄− | H | 2- |
| 142 | 4-pyridyl | 3-thienyl | −CH₂−CH=CH−CH₂−[(E) form] | H | 2- |

TABLE 2-continued
| 143 | 4-pyridyl | 3-thienyl | $-CH_2-CH=CH-CH_2-$ [(Z) form] | H | 2- |
| 144 | 4-pyridyl | 3-thienyl | $\begin{array}{c} CH_3 \\ | \\ -C-CH_2-CH_2- \\ | \\ CH_3 \end{array}$ | H | 2- |
The process for preparing the piperidine derivatives having the formula (I), (II) or (III) are explained below.
The piperidine derivatives having the formula (I), (II) or (III) can be prepared according to the following processes.
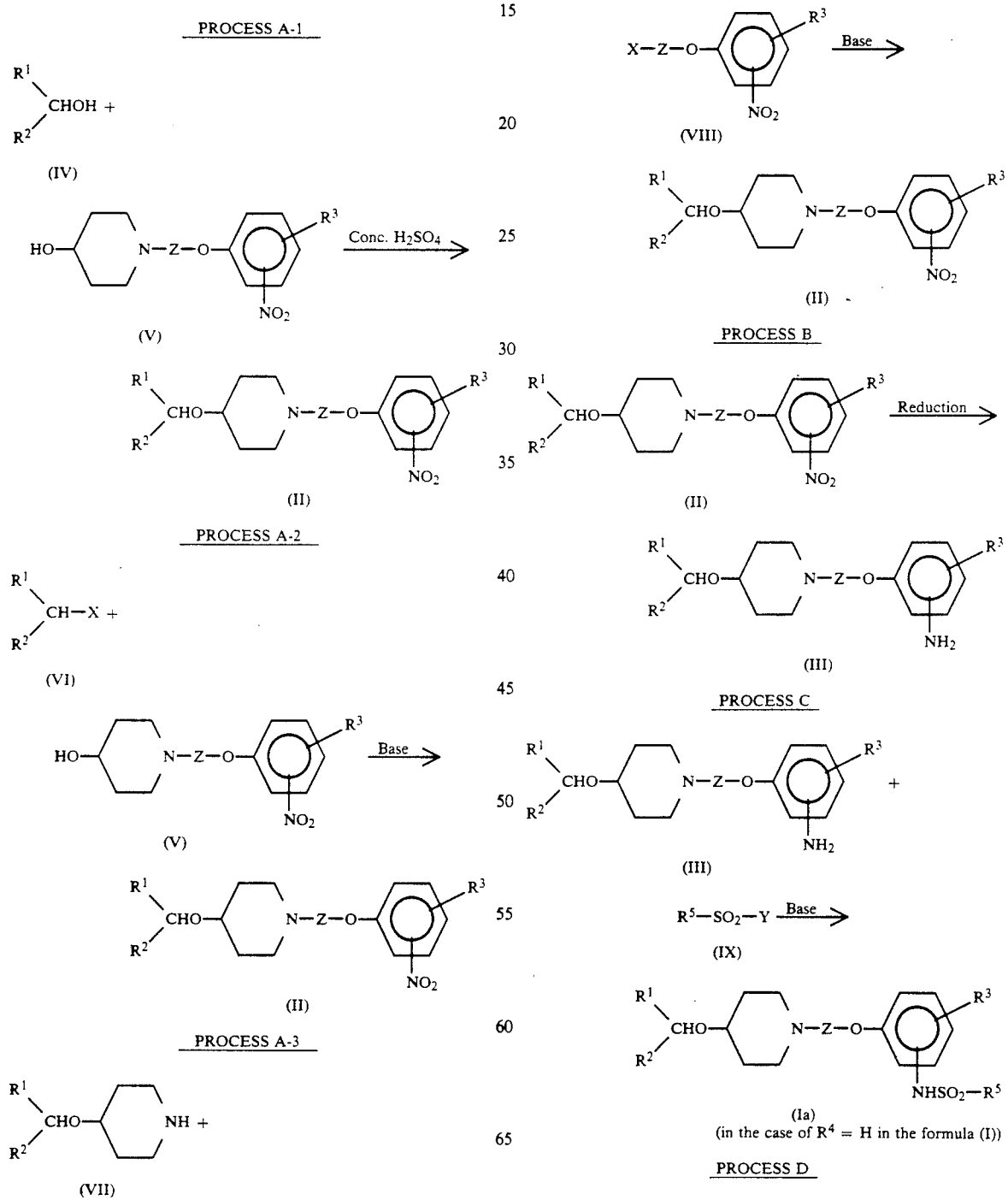

-continued

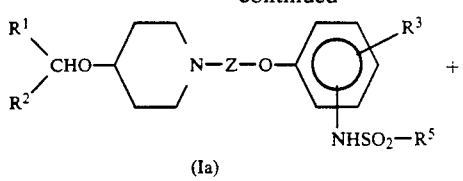

(Ia)

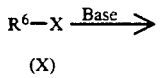

(X)

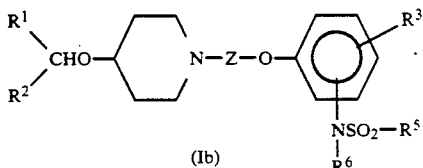

(Ib)

(in the case of $R^4 = C_{1-4}$ alkyl in the formula (I))

In the above-mentioned formulae, $R^1$, $R^2$, $R^3$, $R^5$ and Z are the same as above-defined, $R^6$ is a $C_{1-4}$ alkyl group, X is chlorine, bromine or iodine and Y is chlorine or $R^5-SO_2-O-$ where in $R^5$ is the same as above-defined.

The above-mentioned processes are described further detailedly in the followings.

PROCESS A-1

The desired compound having the formula (II) can be prepared by dehydrating reaction of the compound having the formula (IV) and the compound having the formula (V) in the presence of concentrated sulfuric acid in an inactive solvent.

The inactive solvents usable in the present reaction are not particularly limited, if the solvents do not considerably inhibit this type of reaction. As such solvents, for example, benzene, toluene, xylene and the like are preferable.

In the present reaction, 0.5 to 2 moles of the compound having the formula (V) is used per mole of the compound having the formula (IV).

Although concentrated sulfuric acid is generally used in an excess amount, 2 to 20 moles of concentrated sulfuric acid is preferably used per mole of the compound having the formula (IV).

The reaction temperature can be suitably selected in the range of from 50° C. to the boiling point of the used solvent. The reaction time can be suitably selected in the range of from 1 to 10 hours.

PROCESS A-2

The desired compound having the formula (II) can be prepared by reacting the compound having the formula (VI) and the compound having the formula (V) in the presence of a base in an inactive solvent.

The inactive solvents usable in the present reaction are not particularly limited, if the solvents do not considerably inhibit this type of reaction. As such solvents, for example, methyl ethyl ketone, methyl isobutyl ketone, tetrahydrofuran, 1,2-dichloroethane, benzene, toluene, dimethylformamide and the like are preferable.

Bases usable in the present reaction are not particularly limited, if they usually act as bases. As such bases, for example, inorganic bases such as sodium carbonate, potassium carbonate, sodium bicarbonate and potassium bicarbonate, organic bases of tertiary amine such as triethylamine, N,N-diisopropylethylamine and pyridine and the like are preferable.

In the present reaction, 0.5 to 2 moles of the compound having the formula (V) is used per mole of the compound having the formula (VI).

The base is used in an amount of at least equivalent mole, generally 1 to 5 moles per mole of the compound having the formula (VI).

The reaction temperature can be suitably selected in the range of from 60° C. to the boiling point of the used solvent. The reaction time can be suitably selected in the range of from 0.5 to 100 hours.

PROCESS A-3

The desired compound having the formula (II) can be prepared by reacting the compound having the formula (VII) and the compound having the formula (VIII) in the presence of a base in an inactive solvent.

The inactive solvents usable in the present reaction are not particularly limited, if the solvents do not considerably inhibit this type of reaction. As such solvents, for example, methyl alcohol, ethyl alcohol, propyl alcohol, methyl ethyl ketone, methyl isobutyl ketone, tetrahydrofuran, dichloromethane, 1,2-dichloroethane, benzene, toluene, dimethylformamide and the like are preferable.

As bases usable in the present reaction, those exemplified in the explanation of the PROCESS A-2 can be exemplified.

In the present reaction, 0.5 to 2 moles of the compound having the formula (VIII) is used per mole of the compound having the formula (VII).

The base is used in an amount of at least equivalent mole, generally 1 to 5 moles per mole of the compound having the formula (VII).

The reaction temperature can be suitably selected in the range of from room temperature to the boiling point of the used solvent. The reaction time can be suitably selected in the range of from 0.5 to 100 hours.

PROCESS B

The desired compound having the formula (III) can be prepared by reducing the compound having the formula (II) in an inactive solvent.

In the present reaction, although any common means for reduction of nitro group into amino group can be used, the reaction are preferably carried out with a metal such as tin, zinc or iron at the pH of from neutral to weak acid. For example, a process using the combination of zinc and calcium chloride or the combination of iron and acetic acid can be exemplified.

The inactive solvents usable in the present reaction are not particularly limited, if the solvents do not considerably inhibit this type of reaction. As such solvents, for example, water, methyl alcohol, ethyl alcohol, propyl alcohol, tetrahydrofuran, dioxane, an aqueous mixture thereof and the like are preferable.

The reaction temperature can be suitably selected in the range of from room temperature to the boiling point of the used solvent. The reaction time can be suitably selected in the range of from 0.5 to 10 hours.

PROCESS C

The desired compound having the formula (Ia) can be prepared by reacting the compound having the formula (III) and the compound having the formula (IX) in the presence of a base in an inactive solvent.

The inactive solvents usable in the present reaction are not particularly limited, if the solvents do not considerably inhibit this type of reaction. As such solvents, for example, acetone, methyl ethyl ketone, tetrahydrofuran, dichloromethane, chloroform, 1,2-dichloroethane, benzene, pyridine and the like are preferable.

Bases usable in the present reaction are not particularly limited, if they usually act as bases. As such bases, for example, organic bases of tertiary amine such as triethylamine and pyridine are preferable.

In the present reaction, 1 to 1.5 moles of the compound having the formula (IX) is used per mole of the compound having the formula (III).

The base is used in an amount of at least equivalent mole per mole of the compound having the formula (III).

The reaction is usually carried out under cooling or at room temperature. The reaction time can be suitably selected in the range of from a few minutes to 10 hours.

PROCESS D

The desired compound having the formula (Ib) can be prepared by reacting the compound having the formula (Ia) and the compound having the formula (X) in the presence of a base in an inactive solvent.

The inactive solvents usable in the present reaction are not particularly limited, if the solvents do not considerably inhibit this type of reaction. As such solvents, for example, methyl alcohol, ethyl alcohol, propyl alcohol, tetrahydrofuran, dimethylformamide and the like are preferable.

As bases usable in the present reaction, for example, inorganic bases such as sodium hydride, sodium amide and an alcoholate of alkaline metal such as sodium or potassium are preferable.

In the present reaction, 1 to 2 moles of the compound having the formula (X) is used per mole of the compound having the formula (Ia).

The base is used in an amount of 1 to 1.5 moles per mole of the compound having the formula (Ia).

The reaction temperature can be suitably selected in the range of from 0° C. to the boiling point of the used solvent. The reaction time can be suitably selected in the range of from 0.5 to 10 hours.

The desired compounds prepared according to the above-mentioned processes A-1-D can be isolated and purified by a usual method.

The desired compounds prepared according to the process A-2, A-3, B and C may be obtained in the form of salts with hydrohalogenic acid such as hydrochloric acid, hydrobromic acid or hydroiodic acid, depending upon the kinds of the reactants, reaction conditions or the conditions of the isolation or purification.

In the above-mentioned case, an inorganic base such as sodium carbonate, potassium carbonate, sodium hydroxide or potassium hydroxide or an aqueous solution thereof may be added to carry out dehydrohalogenation, thereby a desired free compound being obtained.

Thus obtained piperidine derivative having the formula (I) has both of the inhibition activity of mediator release in allergic reaction and antihistaminic activity. Therefore the piperidine derivative of the present invention having the formula (I) has an excellent antiallergic activity and so shows excellent effects for prevention and treatment of various allergic diseases such as allergic asthma, allergic dermatitis, allergic rhinitis, allergic gastroenteritis, vernal conjunctivitis and allergic conjunctivitis.

Furthermore, the piperidince derivative of the present invention having the formula (I) has also excellent therapeutic activity for ischemic heart disease such as stenocardia and myocardial infarction.

The piperidine derivative of the present invention having the formula (I) can be used as it is or in various pharmaceutical preparation forms according to known pharmaceutical preparation process. The piperidine derivative of the present invention having the formula (I) can be used in pharmaceutical preparations for oral administration such as tablets, capsules, granule, powder and syrup or pharmaceutical preparations for parenteral administration such as injection, collunarium, eye drops, ointment and suppository.

Although the dosage of the compound of the present invention having the formula (I) is different according to the sympton, age or body weight of a patient, treatment effect, or method or period of administration, a suitable dosage is generally 0.1 to 200 mg in case of oral administration on the basis of the compound (I) of the present invention per day for adults.

The piperidine derivative having the formula (II) or (III) is useful as an intermediate for preparing the compound having the formula (I) and has also excellent therapeutic activity for ischemic heart disease such as stenocardia and myocardial infarction.

The present invention is more specifically described and explained by means of the following Examples. It is to be understood that the present invention is not limited to the Examples, and various changes and modifications may be made in the invention without departing from the spirit and scope thereof.

EXAMPLE 1

Preparation of
4-diphenylmethoxy-1-[3-(2-methanesulfonylaminophenoxy)propyl]piperidine

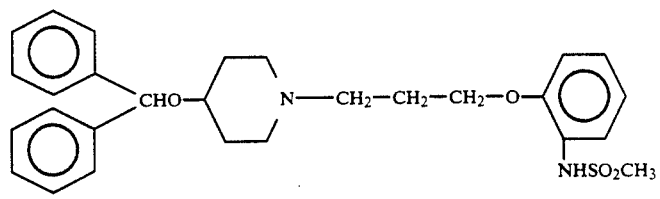

(a) Into 270 ml of methyl isobutyl ketone were dissolved 32.1 g of diphenylmethyl bromide, 28.0 g of 4-hydroxy-1-[3-(2-nitrophenoxy)propyl]piperidine and 30.4 g of triethylamine. The resultant solution was heated under reflux with stirring for 15 hours. After cooling, the reaction solution was washed with water, and the solvent was removed under reduced pressure. The residue was eluted with methanol-chloroform (1:50) by silica gel column chromatography to give 33.9 g of oily 4-diphenylmethoxy-1-[3-(2-nitrophenoxy)-propyl]piperidine.

¹H-NMR (CDCl₃) δ:1.63-2.21 (8H,m), 2.51 (2H,t), 2.77 (2H,m), 3.43 (1H,m), 4.15 (2H,t), 5.52 (1H,s), 6.95-7.54 (13H,m), 7.81 (1H,d)

(b) A mixture of 20.0 g of the nitro compound obtained in (a), 58.0 g of zinc powder, 9.0 g of calcium chloride, 600 ml of ethanol and 160 ml of water was heated under reflux with stirring for 2 hours. The reaction mixture was filtered, and the filtrate was concentrated. Water was added to the concentrate, and the mixture was extracted with ethyl acetate. The resultant organic layer was washed with water, and the solvent was removed under reduced pressure to give 16.1 g of 4-diphenylmethoxy-1-[3-(2-aminophenoxy)propyl]-piperidine. m.p.: 86°-88° C. (recrystallized from n-hexane)

¹H-NMR (CDCl₃) δ:1.63-2.07 (6H,m), 2.13 (2H,br t), 2.50 (2H,t), 2.77 (2H,m), 3.44 (1H,m), 3.83 (2H,br s), 4.02 (2H,t), 5.52 (1H,s), 6.62-6.83 (4H,m), 7.18-7.42 (10H,m)

(c) Into 25 ml of pyridine was dissolved 2.5 g of the amino compound obtained in (b). To the resultant solution was added dropwise 0.83 g of methanesulfonyl chloride at room temperature, and the mixture was stirred for 1 hour. The reaction solution was poured into ice water, and extracted with ethyl acetate. The extract was washed with water, and ethyl acetate was removed. The residue was eluted with methanol-chloroform (1:50) by silica gel column chromatography to give 2.1 g of the desired compound.

m.p.: 106°-107° C. (recrystallized from ethanol)

¹H-NMR (CDCl₃) δ:1.66-1.82 (2H,m), 1.84-2.04 (4H,m), 2.17 (2H,br t), 2.48 (2H,t), 2.76 (2H,m), 2.94 (3H,s), 3.46 (1H,m), 4.08 (2H,t), 5.52 (1H,s), 6.89-7.55 (14H,m)

EXAMPLE 2

Preparation of 4-diphenylmethoxy-1-[3-(2-methanesulfonylamino-phenoxy)propyl]piperidine hydrochloride.

Into 20 ml of ethanol was dissolved 0.50 g of 4-diphenylmethoxy-1-[3-(2-methanesulfonylamino-phenoxy)propyl]piperidine obtained in Example 1 (c), and 0.13 ml of 36% HCl was added dropwise to the resultant solution with cooling and stirring. The mixture was dried under reduced pressure to form a solid. The residue was recrystallized from isopropyl alcohol to give 0.43 g of the desired compound.

m.p.: 180°-182° C.

EXAMPLE 3

Preparation of 4-diphenylmethoxy-1-[3-(2-methanesulfonylamino-phenoxy)propyl]piperidine fumarate Into 40 ml of ethanol were dissolved at first 1.0 g of 4-diphenylmethoxy-1-[3-(2-methanesulfonylamino-phenoxy)propyl]-piperidine obtained in Example 1 (c) and then 0.234 g of fumaric acid. The mixture was dried under reduced pressure to form a solid. The residue was recrystallized from isopropyl alcohol to give 0.98 g of the desired compound.

m.p.: 179.5°-181° C.

EXAMPLE 4

Preparation of 4-diphenylmethoxy-1-[3-(2-ethanesulfonylamino-phenoxy)propyl]piperidine

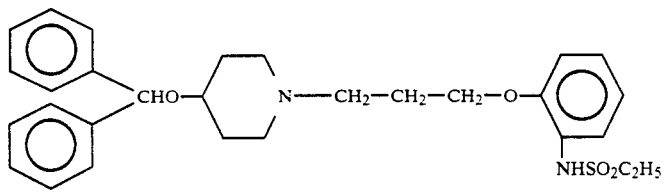

The procedure of Example 1 (c) was repeated except for using 4-diphenylmethoxy-1-[3-(2-aminophenoxy)-propyl]piperidine obtained in Example 1 (b) and ethanesulfonyl chloride instead of 4-diphenylmethoxy-1-[3-(2-aminophenoxy)propyl]piperidine and methanesulfonyl chloride to give the desired compound.

¹H-NMR (CDCl₃) δ:1.32 (3H,t), 1.67-1.82 (2H,m), 1.83-2.04 (4H,m), 2.07-2.26 (2H,m), 2.47 (2H,t), 2.75 (2H,m), 3.06 (2H,q), 3.46 (1H,m), 4.08 (2H,t), 5.52 (1H,s), 6.88-7.58 (14H,m)

EXAMPLE 5

Preparation of 4-diphenylmethoxy-1-[3-[2-(2-thiophene)sulfonylaminophenoxy]propyl]piperidine

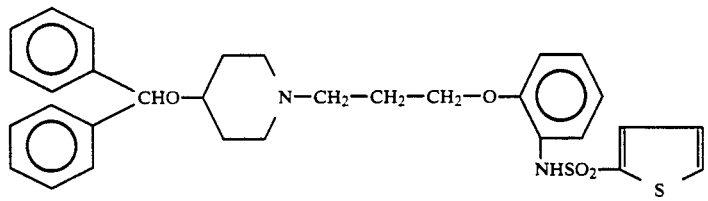

The procedure of Example 1 (c) was repeated except for using 4-diphenylmethoxy-1-[3-(2-aminophenoxy)-propyl]piperidine obtained in Example 1 (b) and 2-thiophenesulfonyl chloride instead of 4-diphenylmethoxy-1-[3-(2-aminophenoxy)propyl]piperidine and methanesulfonyl chloride to give the desired compound.

m.p.: 119°-120° C. (recrystallized from ethanol)

¹H-NMR (CDCl₃) δ:1.68-1.98 (6H,m), 2.26 (2H,m), 2.43 (2H,t), 2.76 (2H,m), 3.48 (1H,m), 3.86 (2H,t), 5.52 (1H,s), 6.76-7.63 (17H,m)

EXAMPLE 6

Preparation of 4-diphenylmethoxy-1-[3-(2-benzenesulfonylaminophenoxy)propyl]piperidine

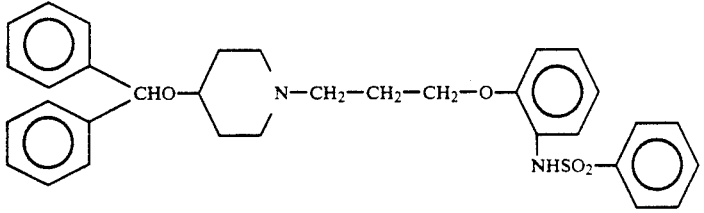

Into 25 ml of pyridine was dissolved 1.0 g of 4-diphenylmethoxy-1-[3-(2-aminophenoxy)propyl]piperidine obtained in Example 1 (b), and 0.51 g of benzenesulfonyl chloride was added dropwise to the resultant solution at room temperature, followed by stirring for 30 minutes. The reaction solution was poured into ice water, and extracted with chloroform. The extract was washed with water, and chloroform was removed. The residue was eluted with ethyl acetate-chloroform (1:1) by silica gel column chromatography to give 0.79 g of the desired compound.

m.p.: 131°–132° C.
$^1$H-NMR (CDCl$_3$) δ:1.66–1.98 (6H,m), 2.15 (2H,br t), 2.35 (2H,t), 2.73 (2H,m), 3.46 (1H,m), 3.78 (2H,t), 5.53 (1H,s), 6.70–7.77 (19H,m)

EXAMPLE 7

Preparation of 4-diphenylmethoxy-1-[3-(2-trifluoromethanesulfonylaminophenoxy)propyl]piperidine

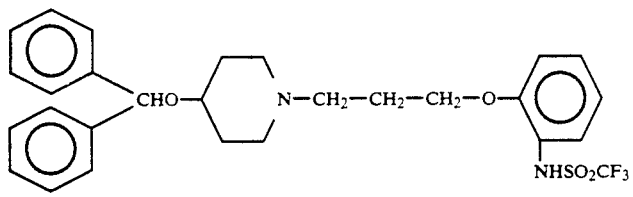

Into 25 ml of dichloromethane were dissolved 1.0 g of 4-diphenylmethoxy-1-[3-(2-aminophenoxy)propyl]piperidine obtained in Example 1 (b) and 0.32 g of triethylamine, and 0.71 g of trifluoromethanesulfonic anhydride was added dropwise to the resultant solution at −78° C., followed by stirring for 1 hour. The reaction solution was washed with water, and the solvent was removed under reduced pressure. The residue was recrystallized from dichloromethane-ethyl acetate to give 0.98 g of the desired compound.

m.p.: >190° C.
$^1$H-NMR (CDCl$_3$) δ:1.89–2.20 (6H,m), 3.16 (2H,m), 3.29 (2H,t), 3.75 (3H, br s), 4.11 (2H,t), 5.42 (1H,s), 6.78–7.04 (3H,m), 7.18–7.38 (10H,m), 7.57 (1H,dd)

EXAMPLE 8

Preparation of 4-diphenylmethoxy-1-[3-(2-N-methyl-N-methanesulfonylaminophenoxy)propyl]piperidine

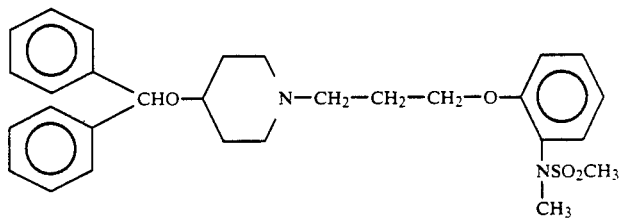

Into 20 ml of N,N-dimethylformamide was dissolved 1.0 g of 4-diphenylmethoxy-1-[3-(2-methanesulfonylaminophenoxy)propyl]piperidine obtained in Example 1 (c), and 0.14 g of sodium hydride (60%, in oil) was added to the resultant solution with ice cooling, followed by stirring for 30 minutes. Then 0.40 g of methyl iodide was added dropwise to the mixture, and the mixture was stirred at room temperature for 1 hour. The reaction solution was poured into ice water, and extracted with ethyl acetate. The extract was washed with water, and the solvent was removed. The residue was eluted with ethyl acetate by silica gel column chromatography to give 0.81 g of the desired compound.

$^1$H-NMR (CDCl$_3$) δ:1.68–1.84 (2H,m), 1.87–2.09 (4H,m), 2.20 (2H,m), 2.53 (2H,t), 2.78 (2H,m), 2.92 (3H,s), 3.25 (3H,s), 3.47 (1H,m), 4.08 (2H,t), 5.52 (1H,s), 6.91–7.00 (2H,m), 7.20–7.41 (12H,m)

EXAMPLE 9

Preparation of
4-diphenylmethoxy-1-[2-(2-methanesulfonylaminophenoxy)ethyl]piperidine

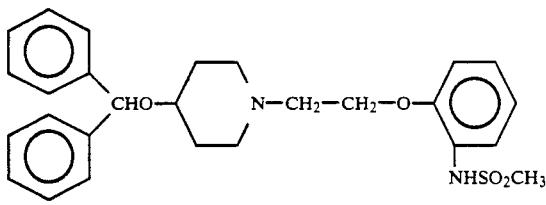

(a) The procedure of Example 1 (a) was repeated except for using diphenylmethyl bromide and 4-hydroxy-1-[2-(2-nitrophenoxy)ethyl]piperidine instead of diphenylmethyl bromide and 4-hydroxy-1-[3-(2-nitrophenoxy)propyl]piperidine to give oily 4-diphenylmethoxy-1-[2-(2-nitrophenoxy)ethyl]piperidine.

$^1$H-NMR (CDCl$_3$) δ:1.65–1.80 (2H,m), 1.83–1.97 (2H,m), 2.31 (2H,m), 2.78–2.93 (4H,m), 3.44 (1H,m), 4.21 (2H,t), 5.52 (1H,s), 6.96–7.53 (13H,m), 7.81 (1H,dd)

(b) The procedure of Example 1 (b) was repeated except for using the nitro compound obtained in (a) instead of 4-diphenylmethoxy-1-[3-(2-nitrophenoxy)propyl]piperidine to give 4-diphenylmethoxy-1-[2-(2-aminophenoxy)ethyl]piperidine.

(c) The procedure of Example 1 (c) was repeated except for using the amino compound obtained in (b) instead of 4-diphenylmethoxy-1-[3-(2-aminophenoxy)propyl]piperidine to give the desired compound.

$^1$H-NMR (CDCl$_3$) δ:1.70–2.02 (4H,m), 2.47 (2H,m), 2.70–2.92 (4H,m), 3.15 (3H,s), 3.53 (1H,m), 4.18 (2H,t), 5.48 (1H,s), 6.93–7.05 (2H,m), 7.18–7.44 (12H,m)

EXAMPLE 10

Preparation of
4-diphenylmethoxy-1-[3-(3-methanesulfonylaminophenoxy)propyl]piperidine

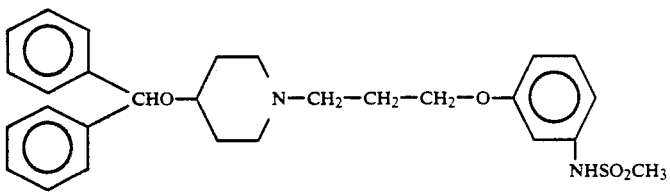

(a) The procedure of Example 1 (a) was repeated except for using diphenylmethyl bromide and 4-hydroxy-1-[3-(3-nitrophenoxy)propyl]piperidine instead of diphenylmethyl bromide and 4-hydroxy-1-[3-(2-nitrophenoxy)propyl]piperidine to give oily 4-diphenylmethoxy-1-[3-(3-nitrophenoxy)propyl]piperidine.

(b) The procedure of Example 1 (b) was repeated except for using the nitro compound obtained in (a) instead of 4-diphenylmethoxy-1-[3-(2-nitrophenoxy)propyl]piperidine to give 4-diphenylmethoxy-1-[3-(3-aminophenoxy)propyl]piperidine.

(c) The procedure of Example 1 (c) was repeated except for using the amino compound obtained in (b) instead of 4-diphenylmethoxy-1-[3-(2-aminophenoxy)propyl]piperidine to give the desired compound.
m.p.: 90°–95.5° C.

$^1$H-NMR (CDCl$_3$) δ:1.90–2.06 (2H,m), 2.16–2.37 (4H,m), 2.97 (3H,s), 2.93–3.21 (6H,m), 3.73 (1H,m), 3.98 (2H,t), 5.45 (1H,s), 6.61 (1H,d), 6.88–6.98 (2H,m) 7.11–7.39 (11H,m)

EXAMPLE 11

Preparation of
4-diphenylmethoxy-1-[3-(4-methanesulfonylaminophenoxy)propyl]piperidine

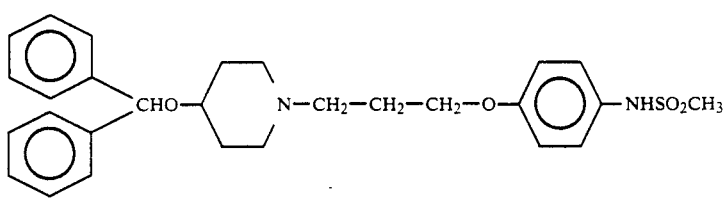

(a) The procedure of Example 1 (a) was repeated except for using diphenylmethyl bromide and 4-hydroxy-1-[3-(4-nitrophenoxy)propyl]piperidine instead of diphenylmethyl bromide and 4-hydroxy-1-[3-(2-nitrophenoxy)propyl]piperidine to give oily 4-diphenylmethoxy-1-[3-(4-nitrophenoxy)propyl]piperidine.

$^1$H-NMR (CDCl$_3$) δ:1.64–1.81 (2H,m), 1.82–2.04 (4H,m), 2.15 (2H,br t), 2.48 (2H,t), 2.75 (2H,m), 3.45 (1H,m), 4.09 (2H,t), 5.52 (1H,s), 6.93 (2H,d), 7.19–7.40 (10H,m), 8.17 (2H,d)

(b) The procedure of Example 1 (b) was repeated except for using the nitro compound obtained in (a) instead of 4-diphenylmethoxy-1-[3-(2-nitrophenoxy)propyl]piperidine to give 4-diphenylmethoxy-1-[3-(4-aminophenoxy)propyl]piperidine.

$^1$H-NMR (CDCl$_3$) δ:1.63–1.80 (2H,m), 1.82–1.98 (4H,m), 2.13 (2H,br t), 2.46 (2H,t), 2.76 (2H,m), 3.26–3.50 (3H,m), 3.91 (2H,t), 5.51 (1H,s), 6.61 (2H,d), 6.72 (2H,d), 7.19–7.40 (10H,m)

(c) The procedure of Example 1 (c) was repeated except for using the amino compound obtained in (b) instead of 4-diphenylmethoxy-1-[3-(2-aminophenoxy)propyl]piperidine to give the desired compound.
m.p.: 41°–43° C.

$^1$H-NMR (CDCl$_3$) δ:1.70–1.86 (2H,m), 1.88–2.07 (4H,m), 2.30 (2H,m), 2.56 (2H,t), 2.81 (2H,m), 2.92 (3H,s), 3.49 (1H,m), 3.97 (2H,t), 5.51 (1H,s), 6.85 (2H,d), 7.15–7.43 (12H,m)

EXAMPLE 12

Preparation of 4-diphenylmethoxy-1-[3-(5-fluoro-2-methanesulfonylaminophenoxy)propyl]piperidine

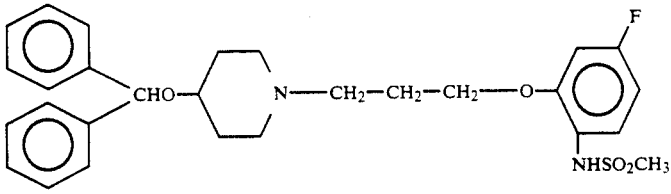

(a) The procedure of Example 1 (a) was repeated except for using diphenylmethyl bromide and 4-hydroxy-1-[3-(5-fluoro-2-nitrophenoxy)propyl]piperidine instead of diphenylmethyl bromide and 4-hydroxy-1-[3-(2-nitrophenoxy)propyl]piperidine to give oily 4-diphenylmethoxy1-[3-(5-fluoro-2-nitrophenoxy)propyl]piperidine.

(b) The procedure of Example 1 (b) was repeated except for using the nitro compound obtained in (a) instead of 4-diphenylmethoxy-1-[3-(2-nitrophenoxy)propyl]piperidine to give 4-diphenylmethoxy-1-[3-(2-amino-5-fluorophenoxy)propyl]piperidine.

(c) The procedure of Example 1 (c) was repeated except for using the amino compound obtained in (b) instead of 4-diphenylmethoxy-1-[3-(2-aminophenoxy)propyl]piperidine to give the desired compound.

m.p.: 52°–56° C.

$^1$H-NMR (CDCl$_3$) δ:1.64–2.05 (6H,m), 2.17 (2H,m), 2.48 (2H,t), 2.75 (2H,m), 2.85 (3H,s), 3.62 (1H,m), 4.03 (2H,t), 5.51 (1H,s), 6.44–6.53 (2H,m), 7.20–7.41 (11H,m)

EXAMPLE 13

Preparation of 4-diphenylmethoxy-1-[3-(2-methanesulfonylamino-3-methylphenoxy)propyl]piperidine

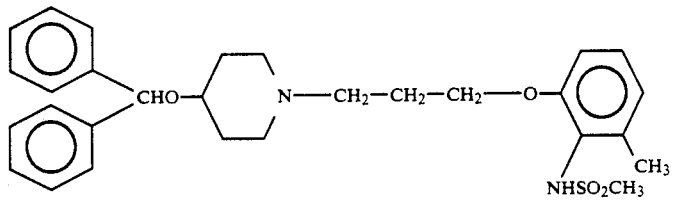

(a) The procedure of Example 1 (a) was repeated except for using diphenylmethyl bromide and 4-hydroxy-1-[3-(3-methyl-2-nitrophenoxy)propyl]piperidine instead of diphenylmethyl bromide and 4-hydroxy-1-[3-(2-nitrophenoxy)propyl]piperidine to give oily 4-diphenylmethoxy-1-[3-(3-methyl-2-nitrophenoxy)propyl]piperidine.

$^1$H-NMR (CDCl$_3$) δ:1.72–1.88 (2H,m), 1.95–2.13 (4H,m), 2.29 (3H,s), 2.45 (2H,m), 2.63 (2H,br t), 2.88 (2H,m), 3.55 (1H,m), 4.12 (2H,t), 5.49 (1H,s), 6.79–6.89 (2H,m), 7.17–7.37 (11H,m)

(b) The procedure of Example 1 (b) was repeated except for using the nitro compound obtained in (a) instead of 4-diphenylmethoxy-1-[3-(2-nitrophenoxy)propyl]piperidine to give 4-diphenylmethoxy-1-[3-(2-amino-3-methylphenoxy)propyl]piperidine.

(c) The procedure of Example 1 (c) was repeated except for using the amino compound obtained in (b) instead of 4-diphenylmethoxy-1-[3-(2-aminophenoxy)propyl]piperidine to give the desired compound.

m.p.: 131.5°–132.5° C. (recrystallized from dichloromethane-n-hexane)

$^1$H-NMR (CDCl$_3$) δ:1.64–1.80 (2H,m), 1.82–2.01 (4H,m), 2.16 (2H,br t), 2.40–2.50 (5H,m), 2.73 (2H,m), 2.94 (3H,s), 3.46 (1H,m), 4.07 (2H,t), 5.52 (1H,s), 6.74–6.91 (2H,m), 7.10–7.38 (11H,m)

EXAMPLE 14

Preparation of 4-diphenylmethoxy-1-[3-(2-methanesulfonylamino-4-methylphenoxy)propyl]piperidine

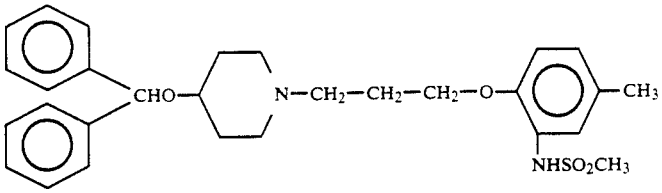

(a) The procedure of Example 1 (a) was repeated except for using diphenylmethyl bromide and 4-hydroxy-1-[3-(4-methyl-2-nitrophenoxy)propyl]piperidine instead of diphenylmethyl bromide and 4-hydroxy-1-[3-(2-nitrophenoxy)propyl]piperidine to give oily 4-diphenylmethoxy-1-[3-(4-methyl-2-nitrophenoxy)propyl]piperidine.

$^1$H-NMR (CDCl$_3$) δ:1.65–1.82 (2H,m), 1.86–2.09 (4H,m), 2.23 (2H,m), 2.33 (3H,s), 2.57 (2H,br t), 2.81

(2H,m), 3.47 (1H,m), 4.13 (2H,t), 5.51 (1H,s), 6.93–7.65 (13H,m)

(b) The procedure of Example 1 (b) was repeated except for using the nitro compound obtained in (a) instead of 4-diphenylmethoxy-1-[3-(2-nitrophenoxy)propyl]piperidine to give 4-diphenylmethoxy-1-[3-(2-amino-4-methylphenoxy)propyl]piperidine.

(c) The procedure of Example 1 (c) was repeated except for using the amino compound obtained in (b) instead of 4-diphenylmethoxy-1-[3-(2-aminophenoxy)propyl]piperidine to give the desired compound.

$^1$H-NMR (CDCl$_3$) δ:1.65–1.81 (2H,m), 1.83–2.01 (4H,m), 2.16 (2H,br t), 2.29 (3H,s), 2.47 (2H, t), 2.76 (2H,m), 2.93 (3H,s), 3.46 (1H,m), 4.04 (2H,t), 5.52 (1H,s), 6.76–6.93 (2H,m), 7.12–7.38 (11H,m)

EXAMPLE 15

Preparation of 4-diphenylmethoxy-1-[3-(2-methanesulfonylamino-5-methylphenoxy)propyl]piperidine

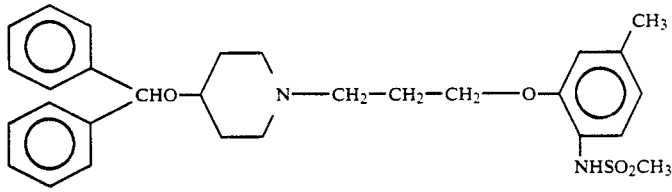

(a) The procedure of Example 1 (a) was repeated except for using diphenylmethyl bromide and 4-hydroxy-1-[3-(5-methyl-2-nitrophenoxy)propyl]piperidine instead of diphenylmethyl bromide and 4-hydroxy-1-[3-(2-nitrophenoxy)propyl]piperidine to give oily 4-diphenylmethoxy-1-[3-(5-methyl-2-nitrophenoxy)propyl]piperidine.

$^1$H-NMR (CDCl$_3$) δ:1.80–1.96 (2H,m), 2.08–2.33 (4H,m), 2.40 (3H,s), 2.75 (2H,m), 2.89 (2H,br t), 3.02 (2H,m), 3.65 (1H,m), 4.19 (2H,t), 5.48 (1H,s), 6.78–6.89 (2H,m), 7.20–7.38 (10H,m) 7.79 (1H,d)

(b) The procedure of Example 1 (b) was repeated except for using the nitro compound obtained in (a) instead of 4-diphenylmethoxy-1-[3-(2-nitrophenoxy)propyl]piperidine to give 4-diphenylmethoxy-1-[3-(2-amino-5-methylphenoxy)propyl]piperidine.

(c) The procedure of Example 1 (c) was repeated except for using the amino compound obtained in (b) instead of 4-diphenylmethoxy-1-[3-(2-aminophenoxy)propyl]piperidine to give the desired compound.

$^1$H-NMR (CDCl$_3$) δ:1.65–1.81 (2H,m), 1.83–2.02 (4H,m), 2.17 (2H,br t), 2.32 (3H,s), 2.47 (2H,t), 2.76 (2H,m), 2.90 (3H,s), 3.46 (1H,m), 4.06 (2H,t), 5.52 (1H,s), 6.71–6.79 (2H,m), 7.18–7.40 (11H,m)

EXAMPLE 16

Preparation of 4-diphenylmethoxy-1-[3-(2-methanesulfonylaminophenoxy)-1-methylpropyl]piperidine

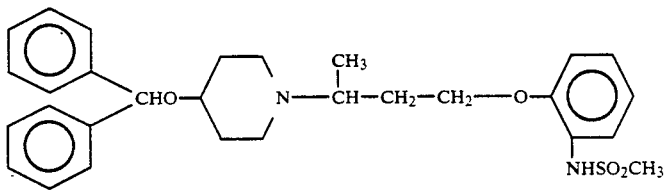

(a) The procedure of Example 1 (a) was repeated except for using diphenylmethyl bromide and 4-hydroxy-1-[1-methyl-3-(2-nitrophenoxy)propyl]piperidine instead of diphenylmethyl bromide and 4-hydroxy-1-[3-(2-nitrophenoxy)propyl]piperidine to give oily 4-diphenylmethoxy-1-[1-methyl-3-(2-nitrophenoxy)propyl]piperidine.

$^1$H-NMR (CDCl$_3$) δ:0.96 (3H,d), 1.50–2.02 (6H,m), 2.12 (1H,m), 2.35 (1H,m), 2.59–2.80 (2H,m), 2.81–2.96 (1H,m), 3.37 (1H,m), 4.07–4.27 (2H,m), 5.52 (1H,s), 6.92–7.53 (13H,m), 7.80 (1H,dd)

(b) The procedure of Example 1 (b) was repeated except for using the nitro compound obtained in (a) instead of 4-diphenylmethoxy-1-[3-(2-nitrophenoxy)propyl]piperidine to give 4-diphenylmethoxy-1-[3-(2-aminophenoxy)-1-methylpropyl]piperidine.

(c) The procedure of Example 1 (c) was repeated except for using the amino compound obtained in (b) instead of 4-diphenylmethoxy-1-[3-(2-aminophenoxy)propyl]piperidine to give the desired compound.

m.p.: 114°–115.5° C. (recrystallized from ethanol)

$^1$H-NMR (CDCl$_3$) δ:0.98 (3H,d), 1.55–2.00 (6H,m), 2.17 (1H,br t), 2.40 (1H,br t), 2.67 (1H, m), 2.72–2.88 (2H,m), 2.93 (3H,s), 3.40 (1H,m), 4.00–4.18 (2H,m), 5.52 (1H,s), 6.88–7.54 (14H,m)

EXAMPLE 17

Preparation of
4-diphenylmethoxy-1-[3-(2-methanesulfonylamino-phenoxy)-2-methylpropyl]piperidine

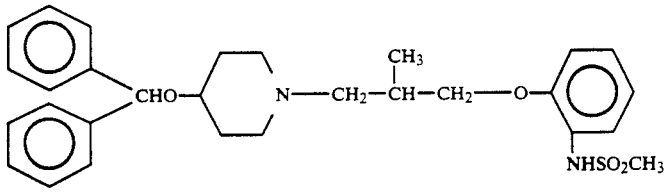

(a) The procedure of Example 1 (a) was repeated except for using diphenylmethyl bromide and 4-hydroxy-1-[2-methyl-3-(2-nitrophenoxy)propyl]piperidine instead of diphenylmethyl bromide and 4-hydroxy-1-[3-(2-nitrophenoxy)propyl]piperidine to give oily 4-diphenylmethoxy-1-[2-methyl-3-(2-nitrophenoxy)propyl]piperidine.

$^1$H-NMR (CDCl$_3$) δ:1.04 (3H,d), 1.57–1.77 (2H,m), 1.79–2.45 (7H,m), 2.66 (1H,m), 2.78 (1H,m), 3.40 (1H,m), 3.85–3.98 (1H,m), 4.05–4.16 (1H,m), 5.51 (1H,s), 6.89–7.52 (13H,m), 7.79 (1H,dd)

(b) The procedure of Example 1 (b) was repeated except for using the nitro compound obtained in (a) instead of 4-diphenylmethoxy-1-[3-(2-nitrophenoxy)-propyl]piperidine to give 4-diphenylmethoxy-1-[3-(2-aminophenoxy)-2-methylpropyl]piperidine.

(c) The procedure of Example 1 (c) was repeated except for using the amino compound obtained in (b) instead of 4-diphenylmethoxy-1-[3-(2-aminophenoxy)-propyl]piperidine to give the desired compound.

$^1$H-NMR (CDCl$_3$) δ:1.00 (3H,d), 1.60–1.79 (2H,m), 1.86 (2H,m), 1.98–2.41 (5H,m), 2.67 (1H,m), 2.77 (1H,m), 2.85 (3H,s), 3.42 (1H,m), 3.76–3.87 (1H,m), 3.93–4.05 (1H,m), 5.50 (1H,s) 6.85–7.52 (14H,m)

EXAMPLE 18

Preparation of
4-diphenylmethoxy-1-[3-(2-methanesulfonylamino-phenoxy)-3-methylpropyl]piperidine

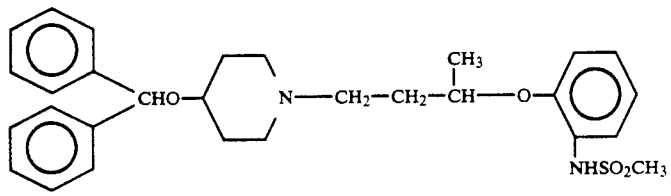

(a) The procedure of Example 1 (a) was repeated except for using diphenylmethyl bromide and 4-hydroxy-1-[3-methyl-3-(2-nitrophenoxy)propyl]piperidine instead of diphenylmethyl bromide and 4-hydroxy-1-[3-(2-nitrophenoxy)propyl]piperidine to give oily 4-diphenylmethoxy1-[3-methyl-3-(2-nitrophenoxy)propyl]piperidine.

$^1$H-NMR (CDCl$_3$) δ:1.35 (3H,d), 1.57–2.20 (8H,m), 2.46 (2H,m), 2.62–2.82 (2H,m), 3.43 (1H,m), 4.64 (1H,m), 5.51 (1H,s), 6.91–7.50 (13H,m), 7.75 (1H,dd)

(b) The procedure of Example 1 (b) was repeated except for using the nitro compound obtained in (a) instead of 4-diphenylmethoxy-1-[3-(2-nitrophenoxy)-propyl]piperidine to give 4-diphenylmethoxy-1-[3-(2-aminophenoxy)-3-methylpropyl]piperidine.

(c) The procedure of Example 1 (c) was repeated except for using the amino compound obtained in (b) instead of 4-diphenylmethoxy-1-[3-(2-aminophenoxy)-propyl]piperidine to give the desired compound.

$^1$H-NMR (CDCl$_3$) δ:1.30 (3H,d), 1.62–1.81 (2H,m), 1.82–1.97 (4H,m), 2.07–2.28 (2H,m), 2.32–2.55 (2H,m), 2.75 (2H,m), 2.94 (3H,s), 3.46 (1H,m), 4.50 (1H,m), 5.51 (1H,s), 6.89–7.53 (14H,m)

EXAMPLE 19

Preparation of
4-diphenylmethoxy-1-[4-(2-methanesulfonylamino-phenoxy)butyl]piperidine

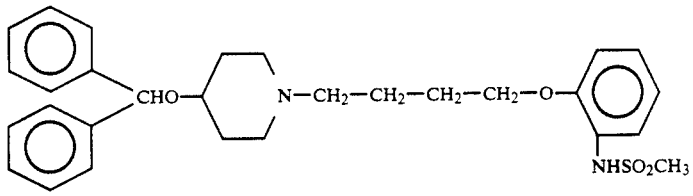

(a) The procedure of Example 1 (a) was repeated except for using diphenylmethylbromide and 4-hydroxy-1-[4-(2-nitrophenoxy)butyl]piperidine instead of diphenylmethyl bromide and 4-hydroxy-1-[3-(2-nitrophenoxy)propyl]piperidine to give oily 4-diphenyl-methoxy-1-[4-(2-nitrophenoxy)butyl]piperidine.

$^1$H-NMR (CDCl$_3$)δ: 1.58–1.97 (8H,m), 2.10 (2H,br t), 2.36 (2H,t), 2.75 (2H,m), 3.43 (1H,m), 4.11 (2H,t), 5.52 (1H,s), 6.93–7.55 (13H,m), 7.81 (1H,dd)

(b) The procedure of Example 1 (b) was repeated except for using the nitro compound obtained in (a) instead of 4-diphenylmethoxy-1-[3-(2-nitrophenoxy)- propyl]piperidine to give 4-diphenylmethoxy-1-[4-(2-aminophenoxy)butyl]piperidine.

(c) The procedure of Example 1 (c) was repeated except for using the amino compound obtained in (b) instead of 4-diphenylmethoxy-1-[3-(2-aminophenoxy)-propyl]piperidine to give the desired compound.

$^1$H-NMR (CDCl$_3$)δ: 1.58–2.00 (8H,m), 2.22 (2H,m), 2.42 (2H,br t), 2.77 (2H,m), 2.95 (3H,s), 3.47 (1H,m), 4.05 (2H,t), 5.51 (1H,s), 6.85–7.55 (14H,m)

$^1$H-NMR (CDCl$_3$)δ: 1.65–1.98 (4H,m), 2.08–2.29 (2H,m), 2.73 (2H,m), 2.94 (3H,s), 3.02 (2H,br d), 3.47 (1H,m), 4.57 (2H,br d), 5.51 (1H,s), 5.74–5.92 (2H,m), 6.88–7.58 (14H,m)

EXAMPLE 21

Preparation of 4-diphenylmethoxy-1-[4-(2-methanesulfonylamino-phenoxy)-2(Z)-butenyl]piperidine

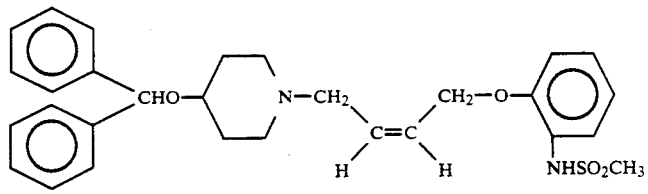

EXAMPLE 20

Preparation of 4-diphenylmethoxy-1-[4-(2-methanesulfonylamino-phenoxy)-2(E)-butenyl]piperidine (a) The procedure of Example 20 (a) was repeated except for using 4-diphenylmethoxypiperidine and 1-chloro-4-(2-nitrophenoxy)-2(Z)-butene instead of 4-diphenylmethoxypiperidine and 1-chloro-4-(2-nitrophenoxy)-2(E)-butene to give oily 4-diphenylmethoxy-

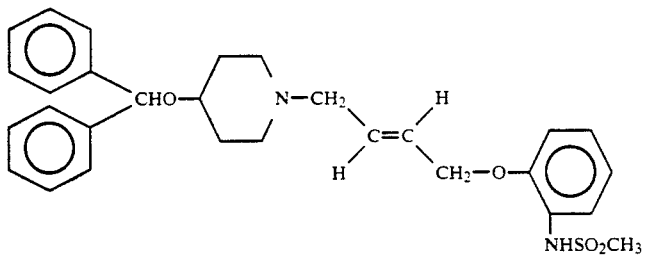

(a) Into 35 ml of dichloromethane were dissolved 2.67 g of 4-diphenylmethoxypiperidine, 2.96 g of 1-chloro-4-(2-nitrophenoxy)-2(E)-butene and 1.68 g of N,N-diisopropylethylamine, and the resultant solution was stirred at room temperature for 48 hours. The reaction solution was washed with water, and the solvent was removed under reduced pressure. The residue was eluted with ethanol-ethyl acetate (1:5) by silica gel column chromatography to give 2.75 g of oily 4-diphenylmethoxy-1-[4-(2-nitrophenoxy)-2(E)-butenyl]piperidine.

$^1$H-NMR (CDCl$_3$)δ: 1.64–1.97 (4H,m), 2.05–2.25 (2H,m), 2.64–2.81 (2H,m), 3.01 (2H,br d), 3.45 (1H,m), 4.66 (2H,br d), 5.51 (1H,s), 5.75–6.00 (2H,m), 6.94–7.52 (13H,m), 7.81 (1H,d)

(b) The procedure of Example 1 (b) was repeated except for using the nitro compound obtained in (a) instead of 4-diphenylmethoxy-1-[3-(2-nitrophenoxy)-propyl]piperidine to give 4-diphenylmethoxy-1-[4-(2-aminophenoxy)-2(E)-butenyl]piperidine.

(c) The procedure of Example 1 (c) was repeated except for using the amino compound obtained in (b) instead of 4-diphenylmethoxy-1-[3-(2-aminophenoxy)-propyl]piperidine to give the desired compound.

1-[4-(2-nitrophenoxy)-2(Z)-butenyl]piperidine.

$^1$H-NMR (CDCl$_3$)δ: 1.64–1.97 (4H,m), 2.05–2.25 (2H,m), 2.64–2.81 (2H,m), 3.06 (2H,br d), 3.45 (1H,m), 4.75 (2H,br d), 5.51 (1H,s), 5.70–5.87 (2H,m), 6.94–7.52 (13H,m), 7.81 (1H,d)

(b) The procedure of Example 1 (b) was repeated except for using the nitro compound obtained in (a) instead of 4-diphenylmethoxy-1-[3-(2-nitrophenoxy)-propyl]piperidine to give 4-diphenylmethoxy-1-[4-(2-aminophenoxy)-2(Z)-butenyl]piperidine.

(c) The procedure of Example 1 (c) was repeated except for using the amino compound obtained in (b) instead of 4-diphenylmethoxy-1-[3-(2-aminophenoxy)-propyl]piperidine to give the desired compound.

$^1$H-NMR (CDCl$_3$)δ: 1.65–1.98 (4H,m), 2.08–2.29 (2H,m), 2.73 (2H,m), 2.93 (3H,s), 3.04 (2H,br d), 3.47 (1H,m), 4.66 (2H,br d), 5.51 (1H,s), 5.74–5.92 (2H,m), 6.88–7.58 (14H,m)

EXAMPLE 22

Preparation of 4-diphenylmethoxy-1-[4-(2-methanesulfonylamino-phenoxy)-2-butynyl]piperidine

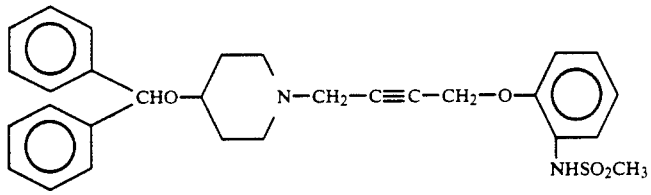

(a) Into 35 ml of dichloromethane were dissolved 2.67 g of 4-diphenylmethoxypiperidine, 2.93 g of 1-chloro-4-(2-nitrophenoxy)-2-butyne and 1.68 g of N,N-diisopropylethylamine, and the resultant solution was stirred at room temperature for 20 hours. The reaction solution was washed with water, and the solvent was removed under reduced pressure. The residue was eluted with ethyl acetate by silica gel column chromatography to give 2.95 g of oily 4-diphenylmethoxy-1-[4-(2-nitrophenoxy)-2-butynyl]piperidine.

$^1$H-NMR (CDCl$_3$)δ: 1.62–1.94 (4H,m), 2.21 (2H,m), 2.70 (2H,m), 3.29 (2H,s), 3.37 (1H,m), 4.85 (2H,s), 5.51 (1H,s), 6.92–7.44 (13H,m), 7.77 (1H,dd)

(b) The procedure of Example 1 (b) was repeated except for using the nitro compound obtained in (a) instead of 4-diphenylmethoxy-1-[3-(2-nitrophenoxy)-propyl]piperidine to give 4-diphenylmethoxy-1-[4-(2-nitrophenoxy)-2-butynyl]piperidine.

(c) The procedure of Example 1 (c) was repeated except for using the amino compound obtained in (b) instead of 4-diphenylmethoxy-1-[3-(2-aminophenoxy)-propyl]piperidine to give the desired compound.

$^1$H-NMR (CDCl$_3$)δ: 1.65–1.95 (4H,m), 2.10–2.28 (2H,m), 2.63–2.76 (2H,m), 2.92 (3H,s), 3.29 (2H,s), 3.37 (1H,m), 4.77 (2H,s), 5.51 (1H,s), 6.75–7.54 (14H,m)

EXAMPLE 23

Preparation of 4-diphenylmethoxy-1-[5-(2-methanesulfonylamino-phenoxy)pentyl]piperidine

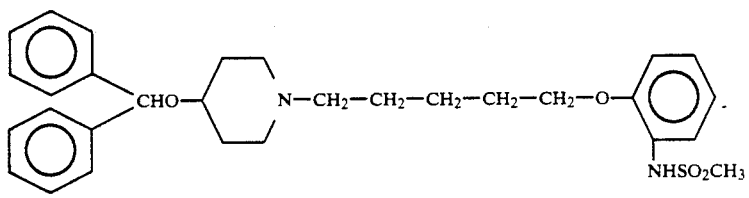

(a) The procedure of Example 1 (a) was repeated except for using diphenylmethyl bromide and 4-hydroxy-1-[5-(2-nitrophenoxy)pentyl]piperidine instead of diphenylmethyl bromide and 4-hydroxy-1-[3-(2-nitrophenoxy)propyl]piperidine to give oily 4-diphenyl-methoxy-1-[5-(2-nitrophenoxy)pentyl]piperidine.

$^1$H-NMR (CDCl$_3$)δ: 1.40–1.64 (4H,m), 1.66–1.99 (6H,m), 2.18 (2H,m), 2.36 (2H,br t), 2.77 (2H,m), 3.46 (1H,m), 4.08 (2H,t), 5.51 (1H,s), 6.94–7.54 (13H,m), 7.80 (1H,dd)

(b) The procedure of Example 1 (b) was repeated except for using the nitro compound obtained in (a) instead of 4-diphenylmethoxy-1-[3-(2-nitrophenoxy)-propyl]piperidine to give 4-diphenylmethoxy-1-[5-(2-aminophenoxy)pentyl]piperidine.

m.p.: 80°–81° C. (recrystallized from n-hexane)
$^1$H-NMR (CDCl$_3$)δ: 1.39–1.62 (4H,m), 1.65–1.95 (6H,m), 2.10 (2H,m), 2.32 (2H,t), 2.74 (2H,m), 3.43 (1H,m), 3.77 (2H,br s), 3.97 (2H,t), 5.52 (1H,s) 6.66–6.82 (4H,m), 7.19–7.39 (10H,m)

(c) The procedure of Example 1 (c) was repeated except for using the amino compound obtained in (b) instead of 4-diphenylmethoxy-1-[3-(2-aminophenoxy)-propyl]piperidine to give the desired compound.

$^1$H-NMR (CDCl$_3$)δ: 1.38–1.65 (4H,m), 1.66–1.98 (6H,m), 2.17 (2H,m), 2.35 (2H,t), 2.76 (2H,m), 2.94 (3H,s), 3.46 (1H,m), 4.02 (2H,t), 5.51 (1H,s), 6.84–7.54 (14H,m)

EXAMPLE 24

Preparation of 4-[(2-chlorophenyl)-phenylmethoxy]-1-[3-(2-methanesulfonylaminophenoxy)propyl]piperidine

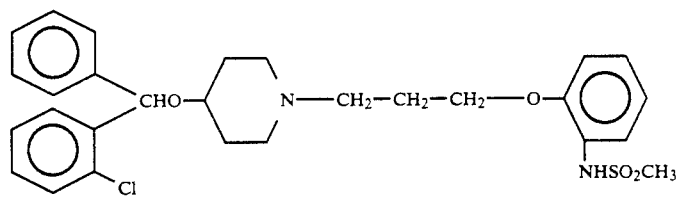

(a) Into 50 ml of toluene were dissolved 3.02 g of 4-[(2-chlorophenyl)-phenylmethoxy]piperidine, 2.59 g of 1-chloro-3-(2-nitrophenoxy)propane and 3.04 g of triethylamine, and the resultant solution was heated under reflux with stirring for 15 hours. After cooling, the reaction solution was washed with water, and the solvent was removed under reduced pressure. The residue was eluted with methanol-chloroform (1:50) by silica gel column chromatography to give 3.55 g of oily 4-[(2-chlorophenyl)-phenylmethoxy]-1-[3-(2-nitrophenoxy)propyl]piperidine.

$^1$H-NMR (CDCl$_3$)δ: 1.61–1.80 (2H,m), 1.82–2.25 (6H,m), 2.52 (2H,t), 2.69–2.84 (2H,m), 3.43 (1H,m), 4.15 (2H,t), 5.98 (1H,s), 6.94–7.63 (12H,m), 7.81 (1H,dd)

(b) The procedure of Example 1 (b) was repeated except for using the nitro compound obtained in (a) instead of 4-diphenylmethoxy-1-[3-(2-nitrophenoxy)propyl]piperidine to give 4-[(2-chlorophenyl)-phenylmethoxy]-1-[3-(2-aminophenoxy)propyl]piperidine.

(c) The procedure of Example 1 (c) was repeated except for using the amino compound obtained in (b) instead of 4-diphenylmethoxy-1-[3-(2-aminophenoxy)propyl]piperidine to give the desired compound.

$^1$H-NMR (CDCl$_3$)δ: 1.72–1.89 (2H,m), 1.93–2.15 (4H,m), 2.42 (2H,m), 2.64 (2H,br t), 2.78–2.92 (2H,m), 2.96 (3H,s), 3.52 (1H,m), 4.09 (2H,t), 5.97 (1H,s), 6.87–7.60 (13H,m)

EXAMPLE 25

Preparation of 4-[(4-chlorophenyl)-phenylmethoxy]-1-[3-(2-methanesulfonylaminophenoxy)propyl]piperidine.

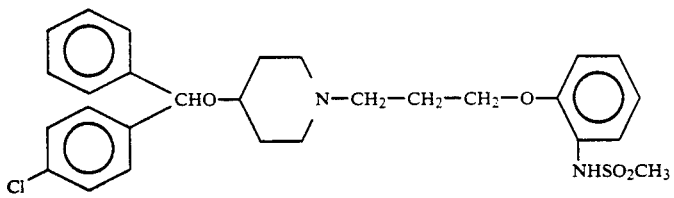

(a) The procedure of Example 24 (a) was repeated except for using 4-[(4-chlorophenyl)-phenylmethoxy]-piperidine and 1-chloro-3-(2-nitrophenoxy)propane instead of 4-[(2-chlorophenyl)-phenylmethoxy]piperidine and 1-chloro-3-(2-nitrophenoxy)propane to give oily 4-[(4-chlorophenyl)-phenylmethoxy]-1-[3-(2-nitrophenoxy)propyl]piperidine.

$^1$H-NMR (CDCl$_3$)δ: 1.60–1.77 (2H,m), 1.86 (2H,m), 1.98 (2H,quint), 2.13 (2H,br t), 2.51 (2H,t), 2.76 (2H,m), 3.41 (1H,m), 4.15 (2H,t), 5.48 (1H,s) 6.94–7.53 (12H,m), 7.80 (1H,dd)

(b) The procedure of Example 1 (b) was repeated except for using the nitro compound obtained in (a) instead of 4-diphenylmethoxy-1-[3-(2-nitrophenoxy)propyl]piperidine to give 4-[(4-chlorophenyl)-phenylmethoxy]-1-[3-(2-aminophenoxy)propyl]piperidine.

(c) The procedure of Example 1 (c) was repeated except for using the amino compound obtained in (b) instead of 4-diphenylmethoxy-1-[3-(2-aminophenoxy)propyl]piperidine to give the desired compound.

$^1$H-NMR (CDCl$_3$)δ: 1.63–1.79 (2H,m), 1.81–2.02 (4H,m), 2.16 (2H,br t), 2.47 (2H,t), 2.75 (2H,m), 2.94 (3H,s), 3.43 (1H,m), 4.08 (2H,t), 5.48 (1H,s) 6.89–7.37 (12H,m), 7.52 (1H,dd)

EXAMPLE 26

Preparation of 4-[(2-methylphenyl)-phenylmethoxy]-1-[3-(2-methanesulfonylaminophenoxy)propyl]piperidine

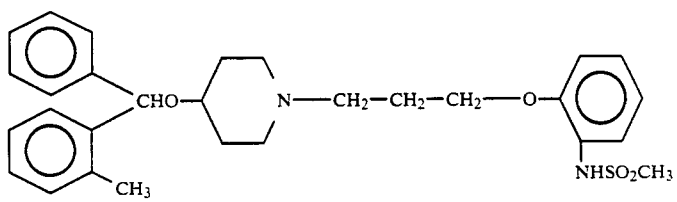

(a) The procedure of Example 24 (a) was repeated except for using 4-[(2-methylphenyl)-phenylmethoxy]-piperidine and 1-chloro-3-(2-nitrophenoxy)propane instead of 4-[(2-chlorophenyl)-phenylmethoxy]piperidine and 1-chloro-3-(2-nitrophenoxy)propane to give oily 4-[(2-methylphenyl)-phenylmethoxy]-1-[3-(2-nitrophenoxy)propyl]piperidine.

$^1$H-NMR (CDCl$_3$) δ:1.58–2.20 (8H,m), 2.25 (3H,s), 2.50 (2H,t), 2.77 (2H,m), 3.41 (1H,m), 4.15 (2H,t), 5.69 (1H,s), 6.93–7.57 (12H,m), 7.81 (1H,dd)

(b) The procedure of Example 1 (b) was repeated except for using the nitro compound obtained in (a) instead of 4-diphenylmethoxy-1-[3-(2-nitrophenoxy)propyl]piperidine to give 4-[(2-methylphenyl)-phenylmethoxy]-1-[3-(2-aminophenoxy)propyl]piperidine.

(c) The procedure of Example 1 (c) was repeated except for using the amino compound obtained in (b) instead of 4-diphenylmethoxy-1-[3-(2-aminophenoxy)propyl]piperidine to give the desired compound.

$^1$H-NMR (CDCl$_3$) δ:1.61–1.81 (2H,m), 1.83–2.02 (4H,m), 2.04–2.22 (2H,m), 2.25 (3H,s), 2.48 (2H,t), 2.77 (2H,m), 2.94 (3H,s), 3.44 (1H,m), 4.08 (2H,t), 5.69 (1H,s), 6.88–7.55 (13H,m)

EXAMPLE 27

Preparation of 4-[(3-methylphenyl)-phenylmethoxy]-1-[3-(2-methanesulfonylaminophenoxy)propyl]piperidine

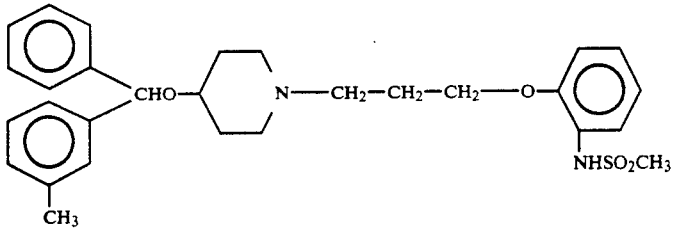

(a) The procedure of Example 24 (a) was repeated except for using 4-[(3-methylphenyl)-phenylmethoxy]-piperidine and 1-chloro-3-(2-nitrophenoxy)propane instead of 4-[(2-chlorophenyl)-phenylmethoxy]piperidine and 1-chloro-3-(2-nitrophenoxy)propane to give oily 4-[(3-methylphenyl)-phenylmethoxy]-1-[3-(2-nitrophenoxy)propyl]piperidine.

¹H-NMR (CDCl₃) δ:1.63–1.80 (2H,m), 1.83–2.07 (4H,m), 2.17 (2H,m), 2.32 (3H,s), 2.54 (2H,t), 2.79 (2H,m), 3.44 (1H,m), 4.16 (2H,t), 5.48 (1H,s), 6.95–7.54 (12H,m), 7.81 (1H,dd)

(b) The procedure of Example 1 (b) was repeated except for using the nitro compound obtained in (a) instead of 4-diphenylmethoxy-1-[3-(2-nitrophenoxy)propyl]piperidine to give 4-[(3-methylphenyl)-phenylmethoxy]-1-[3-(2-aminophenoxy)propyl]piperidine.

(c) The procedure of Example 1 (c) was repeated except for using the amino compound obtained in (b) instead of 4-diphenylmethoxy-1-[3-(2-aminophenoxy)propyl]piperidine to give the desired compound.

¹H-NMR (CDCl₃) δ:1.65–1.81 (2H,m), 1.83–2.03 (4H,m), 2.16 (2H,br t), 2.32 (3H,s), 2.48 (2H,t), 2.76 (2H,m), 2.94 (3H,s), 3.45 (1H,m), 4.08 (2H,t), 5.48 (1H,s), 6.90–7.38 (12H, m), 7.51 (1H,d)

EXAMPLE 28

Preparation of 4-[(4-methylphenyl)-phenylmethoxy]-1-[3-(2-methanesulfonylaminophenoxy)propyl]piperidine

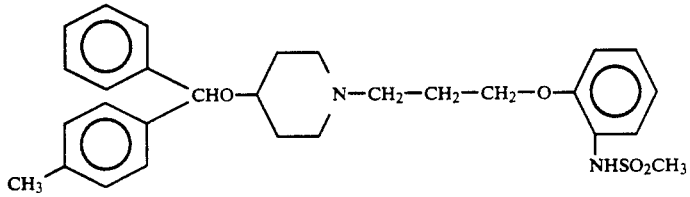

(a) The procedure of Example 24 (a) was repeated except for using 4-[(4-methylphenyl)-phenylmethoxy]-piperidine and 1-chloro-3-(2-nitrophenoxy)propane instead of 4-[(2-chlorophenyl)-phenylmethoxy]piperidine and 1-chloro-3-(2-nitrophenoxy)propane to give oily 4-[(4-methylphenyl)-phenylmethoxy]-1-[3-(2-nitrophenoxy)propyl]piperidine.

(b) The procedure of Example 1 (b) was repeated except for using the nitro compound obtained in (a) instead of 4-diphenylmethoxy-1-[3-(2-nitrophenoxy)propyl]piperidine to give 4-[(4-methylphenyl)-phenylmethoxy]-1-[3-(2-aminophenoxy)propyl]piperidine.

(c) The procedure of Example 1 (c) was repeated except for using the amino compound obtained in (b) instead of 4-diphenylmethoxy-1-[3-(2-aminophenoxy)propyl]piperidine to give the desired compound.

¹H-NMR (CDCl₃) δ:1.64–1.79 (2H,m), 1.80–2.03 (4H,m), 2.17 (2H,br t), 2.32 (3H,s), 2.48 (2H,t), 2.76 (2H,m), 2.94 (3H,s), 3.45 (1H,m), 4.08 (2H,t), 5.49 (1H,s), 6.88–7.54 (13H,m),

EXAMPLE 29

Preparation of 4-[(4-methoxyphenyl)-phenylmethoxy]-1-[3-(2-methanesulfonylaminophenoxy)propyl]piperidine

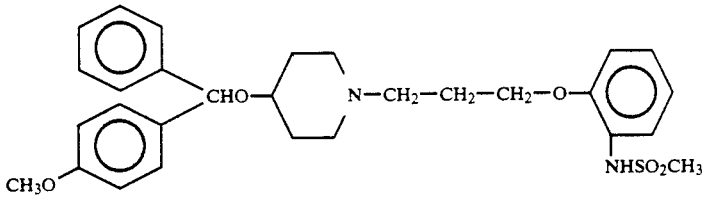

(a) The procedure of Example 24 (a) was repeated except for using 4-[(4-methoxyphenyl)-phenylmethoxy]piperidine and 1-chloro-3-(2-nitrophenoxy)propane instead of 4-[(2-chlorophenyl)-phenylmethoxy]piperidine and 1-chloro-3-(2-nitrophenoxy)propane to give oily 4-[(4-methoxyphenyl)-phenylmethoxy]-1-[3-(2-nitrophenoxy)propyl]piperidine.

¹H-NMR (CDCl₃) δ:1.58–1.78 (2H,m), 1.86 (2H,m), 1.98 (2H,quint), 2.12 (2H,br t), 2.50 (2H,t), 2.76 (2H,m), 3.41 (1H,m), 3.78 (3H,s), 4.15 (2H,t), 5.48 (1H,s), 6.80–7.54 (12H,m), 7.81 (1H,dd)

(b) The procedure of Example 1 (b) was repeated except for using the nitro compound obtained in (a) instead of 4-diphenylmethoxy-1-[3-(2-nitrophenoxy)-propyl]piperidine to give 4-[(4-methoxyphenyl)-phenyl-methoxy]-1-[3-(2-aminophenoxy)propyl]piperidine.

(c) The procedure of Example 1 (c) was repeated except for using the amino compound obtained in (b) instead of 4-diphenylmethoxy-1-[3-(2-aminophenoxy)-propyl]piperidine to give the desired compound.

1H-NMR (CDCl$_3$) δ:1.63–1.80 (2H,m), 1.82–2.03 (4H,m), 2.16 (2H,br t), 2.48 (2H,t), 2.76 (2H,m), 2.94 (3H,s), 3.44 (1H,m), 3.78 (3H,s), 4.08 (2H,t), 5.48 (1H,s), 6.79–7.38 (12H,m), 7.52 (1H,d)

EXAMPLE 30

Preparation of 4-di(4-fluorophenyl)methoxy-1-[3-(2-methanesulfonylaminophenoxy)propyl]piperidine

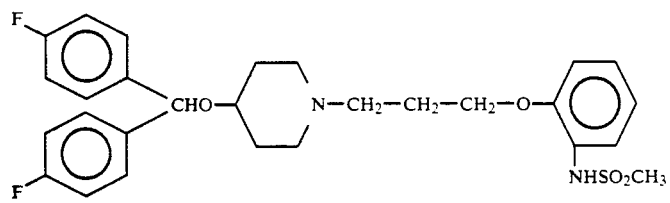

(a) The procedure of Example 1 (a) was repeated except for using di(4-fluorophenyl)methyl chloride and 4-hydroxy-1-[3-(2-nitrophenoxy)propyl]piperidine instead of diphenylmethyl bromide and 4-hydroxy-1-[3-(2-nitrophenoxy)propyl]piperidine to give oily 4-di(4-fluorophenyl)methoxy-1-[3-(2-nitrophenoxy)propyl]-piperidine.

1H-NMR (CDCl$_3$) δ:1.54–1.77 (2H,m), 1.80–1.94(2H,m), 1.99 (2H,quint), 2.12 (2H,m), 2.52 (2H,t), 2.75 (2H,m), 3.38 (1H,m), 4.15 (2H,t), 5.47 (1H,s), 6.90–7.14 (6H,m), 7.20–7.35 (4H,m), 7.50 (1H,t), 7.82 (1H,d)

(b) The procedure of Example 1 (b) was repeated except for using the nitro compound obtained in (a) instead of 4-diphenylmethoxy-1-[3-(2-nitrophenoxy)-propyl]piperidine to give 4-di(4-fluorophenyl)methoxy-1-[3-(2-aminophenoxy)propyl]piperidine.

(c) The procedure of Example 1 (c) was repeated except for using the amino compound obtained in (b) instead of 4-diphenylmethoxy-1-[3-(2-aminophenoxy)-propyl]piperidine to give the desired compound.

1H-NMR (CDCl$_3$) δ:1.62–1.79 (2H,m), 1.82–2.03 (4H,m), 2.16 (2H,br t), 2.48 (2H,t), 2.75 (2H,m), 2.94 (3H,s), 3.42 (1H,m), 4.08 (2H,t), 5.47 (1H,s), 6.89–7.33 (11H,m), 7.52 (1H,d),

EXAMPLE 31

Preparation of 4-(cyclopentyl-phenylmethoxy)-1-[3-(2-methanesulfonylaminophenoxy)propyl]piperidine

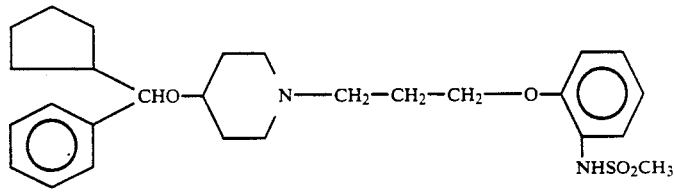

(a) Into 35 ml of methyl isobutyl ketone were dissolved 2.92 g of cyclopentyl-phenylmethyl chloride, 2.80 g of 4-hydroxy-1-[3-(2-nitrophenoxy)propyl]piperidine and 1.94 g of N,N-diisopropylethylamine, and the resultant solution was heated under reflux with stirring for 72 hours. After cooling, the reaction solution was washed with water, and the solvent was removed under reduced pressure. The residue was eluted with ethyl acetate-ethanol-dichloromethane (1:1:1) by silica gel column chromatography to give 0.88 g of oily 4-(cyclopentyl-phenylmethoxy)-1-[3-(2-nitrophenoxy)propyl]-piperidine.

1H-NMR (CDCl$_3$) δ:1.00–1.72 (11H,m), 1.78–2.20 (6H,m), 2.50 (2H,t), 2.60–2.80 (2H,m), 3.19 (1H,m), 4.05 (1H,d), 4.15 (2H,t), 6.95–7.56 (8H,m), 7.81 (1H,dd)

(b) The procedure of Example 1 (b) was repeated except for using the nitro compound obtained in (a) instead of 4-diphenylmethoxy-1-[3-(2-nitrophenoxy)-propyl]piperidine to give 4-(cyclopentyl-phenylmethoxy)-1-[3-(2-aminophenoxy)propyl]piperidine.

(c) The procedure of Example 1 (c) was repeated except for using the amino compound obtained in (b) instead of 4-diphenylmethoxy-1-[3-(2-aminophenoxy)-propyl]piperidine to give the desired compound.

1H-NMR (CDCl$_3$) δ:1.03–1.74 (11H,m), 1.78–2.26 (6H,m), 2.47 (2H,t), 2.59–2.80 (2H,m), 2.94 (3H,s), 3.21 (1H,m), 3.98–4.13 (3H,m), 6.88–7.37 (8H,m) 7.51 (1H, dd)

EXAMPLE 32

Preparation of 4-(phenyl-2-pyridylmethoxy)-1-[3-(2-methanesulfonylaminophenoxy)propyl]piperidine

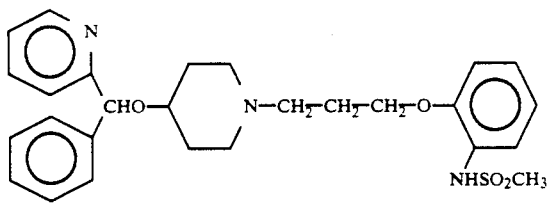

(a) There was stirred at 120° C. for 4 hours a mixture of 6.74 g of phenyl-2-pyridylmethanol, 7.85 g of 4-hydroxy-1-[3-(2-nitrophenoxy)propyl]piperidine, 11.0 g of concentrated sulfuric acid and 15 ml of toluene. After cooling, the reaction solution was poured into ice water, made alkaline with an aqueous sodium hydroxide, and extracted with toluene. The extract was washed with water, and toluene was removed under reduced pressure. The residue was eluted with ethyl acetate-ethanol-dichloromethane (1:1:1) by silica gel column chromatography to give 3.67 g of oily 4-(phenyl-2-pyridylmethoxy)-1-[3-(2-nitrophenoxy)propyl]piperidine.

$^1$H-NMR (CDCl$_3$) δ:1.60–2.05 (6H,m), 2.14 (2H,m), 2.51 (2H,t), 2.75 (2H,m), 3.47 (1H,m), 4.15 (2H,t), 5.64 (1H,s), 6.92–7.87 (12H,m), 8.51 (1H,dd)

(b) The procedure of Example 1 (b) was repeated except for using the nitro compound obtained in (a) instead of 4-diphenylmethoxy-1-[3-(2-nitrophenoxy)propyl]piperidine to give 4-(phenyl-2-pyridylmethoxy)-1-[3-(2-aminophenoxy)propyl]piperidine.

(c) Into 25 ml of dichloromethane were dissolved 2.0 g of the amino compound obtained in (b) and 1.1 g of pyridine, and 0.66 g of methanesulfonyl chloride was added dropwise to the resultant solution with ice cooling, followed by stirring for 1 hour. The reaction solution was poured into ice water, and extracted with ethyl acetate. The extract was washed with water, and ethyl acetate was removed. The residue was eluted with ethanol-dichloromethane (1:5) by silica gel column chromatography to give 1.78 g of the desired compound.

$^1$H-NMR (CDCl$_3$) δ:1.65–1.83 (2H,m), 1.84–2.03 (4H,m), 2.17 (2H,m), 2.49 (2H,t), 2.75 (2H,m), 2.94 (3H,s), 3.50 (1H,m), 4.08 (2H,t) 5.64 (1H,s), 6.88–7.71 (12H,m), 8.51 (1H,dd)

EXAMPLE 33

Preparation of 4-[(4-chlorophenyl)-2-pyridylmethoxy]-1-[3-(2-methanesulfonylaminophenoxy)propyl]piperidine

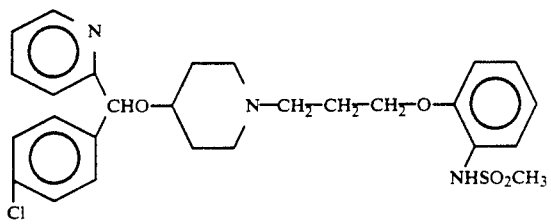

(a) The procedure of Example 32 (a) was repeated except for using (4-chlorophenyl)-2-pyridylmethanol and 4-hydroxy-1-[3-(2-nitrophenoxy)propyl]piperidine instead of phenyl-2-pyridylmethanol and 4-hydroxy-1-[3-(2-nitrophenoxy)propyl]piperidine to give oily 4-[(4-chlorophenyl)-2-pyridylmethoxy]-1-[3-(2-nitrophenoxy)propyl]piperidine.

$^1$H-NMR (CDCl$_3$) δ:1.60–2.30 (8H,m), 2.56 (2H,m), 2.79 (2H,m), 3.49 (1H,m), 4.15 (2H,t), 5.59 (1H,s), 6.95–7.85(11H,m), 8.51 (1H,d)

(b) The procedure of Example 1 (b) was repeated except for using the nitro compound obtained in (a) instead of 4-diphenylmethoxy-1-[3-(2-nitrophenoxy)propyl]piperidine to give 4-[(4-chlorophenyl)-2-pyridylmethoxy]-1-[3-(2-aminophenoxy)propyl]piperidine $^1$H-NMR (DMSO-d$_6$) δ:1.60–2.30 (8H,m), 2.57 (2H,t), 2.76 (2H,m), 3.49 (1H,m), 3.82 (2H,br s), 4.03 (2H,t), 5.78 (1H,s), 6.50–6.85 (4H,m), 7.30–7.93 (7H,m), 8.55 (1H,dd)

(c) The procedure of Example 32 (c) was repeated except for using the amino compound obtained in (b) instead of 4-(phenyl-2-pyridylmethoxy)-1-[3-(2-aminophenoxy)propyl]piperidine to give the desired compound.

$^1$H-NMR (CDCl$_3$) δ:1.63–1.82 (2H,m), 1.83–2.03 (4H,m), 2.17 (2H,m), 2.48 (2H,t), 2.74 (2H,m), 2.94 (3H,s), 3.48 (1H,m), 4.08 (2H,t) 5.60 (1H,s), 6.89–7.73 (11H,m), 8.51 (1H,br d)

EXAMPLE 34

Preparation of 4-(phenyl-3-pyridylmethoxy)-1-[3-(2-methanesulfonylaminophenoxy)propyl]piperidine

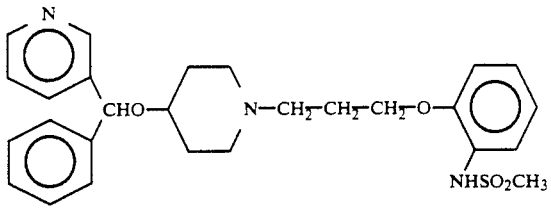

(a) The procedure of Example 24 (a) was repeated except for using 4-(phenyl-3-pyridylmethoxy)piperidine and 1-chloro-3-(2-nitrophenoxy)propane instead of 4-[(2-chlorophenyl)-phenylmethoxy]piperidine and 1-chloro-3-(2-nitrophenoxy)propane to give oily 4-(phenyl-3-pyridylmethoxy)-1-[3-(2-nitrophenoxy)propyl]piperidine.

$^1$H-NMR (CDCl$_3$) δ:1.60–1.78 (2H,m), 1.87 (2H,m), 1.99 (2H,qunit), 2.15 (2H,m), 2.52 (2H,t), 2.76 (2H,m), 3.44 (1H,m), 4.16 (2H,t), 5.55 (1H,s), 6.90–7.86 (11H,m), 8.49 (1H,br d), 8.60 (1H,br s)

(b) The procedure of Example 1 (b) was repeated except for using the nitro compound obtained in (a) instead of 4-diphenylmethoxy-1-[3-(2-nitrophenoxy)propyl]piperidine to give 4-(phenyl-3-pyridylmethoxy)-1-[3-(2-aminophenoxy)propyl]piperidine.

(c) The procedure of Example 32 (c) was repeated except for using the amino compound obtained in (b) instead of 4-(phenyl-2-pyridylmethoxy)-1-[3-(2-aminophenoxy)propyl]piperidine to give the desired compound.

$^1$H-NMR (CDCl$_3$) δ:1.63–2.07 (6H,m), 2.10–2.30 (2H,m), 2.51 (2H,br t), 2.76 (2H,m), 2.95 (3H,s), 3.48

(1H,m), 4.09 (2H,t), 5.55 (1H,s) 6.87-7.67(11H,m), 8.50 (1H,br d), 8.60 (1H,s)

EXAMPLE 35

Preparation of 4-(phenyl-4-pyridylmethoxy)-1-[3-(2-methanesulfonylaminophenoxy)propyl]piperidine

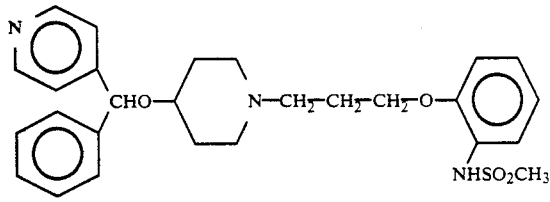

(a) The procedure of Example 24 (a) was repeated except for using 4-(phenyl-4-pyridylmethoxy)piperidine and 1-chloro-3-(2-nitrophenoxy)propane instead of 4-[(2-chlorophenyl)-phenylmethoxy]piperidine and 1-chloro-3-(2-nitrophenoxy)propane to give oily 4-(phenyl-4-pyridylmethoxy)-1-[3-(2-nitrophenoxy)propyl]piperidine.

$^1$H-NMR (CDCl$_3$) δ:1.60-2.08 (6H,m), 2.15 (2H,m), 2.53 (2H,t), 2.76 (2H,m), 3.43 (1H,m), 4.16 (2H,t), 5.47 (1H,s), 6.95-7.56 (10H,m), 7.81 (1H,dd), 8.53 (2H, d)

(b) The procedure of Example 1 (b) was repeated except for using the nitro compound obtained in (a) instead of 4-diphenylmethoxy-1-[3-(2-nitrophenoxy)-propyl]piperidine to give 4-(phenyl-4-pyridylmethoxy)-1-[3-(2-aminophenoxy)propyl]piperidine.

(c) The procedure of Example 32 (c) was repeated except for using the amino compound obtained in (b) instead of 4-(phenyl-2-pyridylmethoxy)-1-[3-(2-aminophenoxy)propyl]piperidine to give the desired compound.

$^1$H-NMR (CDCl$_3$) δ:1.65-2.06 (6H,m), 2.23 (2H,m), 2.52 (2H,br t), 2.77 (2H,m), 2.95 (3H,s), 3.47 (1H,m), 4.09 (2H,t), 5.47 (1H,s), 6.85-7.55 (11H,m), 8.54 (2H,d)

EXAMPLE 36

Preparation of 4-(phenyl-2-thienylmethoxy)-1-[3-(2-methanesulfonylaminophenoxy)propyl]piperidine

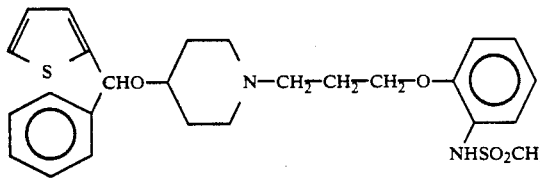

(a) Into 50 ml of methyl isobutyl ketone were dissolved 5.0 g of phenyl-2-thienylmethyl chloride, 8.1 g of 4-hydroxy-1-[3-(2-nitrophenoxy)propyl]piperidine and 7.3 g of triethylamine, and the resultant solution was heated under reflux with stirring for 3 hours. After cooling, the reaction solution was washed with water, and the solvent was removed under reduced pressure.

The residue was eluted with ethyl acetate-ethanoldichloromethane (1:1:1) by silica gel column chlomatography to give 8.46 g of 4-(phenyl-2-thienylmethoxy)-1-[3-(2-nitrophenoxy)propyl]piperidine hydrochloride.

$^1$H-NMR (CDCl$_3$) δ:1.80-2.07 (2H,m), 2.11-2.44 (4H,m), 2.80-3.20 (6H,m), 3.77 (1H,m), 4.25 (2H,t), 5.68 (1H,s), 6.72-7.59 (11H,m), 7.85 (1H,dd)

In 20 ml of 5% aqueous sodium carbonate solution was suspended 1.0 g of the hydrochloride obtained in the above. The resultant solution was extracted with ethyl acetate and the organic layer was washed with water. The solvent was removed under reduced pressure to give 0.83 g of oily 4-(phenyl-2-thienylmethoxy)-1-[3-(2-nitrophenoxy)propyl]piperidine.

$^1$H-NMR (CDCl$_3$) δ:1.59-2.07 (6H,m), 2.08-2.30 (2H,m), 2.54 (2H,t), 2.78 (2H,m), 3.51 (1H,m), 4.16 (2H,t), 5.72 (1H,s), 6.71-7.55 (11H,m), 7.81 (1H,dd)

(b) The procedure of Example 1 (b) was repeated except for using the nitro compound obtained in (a) instead of 4-diphenylmethoxy-1-[3-(2-nitrophenoxy)-propyl]piperidine to give 4-(phenyl-2-thienylmethoxy)-1-[3-(2-aminophenoxy)propyl]piperidine.

$^1$H-NMR (CDCl$_3$) δ:1.57-2.37 (8H,m), 2.54 (2H,t), 2.66-2.88 (2H,m), 3.52 (1H,m), 3.81 (2H,br s), 4.03 (2H,t), 5.72 (1H,s), 6.59-7.47 (12H,m)

(c) The procedure of Example 1 (c) was repeated except for using the amino compound obtained in (b) instead of 4-diphenylmethoxy-1-[3-(2-aminophenoxy)-propyl]piperidine, and the crude product thus obtained was eluted with ethyl acetate-ethanol-dichloromethane (5:1:3) by silica gel column chromatography to give the desired compound.

m.p.: 102°-104.5° C. (recrystallized from ethyl acetate-n-hexane)

$^1$H-NMR (CDCl$_3$) δ:1.63-2.05 (6H,m), 2.11-2.31 (2H,m), 2.50 (2H,t), 2.75 (2H,m), 2.94 (3H,s) 3.52 (1H,m), 4.09 (2H,t), 5.72 (1H,s), 6.72-7.56 (12H,m)

The procedure of Example 3 was repeated except for using the desired compound obtained in the above and fumaric acid instead of 4-diphenylmethoxy-1-[3-(2-methanesulfonylaminophenoxy)propyl]piperidine and fumaric acid to give the fumarate of the desired compound.

m.p.: 165°-168° C. (recrystallized from isopropyl alcohol)

The procedure of Example 3 was repeated except for using the desired compound obtained in the above and oxalic acid instead of 4-diphenylmethoxy-1-[3-(2-methanesulfonylaminophenoxy)propyl]piperidine and fumaric acid to give the oxalate of the desired compound.

m.p.: 186°-189° C. (recrystallized from methanol)

EXAMPLE 37

Preparation of 4-(phenyl-2-thienylmethoxy)-1-[3-(2-methanesulfonylaminophenoxy)-1-methylpropyl]piperidine

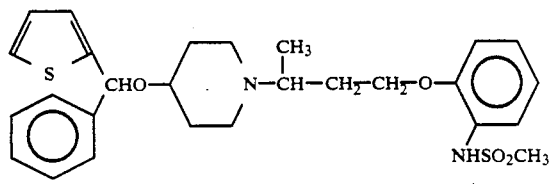

(a) The procedure of Example 36 (a) was repeated except for using phenyl-2-thienylmethyl chloride and 4-hydroxy-1-[1-methyl-3-(2-nitrophenoxy)propyl]-piperidine instead of phenyl-2-thienylmethyl chloride and 4-hydroxy-1-[3-(2-nitrophenoxy)propyl]piperidine to give oily 4-(phenyl-2-thienylmethoxy)-1-[3-(2-nitrophenoxy)-1-methylpropyl]piperidine.

¹H-NMR (CDCl₃) δ:0.98 (3H,d), 1.50-2.07 (6H,m), 2.07-2.23 (1H,m), 2.28-2.45 (1H,m), 2.58-2.97 (3H,m), 3.43 (1H,m), 4.06-4.28 (2H,m), 5.73 (1H,s), 6.71-7.55 (11H,m), 7.80 (1H,dd)

(b) The procedure of Example 1 (b) was repeated except for using the nitro compound obtained in (a) instead of 4-diphenylmethoxy-1-[3-(2-nitrophenoxy)-propyl]piperidine to give 4-(phenyl-2-thienylmethoxy)-1-[3-(2-aminophenoxy)-1-methylpropyl]piperidine.

¹H-NMR (CDCl₃) δ:1.00 (3H,d), 1.55-2.09 (6H,m), 2.12-2.28 (1H,m), 2.30-2.46 (1H,m), 2.63-2.97 (3H,m), 3.46 (1H,m), 3.82 (2H,br s), 3.93-4.18 (2H,m), 5.73 (1H,s), 6.62-6.96 (6H,m), 7.20-7.47 (6H,m)

(c) The procedure of Example 1 (c) was repeated except for using the amino compound obtained in (b) instead of 4-diphenylmethoxy-1-[3-(2-aminophenoxy)-propyl]piperidine to give the desired compound.

m.p.: 100°-102.5° C.

¹H-NMR (CDCl₃) δ:1.00 (3H,d), 1.55-2.07 (6H,m), 2.12-2.28 (1H,m), 2.34-2.50 (1H,m), 2.61-2.93 (3H,m), 2.94 (3H,s) 3.47 (1H,m), 4.00-4.20 (2H,m), 5.73 (1H,s), 6.72-7.57 (12H,m)

EXAMPLE 38

Preparation of 4-(phenyl-2-thienylmethoxy)-1-[3-(2-methanesulfonylaminophenoxy)-3-methylpropyl]piperidine

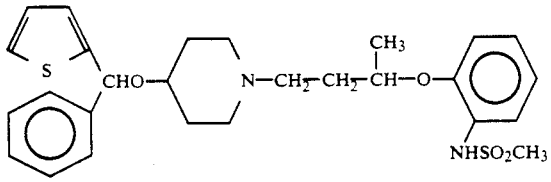

(a) The procedure of Example 36 (a) was repeated except for using phenyl-2-thienylmethyl chloride and 4-hydroxy-1-[3-methyl-3-(2-nitrophenoxy)propyl]piperidine instead of phenyl-2-thienylmethyl chloride and 4-hydroxy-1-[3-(2-nitrophenoxy)propyl]piperidine to give oily 4-(phenyl-2-thienylmethoxy)-1-[3-(2-nitrophenoxy)-3-methylpropyl]piperidine.

¹H-NMR (CDCl₃) δ:1.35 (3H,d), 1.55-2.29 (8H,m), 2.44 (2H,m), 2.60-2.84 (2H,m), 3.48 (1H,m), 4.63 (1H,m), 5.72 (1H,s) 6.72-7.52 (11H,m), 7.74 (1H,d)

(b) The procedure of Example 1 (b) was repeated except for using the nitro compound obtained in (a) instead of 4-diphenylmethoxy-1-[3-(2-nitrophenoxy)-propyl]piperidine to give 4-(phenyl-2-thienylmethoxy)-1-[3-(2-aminophenoxy)-3-methylpropyl]piperidine.

(c) The procedure of Example 1 (c) was repeated except for using the amino compound obtained in (b) instead of 4-diphenylmethoxy-1-[3-(2-aminophenoxy)-propyl]piperidine to give the desired compound.

¹H-NMR (CDCl₃) δ:1.31 (3H,d), 1.62-2.04 (6H,m), 2.23 (2H,m), 2.34-2.58 (2H,m), 2.75 (2H,m), 2.95 (3H,s), 3.52 (1H,m) 4.50 (1H,m), 5.71 (1H,s) 6.72-7.55 (12H,m)

EXAMPLE 39

Preparation of 4-(phenyl-2-thienylmethoxy)-1-[4-(2-methanesulfonylaminophenoxy)-2(E)-butenyl]piperidine

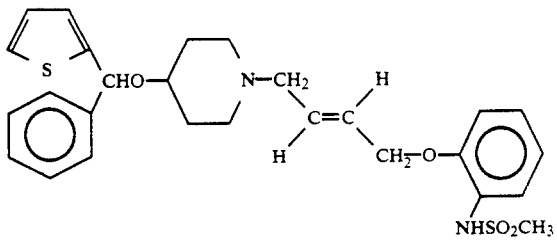

(a) Into 20 ml of methyl isobutyl ketone were dissolved 2.09 g of phenyl-2-thienylmethyl chloride, 3.50 g of 4-hydroxy-1-[4-(2-nitrophenoxy)-2(E)-butenyl]-piperidine and 1.94 g of N,N-diisopropylethylamine, and the resultant solution was heated under reflux with stirring for 2 hours. After cooling, the reaction solution was washed with water, and the solvent was removed under reduced pressure. The residue was eluted with ethanol-chloroform (1:50) by silica gel column chromatography to give 3.06 g of oily 4-(phenyl-2-thienylmethoxy)-1-[4-(2-nitrophenoxy)-2(E)-butenyl]piperidine.

¹H-NMR (CDCl₃) δ: 1.61-2.32 (6H,m), 2.72 (2H,m), 3.02 (2H,d), 3.50 (1H,m), 4.67 (2H,d), 5.71 (1H,s), 5.75-6.01 (2H,m) 6.70-7.54 (11H,m), 7.82 (1H,dd)

(b) The procedure of Example 1 (b) was repeated except for using the nitro compound obtained in (a) instead of 4-diphenylmethoxy-1-[3-(2-nitrophenoxy)-propyl]piperidine to give 4-(phenyl-2-thienylmethoxy)-1-[4-(2-aminophenoxy)-2(E)-butenyl]piperidine.

(c) The procedure of Example 1 (c) was repeated except for using the amino compound obtained in (b) instead of 4-diphenylmethoxy-1-[3-(2-aminophenoxy)-propyl]piperidine to give the desired compound.

m.p.: 114°-117° C.

¹H-NMR (CDCl₃) δ: 1.63-2.00 (4H,m), 2.10-2.30 (2H,m), 2.73 (2H,m), 2.94 (3H,s), 3.03 (2H,d), 3.51 (1H,m), 4.58 (2H,d), 5.72 (1H,s) 5.75-5.97 (2H,m), 6.73-7.58 (12H,m)

EXAMPLE 40

Preparation of 4-(phenyl-2-thienylmethoxy)-1-[4-(2-methanesulfonylaminophenoxy)-2(Z)-butenyl]piperidine

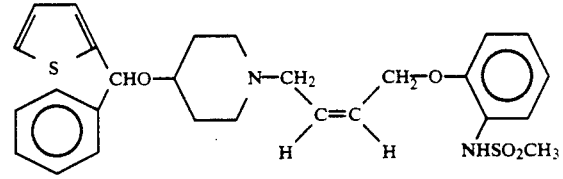

(a) The procedure of Example 39 (a) was repeated except for using phenyl-2-thienylmethyl chloride and 4-hydroxy-1-[4-(2-nitrophenoxy)-2(Z)-butenyl]piperidine instead of phenyl-2-thienylmethyl chloride and 4-hydroxy-1-[4-(2-nitrophenoxy)-2(E)-butenyl]piperidine to give oily 4-(phenyl-2-thienylmethoxy)-1-[4-(2-nitrophenoxy)-2(Z)-butenyl]piperidine.

$^1$H-NMR (CDCl$_3$) δ: 1.60–2.00 (4H,m), 2.05–2.34 (2H,m), 2.74 (2H,m), 3.06 (2H,d), 3.52 (1H,m), 4.76 (2H,d), 5.72 (1H,s) 5.73–5.92 (2H,m), 6.70–7.57 (11H,m), 7.81 (1H,dd)

(b) The procedure of Example 1 (b) was repeated except for using the nitro compound obtained in (a) instead of 4-diphenylmethoxy-1-[3-(2-nitrophenoxy)-propyl]piperidine to give 4-(phenyl-2-thienylmethoxy)-1-[4-(2-aminophenoxy)-2(Z)-butenyl]piperidine.

(c) The procedure of Example 1 (c) was repeated except for using the amino compound obtained in (b) instead of 4-diphenylmethoxy-1-[3-(2-aminophenoxy)-propyl]piperidine to give the desired compound.

m.p.: 99°–103° C.

$^1$H-NMR (CDCl$_3$) δ: 1.63–2.03 (4H,m), 2.12–2.37 (2H,m), 2.73 (2H,m), 2.93 (3H,s), 3.05 (2H,d), 3.53 (1H,m), 4.66 (2H,d), 5.72 (1H,s), 5.73–5.93 (2H,m), 6.68–7.62 (12H,m)

EXAMPLE 41

Preparation of 4-(phenyl-3-thienylmethoxy)-1-[3-(2-methanesulfonylaminophenoxy)propyl]piperidine

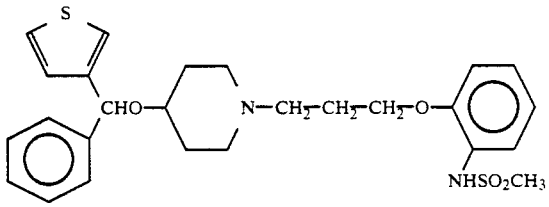

(a) The procedure of Example 36 (a) was repeated except for using phenyl-3-thienylmethyl chloride and 4-hydroxy-1-[3-(2-nitrophenoxy)propyl]piperidine instead of phenyl-2-thienylmethyl chloride and 4-hydroxy-1-[3-(2-nitrophenoxy)propyl]piperidine to give 4-(phenyl-3-thienylmethoxy)-1-[3-(2-nitrophenoxy)propyl]piperidine hydrochloride.

$^1$H-NMR (CDCl$_3$) δ: 1.82–2.07 (2H,m), 2.13–2.48 (4H,m), 2.83–3.23 (6H,m), 3.74 (1H,m), 4.25 (2H,t), 5.53 (1H,s), 6.90–7.61 (11H,m), 7.85 (1H,dd)

The hydrochloride obtained in the above was treated with 5% aqueous sodium carbonate in the same way as in Example 36 (a) to give oily 4-(phenyl-3-thienylmethoxy)-1-[3-(2-nitrophenoxy)propyl]piperidine.

$^1$H-NMR (CDCl$_3$) δ: 1.62–2.10 (6H,m), 2.22 (2H,m), 2.56 (2H,t), 2.80 (2H,m), 3.46 (1H,m), 4.17 (2H,t), 5.57 (1H,s) 6.94–7.56 (11H,m), 7.81 (1H,dd)

(b) The procedure of Example 1 (b) was repeated except for using the nitro compound obtained in (a) instead of 4-diphenylmethoxy-1-[3-(2-nitrophenoxy)-propyl]piperidine to give 4-(phenyl-3-thienylmethoxy)-1-[3-(2-aminophenoxy)propyl]piperidine.

(c) The procedure of Example 1 (c) was repeated except for using the amino compound obtained in (b) instead of 4-diphenylmethoxy-1-[3-(2-aminophenoxy)-propyl]piperidine to give the hydrochloride of the desired compound.

m.p.: 175.5°–178° C. (recrystallized from ethanol-n-hexane)

$^1$H-NMR (CDCl$_3$) δ: 1.80–2.55 (6H,m), 3.03 (3H,s), 3.18 (2H,m), 3.31 (2H,t), 3.46 (2H,m), 3.81 (1H,m), 4.13 (2H,t), 5.49 (1H,s), 6.81–7.49 (12H,m), 7.74 (1H,br s)

The hydrochloride obtained in the above was treated with 5% aqueous sodium carbonate to give the desired compound.

m.p.: 79.5°–82° C. (recrystallized from dichloromethane-n-hexane)

$^1$H-NMR (CDCl$_3$) δ: 1.63–2.05 (6H,m), 2.19 (2H,m), 2.49 (2H,t), 2.77 (2H,m), 2.94 (3H,s), 3.46 (1H,m), 4.08 (2H,t), 5.57 (1H,s), 6.89–7.41 (11H,m), 7.51 (1H,dd)

EXAMPLE 42

Preparation of 4-di(2-thienyl)methoxy-1-[3-(2-methanesulfonylaminophenoxy)propyl]piperidine

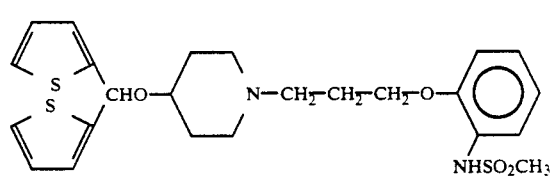

(a) The procedure of Example 36 (a) was repeated except for using di(2-thienyl)methyl chloride and 4-hydroxy-1-[3-(2-nitrophenoxy)propyl]piperidine instead of phenyl-2-thienylmethyl chloride and 4-hydroxy-1-[3-(2-nitrophenoxy)propyl]piperidine to give oily 4-di(2-thienyl)methoxy-1-[3-(2-nitrophenoxy)propyl]piperidine.

$^1$H-NMR (CDCl$_3$) δ: 1.62–1.83 (2H,m), 1.88 (2H,m), 2.01 (2H,quint), 2.22 (2H,m), 2.55 (2H,t), 2.78 (2H,m), 3.58 (1H,m) 4.17 (2H,t), 5.98 (1H,s), 6.83–7.57 (9H,m), 7.81 (1H,dd)

(b) The procedure of Example 1 (b) was repeated except for using the nitro compound obtained in (a) instead of 4-diphenylmethoxy-1-[3-(2-nitrophenoxy)-propyl]piperidine to give 4-di(2-thienyl)methoxy-1-[3-(2-aminophenoxy)propyl]piperidine.

$^1$H-NMR (CDCl$_3$) δ: 1.67–1.84 (2H,m), 1.85–2.09 (4H,m), 2.28 (2H,m), 2.56 (2H,t), 2.79 (2H,m), 3.60 (1H,m), 3.83 (2H,br s) 4.03 (2H,t), 5.97 (1H,s) 6.63–7.00 (8H,m) 7.28 (2H,dd)

(c) The procedure of Example 1 (c) was repeated except for using the amino compound obtained in (b) instead of 4-diphenylmethoxy-1-[3-(2-aminophenoxy)-propyl]piperidine, and the crude product thus obtained was eluted with ethyl acetate-ethanol-dichloromethane (5:1:3) by silica gel column chromatography to give the desired compound.

$^1$H-NMR (CDCl$_3$) δ: 1.68–2.10 (6H,m), 2.32 (2H,m), 2.55 (2H,t), 2.78 (2H,m), 2.95 (3H,s), 3.62 (1H,m), 4.10 (2H,t), 5.97 (1H,s), 6.86–7.35 (9H,m), 7.52 (1H,dd)

EXAMPLE 43

Preparation of 4-[(2-thienyl)-3-thienylmethoxy]-1-[3-(2-methanesulfonylaminophenoxy)propyl]piperidine

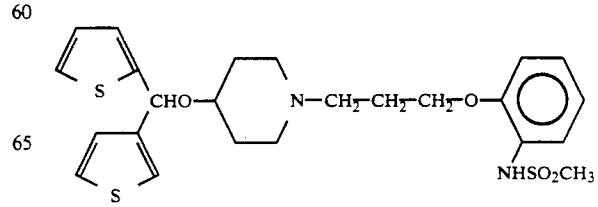

(a) Into 50 ml of 1,2-dichloroethane were dissolved 4.29 g of (2-thienyl)-3-thienylmethyl chloride, 6.72 g of 4-hydroxy-1-[3-(2-nitrophenoxy)propyl]piperidine and 3.88 g of N,N-diisopropylethylamine, and the resultant solution was heated under reflux with stirring for 48 hours.

After cooling, the reaction solution was washed with water, and the solvent was removed under reduced pressure. The residue was eluted with ethyl acetate-ethanol-dichloromethane (1:1:1) by silica gel column chromatography to give 5.51 g of 4-[(2-thienyl)-3-thienylmethoxy]-1-[3-(2-nitrophenoxy)propyl]piperidine hydrochloride.

$^1$H-NMR (CDCl$_3$) δ: 1.96 (2H,m), 2.18-2.48 (4H,m), 2.97-3.23 (6H,m), 3.81 (1H,m) 4.26 (2H,t), 5.78 (1H,s) 6.82-7.60 (9H,m), 7.84 (1H,d)

The hydrochloride obtained in the above was treated with 5% aqueous sodium carbonate to give oily 4-[(2-thienyl)-3-thienylmethoxy]-1-[3-(2-nitrophenoxy)-propyl]piperidine.

$^1$H-NMR (CDCl$_3$) δ: 1.60-1.80 (2H,m), 1.81-2.28 (6H,m), 2.53 (2H,t), 2.77 (2H,m), 3.51 (1H,m), 4.16 (2H,t), 5.81 (1H,s), 6.83-7.56 (9H,m), 7.81 (1H,dd)

(b) The procedure of Example 1 (b) was repeated except for using the nitro compound obtained in (a) instead of 4-diphenylmethoxy-1-[3-(2-nitrophenoxy)-propyl]piperidine to give 4-[(2-thienyl)-3-thienylmethoxy]-1-[3-(2-aminophenoxy)propyl]piperidine.

(c) The procedure of Example 1 (c) was repeated except for using the amino compound obtained in (b) instead of 4-diphenylmethoxy-1-[3-(2-aminophenoxy)-propyl]piperidine to give the desired compound.

$^1$H-NMR (CDCl$_3$) δ: 1.65-2.16 (6H,m), 2.20-2.48 (2H,m), 2.60 (2H,m), 2.81 (2H,m), 2.97 (3H,s), 3.59 (1H,m), 4.11 (2H,t), 5.80 (1H,s), 6.80-7.33 (9H,m), 7.51 (1H,dd)

EXAMPLE 44

Preparation of 4-di(3-thienyl)methoxy-1-[3-(2-methanesulfonylaminophenoxy)propyl]piperidine

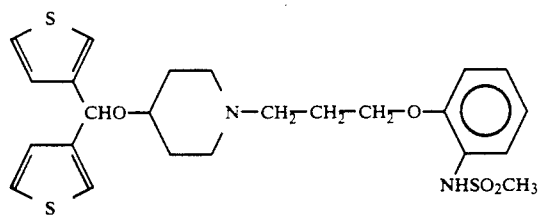

(a) The procedure of Example 36 (a) was repeated except for using di(3-thienyl)methyl chloride and 4-hydroxy-1-[3-(2-nitrophenoxy)propyl]piperidine instead of phenyl-2-thienylmethyl chloride and 4-hydroxy-1-[3-(2-nitrophenoxy)propyl]piperidine to give 4-di(3-thienyl)methoxy-1-[3-(2-nitrophenoxy)propyl]piperidine hydrochloride.

The obtained hydrochloride was treated with 5% aqueous sodium carbonate to give oily 4-di(3-thienyl)-methoxy-1-[3-(2-nitrophenoxy)propyl]piperidine.

$^1$H-NMR (CDCl$_3$) δ: 1.61-1.80 (2H,m), 1.81-1.97 (2H,m), 2.02 (2H,quint), 2.21 (2H,m), 2.56 (2H,t), 2.79 (2H,m), 3.46 (1H,m), 4.17 (2H,t), 5.65 (1H,s), 6.95-7.57 (9H,m), 7.82 (1H,dd)

(b) The procedure of Example 1 (b) was repeated except for using the hydrochloride of the nitro compound obtained in (a) instead of 4-diphenylmethoxy-1-[3-(2-nitrophenoxy)propyl]piperidine to give 4-di(3-thienyl)methoxy-1-[3-(2-aminophenoxy)propyl]piperidine hydrochloride.

m.p.: 179.5°-180° C. (recrystallized from ethanol-n-hexane)

$^1$H-NMR (CDCl$_3$) δ: 1.95 (2H,br d), 2.35-2.55 (4H,m), 3.09 (2H,br t), 3.28 (2H,m), 3.48 (2H,br d), 3.87 (1H,m), 4.11 (2H,t), 5.58 (1H,s), 6.68-7.35 (10H,m)

The hydrochloride obtained in the above was treated with 5% aqueous sodium carbonate to give 4-di(3-thienyl)methoxy-1-[3-2-aminophenoxy)propyl]piperdine.

m.p.: 80°-82° C. (recrystallized from ethyl acetate-n-hexane)

$^1$H-NMR (CDCl$_3$) δ:1.77 (2H,m), 1.87-2.18 (4H,m), 2.37 (2H,m), 2.64 (2H,t), 2.84 (2H,m), 3.52 (1H,m), 3.80 (2H,br s), 4.03 (2H,t), 5.64 (1H,s) 6.62-7.35 (10H,m)

(c) The procedure of Example 1 (c) was repeated except for using the amino compound obtained in (b) instead of 4-diphenylmethoxy-1-[3-(2-aminophenoxy)-propyl]piperidine to give the hydrochloride of the desired compound.

m.p.: 188.5°-190.5° C. (recrystallized from ethanol-n-hexane)

$^1$H-NMR (CDCl$_3$) δ:1.84-2.06 (2H,m), 2.15-2.52 (4H,m), 3.03 (3H,s), 3.05-3.38 (6H,m), 3.76 (1H,m), 4.13 (2H,t), 5.59 (1H,s), 6.82-7.51 (10H,m)

The hydrochloride obtained in the above was treated with 5% aqueous sodium carbonate to give the desired compound.

m.p.: 92°-94° C. (recrystallized from ethyl acetate-n-hexane)

$^1$H-NMR (CDCl$_3$) δ:1.63-1.80 (2H,m), 1.83-2.07 (4H,m), 2.22 (2H,m), 2.51 (2H,t), 2.77 (2H,m), 2.95 (3H,s), 3.48 (1H,m), 4.09 (2H,t), 5.65 (1H,s), 6.90-7.33 (9H,m), 7.52 (1H,dd)

The procedure of Example 3 was repeated except for using the desired compound obtained in the above and fumaric acid instead of 4-diphenylmethoxy-1-[3-(2-methanesulfonylaminophenoxy)propyl]piperidine and fumaric acid to give the fumarate of the desired compound.

m.p.: 118.5°-120.5° C. (recrystallized from dichloromethane-ethyl acetate)

The procedure of Example 3 was repeated except for using the desired compound obtained in the above and oxalic acid instead of 4-diphenylmethoxy-1-[3-(2-methanesulfonylaminophenoxy)propyl]piperidine and fumaric acid to give the oxalate of the desired compound.

m.p.: 168.5°-171° C. (recrystallized from dichloromethane-ethanol)

EXAMPLE 45

Preparation of 4-di(3-thienyl)methoxy-1-[3-(2-methanesulfonylamino-phenoxy)-1-methylpropyl]piperidine

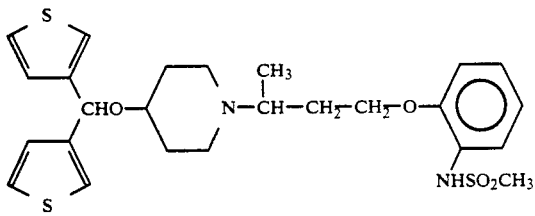

(a) The procedure of Example 36 (a) was repeated except for using di(3-thienyl)methyl chloride and 4-hydroxy-1-[1-methyl-3-(2-nitrophenoxy)propyl]piperidine instead of phenyl-2-thienylmethyl chloride and 4-hydroxy-1-[3-(2-nitrophenoxy)propyl]piperidine to give oily 4-di(3-thienyl)methoxy-1-[1-methyl-3-(2-nitrophenoxy)propyl]piperidine (b) The procedure of Example 1 (b) was repeated except for using the nitro compound obtained in (a) instead of 4-diphenylmethoxy-1-[3-(2-nitrophenoxy)-propyl]piperidine to give 4-di(3-thienyl)methoxy-1-[3-(2-aminophenoxy)-1-methylpropyl]piperidine.

(c) The procedure of Example 1 (c) was repeated except for using the amino compound obtained in (b) instead of 4-diphenylmethoxy-1-[3-(2-aminophenoxy)-propyl]piperidine to give the desired compound.

$^1$H-NMR (CDCl$_3$) δ:1.02 (3H,d), 1.56–2.13 (6H,m), 2.25 (1H,m), 2.45 (1H,br t), 2.62–2.98 (3H,m), 2.95 (3H,s), 3.44 (1H,m), 4.00–4.21 (2H,m), 5.65 (1H,s), 6.89–7.33 (9H,m), 7.51 (1H,dd)

EXAMPLE 46

Preparation of 4-di(3-thienyl)methoxy-1-[4-(2-methanesulfonylamino-phenoxy)-2(E)-butenyl]piperidine

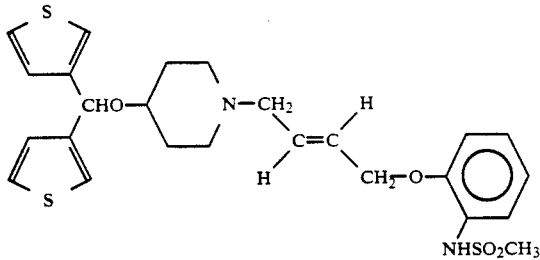

(a) The procedure of Example 39 (a) was repeated except for using di(3-thienyl)methyl chloride and 4-hydroxy-1-[4-(2-nitrophenoxy)-2(E)-butenyl]piperidine instead of phenyl-2-thienylmethyl chloride and 4-hydroxy-1-[4-(2-nitrophenoxy)-2(E)-butenyl]piperidine to give oily 4-di(3-thienyl)methoxy-1-[4-(2-nitrophenoxy)-2(E)-butenyl]piperidine.

$^1$H-NMR (CDCl$_3$) δ:1.59–1.79 (2H,m), 1.79–1.96 (2H,m), 2.14 (2H,m), 2.72 (2H,m), 3.01 (2H,d), 3.44 (1H,m), 4.67 (2H,d), 5.64 (1H,s), 5.74–6.02 (2H,m), 6.92–7.57 (9H,m), 7.82 (1H,dd)

(b) The procedure of Example 1 (b) was repeated except for using the nitro compound obtained in (a) instead of 4-diphenylmethoxy-1-[3-(2-nitrophenoxy)-propyl]piperidine to give 4-di(3-thienyl)methoxy-1-[4-(2-aminophenoxy)-2(E)-butenyl]piperidine.

$^1$H-NMR (CDCl$_3$) δ:1.58–2.00 (4H,m), 2.17 (2H,m), 2.71 (2H,m), 3.00 (2H,d), 3.46 (1H,m), 4.52 (2H,d), 5.63 (1H,s), 5.72–5.97 (2H,m), 6.72–7.34 (10H,m)

(c) The procedure of Example 1 (c) was repeated except for using the amino compound obtained in (b) instead of 4-diphenylmethoxy-1-[3-(2-aminophenoxy)-propyl]piperidine to give the desired compound.

$^1$H-NMR (CDCl$_3$) δ:1.63–1.98 (4H,m), 2.23 (2H,m), 2.75 (2H,m), 2.95 (3H,s), 3.06 (2H,d), 3.48 (1H,m), 4.58 (2H,d), 5.64 (1H,s), 5.74–5.99 (2H,m), 6.83–7.33 (9H,m) 7.52 (1H,dd)

EXAMPLE 47

Preparation of 4-di(3-thienyl)methoxy-1-[4-(2-methanesulfonylamino-phenoxy)-2(Z)-butenyl]piperidine

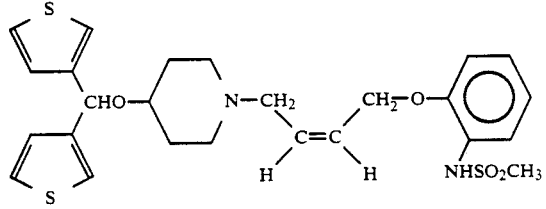

(a) The procedure of Example 39 (a) was repeated except for using di(3-thienyl)methyl chloride and 4-hydroxy-1-[4-(2-nitrophenoxy)-2(Z)-butenyl]piperidine instead of phenyl-2-thienylmethyl chloride and 4-hydroxy-1-[4-(2-nitrophenoxy)-2(E)-butenyl]piperidine to give oily 4-di(3-thienyl)methoxy-1-[4-(2-nitrophenoxy)-2(Z)-butenyl]piperidine.

$^1$H-NMR (CDCl$_3$) δ:1.60–1.98 (4H,m), 2.24 (2H,m), 2.76 (2H,m), 3.11 (2H,br d), 3.48 (1H,m), 4.76 (2H,d), 5.64 (1H,s), 5.71–5.93 (2H,m), 6.92–7.57 (9H,m), 7.82 (1H,dd)

(b) The procedure of Example 1 (b) was repeated except for using the nitro compound obtained in (a) instead of 4-diphenylmethoxy-1-[3-(2-nitrophenoxy)-propyl]piperidine to give 4-di(3-thienyl)methoxy-1-[4-(2-aminophenoxy)-2(Z)-butenyl]piperidine.

(c) The procedure of Example 1 (c) was repeated except for using the amino compound obtained in (b) instead of 4-diphenylmethoxy-1-[3-(2-aminophenoxy)-propyl]piperidine to give the hydrochloride of the desired compound.

$^1$H-NMR (CDCl$_3$) δ:1.73–1.93 (2H,m), 2.09 (2H,m), 2.64 (2H,m), 2.89 (2H,m), 2.98 (3H,s), 3.32 (2H,d), 3.62 (1H,m), 4.70 (2H,d), 5.62 (1H,s), 5.82–6.04 (2H,m), 6.85–7.34 (9H,m), 7.51 (1H,dd)

The hydrochloride obtained in the above was treated with 5% aqueous sodium carbonate to give the desired compound.

$^1$H-NMR (CDCl$_3$) δ:1.65–1.82 (2H,m), 1.83–1.97 (2H,m), 2.24 (2H,m), 2.75 (2H,m), 2.94 (3H,s), 3.08 (2H,br d), 3.49 (1H,m), 4.66 (2H,d), 5.64 (1H,s), 5.82 (2H,m) 6.87–7.33 (9H,m), 7.53 (1H,dd)

EXAMPLE 48

Preparation of
4-[(3-pyridyl)-2-thienylmethoxy]-1-[3-(2-methanesulfonylaminophenoxy)propyl]piperidine

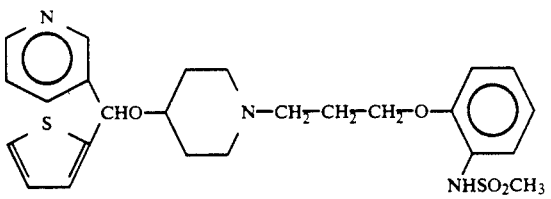

(a) The procedure of Example 24 (a) was repeated except for using 4-[(3-pyridyl)-2-thienylmethoxy]piperidine and 1-chloro-3-(2-nitrophenoxy)propane instead of 4-[(2-chlorophenyl)-phenylmethoxy]piperidine and 1-chloro-3-(2-nitrophenoxy)propane to give oily 4-[(3-pyridyl)-2-thienylmethoxy]-1-[3-(2-nitrophenoxy)propyl]piperidine.

$^1$H-NMR (CDCl$_3$) δ:1.72 (2H,m), 1.82–2.11 (4H,m), 2.30 (2H,m), 2.60 (2H,t), 2.78 (2H,m), 3.51 (1H,m), 4.17 (2H,t), 5.78 (1H,s), 6.77–7.34 (6H,m), 7.50 (1H,td) 7.72 (1H,br d), 7.82 (1H,dd), 8.55 (1H,m), 8.61 (1H,br s)

(b) The procedure of Example 1 (b) was repeated except for using the nitro compound obtained in (a) instead of 4-diphenylmethoxy-1-[3-(2-nitrophenoxy)propyl]piperidine to give 4-[(3-pyridyl)-2-thienylmethoxy]-1-[3-(2-aminophenoxy)propyl]piperidine.

(c) The procedure of Example 1 (c) was repeated except for using the amino compound obtained in (b) instead of 4-diphenylmethoxy-1-[3-(2-aminophenoxy)propyl]piperidine to give the desired compound.

$^1$H-NMR (CDCl$_3$) δ:1.67–1.87 (2H,m), 1.88–2.10 (4H,m), 2.34 (2H,m), 2.57 (2H,t), 2.70–2.89 (2H,m), 2.96 (3H,s), 3.58 (1H,m), 4.09 (2H,t), 5.77 (1H,s), 6.80–7.34 (7H,m), 7.51 (1H,dd), 7.73 (1H,dt), 8.55 (1H,d), 8.65 (1H,d)

EXAMPLE 49

Preparation of
4-[(3-pyridyl)-3-thienylmethoxy]-1-[3-(2-methanesulfonylaminophenoxy)propyl]piperidine

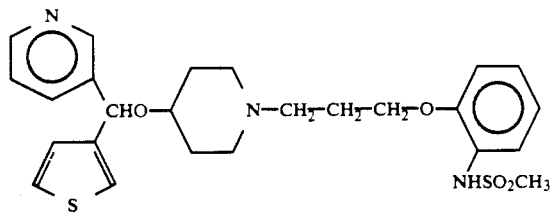

(a) The procedure of Example 24 (a) was repeated except for using 4-[(3-pyridyl)-3-thienylmethoxy]piperidine and 1-chloro-3-(2-nitrophenoxy)propane instead of 4-[(2-chlorophenyl)-phenylmethoxy]piperidine and 1-chloro-3-(2-nitrophenoxy)propane to give oily 4-[(3-pyridyl)-3-thienylmethoxy]-1-[3-(2-nitrophenoxy)propyl]piperidine.

$^1$H-NMR (CDCl$_3$) δ:1.72 (2H,m), 1.90 (2H,m), 2.02 (2H,quint), 2.22 (2H,m), 2.56 (2H,t), 2.79 (2H,m), 3.46 (1H,m), 4.16 (2H,t), 5.62 (1H,s), 6.93–7.35 (6H,m), 7.51 (1H,td) 7.68 (1H,dt), 7.81 (1H,dd), 8.52 (1H,dd), 8.61 (1H,d)

(b) The procedure of Example 1 (b) was repeated except for using the nitro compound obtained in (a) instead of 4-diphenylmethoxy-1-[3-(2-nitrophenoxy)propyl]piperidine to give 4-[(3-pyridyl)-3-thienylmethoxy]-1-[3-(2-aminophenoxy)propyl]piperidine.

$^1$H-NMR (CDCl$_3$) δ:1.76 (2H,m), 1.84–2.11 (4H,m), 2.28 (2H,m), 2.58 (2H,t), 2.80 (2H,m), 3.49 (1H,m), 4.03 (2H,t), 5.61 (1H,s), 6.63–6.83 (4H,m), 6.97 (1H, dd), 7.14 (1H,d), 7.22–7.33 (2H,m), 7.67 (1H,dt), 8.53 (1H,d), 8.61 (1H,s)

(c) The procedure of Example 1 (c) was repeated except for using the amino compound obtained in (b) instead of 4-diphenylmethoxy-1-[3-(2-aminophenoxy)propyl]piperidine to give the desired compound.

$^1$H-NMR (CDCl$_3$) δ:1.76 (2H,m), 1.85–2.12 (4H,m), 2.30 (2H,m), 2.56 (2H,t), 2.79 (2H,m), 2.96 (3H,s), 3.50 (1H,m), 4.09 (2H,t), 5.61 (1H,s), 6.85–7.35 (7H,m), 7.51 (1H,dd), 7.66 (1H,d), 8.54 (1H,br s), 8.62 (1H,br s)

EXAMPLE 50

Preparation of
4-di(3-thienyl)methoxy-1-[3-(2-N-methyl-N-methanesulfonylaminophenoxy)propyl]piperidine

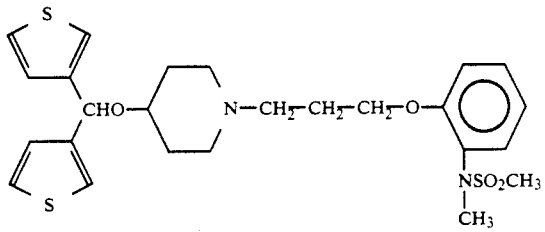

The procedure of Example 8 was repeated except for using 4-di(3-thienyl)methoxy-1-[3-(2-methanesulfonylaminophenoxy)propyl]piperidine obtained in Example 44 (c) and methyl iodide instead of 4-diphenylmethoxy-1-[3-(2-methanesulfonylaminophenoxy)propyl]piperidine and methyl iodide to give the desired compound.

$^1$H-NMR (CDCl$_3$) δ:1.67–1.84 (2H,m), 1.90–2.15 (4H,m), 2.37 (2H,m), 2.65 (2H,t), 2.85 (2H,m), 2.95 (3H,s), 3.26 (3H,s), 3.53 (1H,m), 4.09 (2H,t), 5.64 (1H,s), 6.91–7.37 (10H,m)

EXAMPLE 51

Preparation of
4-di(3-thienyl)methoxy-1-[3-(2-methanesulfonylamino-4-methylphenoxy)propyl]piperidine

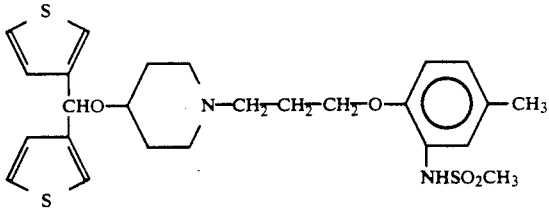

(a) The procedure of Example 36 (a) was repeated except for using di(3-thienyl)methyl chloride and 4-hydroxy-1-[3-(4-methyl-2-nitrophenoxy)propyl]piperidine instead of phenyl-2-thienylmethyl chloride and 4-hydroxy-1-[3-(2-nitrophenoxy)propyl]piperidine to give oily 4-di(3-thienyl)methoxy-1-[3-(4-methyl-2-nitrophenoxy)propyl]piperidine.

¹H-NMR (CDCl₃) δ:1.60-1.77 (2H,m), 1.79-2.05 (4H,m), 2.14 (2H,m), 2.33 (3H,s), 2.51 (2H,t), 2.76 (2H,m), 3.44 (1H,m), 4.12 (2H,t), 5.65 (1H,s), 6.92-7.34 (8H,m), 7.62 (1H,m)

(b) The procedure of Example 1 (b) was repeated except for using the nitro comound obtained in (a) instead of 4-diphenylmethoxy-1-[3-(2-nitrophenoxy)propyl]piperidine to give 4-di(3-thienyl)methoxy-1-[3-(2-amino-4-methylphenoxy)propyl]piperidine.

¹H-NMR (CDCl₃) δ:1.61-1.80 (2H,m), 1.81-2.05 (4H,m), 2.16 (2H,m), 2.21 (3H,s), 2.51 (2H,t), 2.77 (2H,m), 3.46 (1H,m), 3.77 (2H,br s), 3.99 (2H,t), 5.65 (1H,s), 6.45-6.57 (2H,m), 6.68 (1H,d), 6.99-7.32 (6H,m)

(c) The procedure of Example 1 (c) was repeated except for using the amino compound obtained in (b) instead of 4-diphenylmethoxy-1-[3-(2-aminophenoxy)propyl]piperidine to give the desired compound.

¹H-NMR (CDCl₃) δ:1.63-1.79 (2H,m), 1.81-2.03 (4H,m), 2.17 (2H,m), 2.29 (3H,s), 2.48 (2H,t), 2.75 (2H,m), 2.94 (3H,s), 3.46 (1H,m), 4.05 (2H,t), 5.65 (1H,s), 6.78-7.36 (9H,m)

EXAMPLE 52

Preparation of 4-di(3-thienyl)methoxy-1-[3-(2-methanesulfonylaminophenoxy)-2-methylpropyl]piperidine

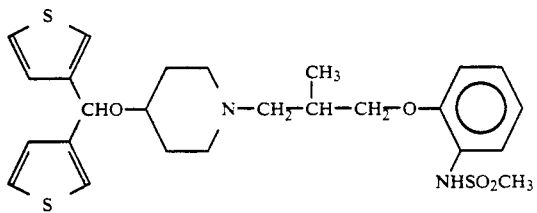

(a) The procedure of Example 36 (a) was repeated except for using di(3-thienyl)methyl chloride and 4-hydroxy-1-[2-methyl-3-(2-nitrophenoxy)propyl]piperidine instead of phenyl-2-thienylmethyl chloride and 4-hydroxy-1-[3-(2-nitrophenoxy)propyl]piperidine to give oily 4-di(3-thienyl)methoxy-1-[2-methyl-3-(2-nitrophenoxy)propyl]piperidine.

¹H-NMR (CDCl₃) δ:1.06 (3H,d), 1.55-1.75 (2H,m), 1.77-1.92 (2H,m), 1.94-2.26 (4H,m), 2.30-2.46 (1H,m), 2.67 (1H,m), 2.80 (1H,m), 3.41 (1H,m), 3.89-3.99 (1H,m), 4.08-4.18 (1H,m), 5.65 (1H,s), 6.92-7.55 (9H,m), 7.82 (1H,dd)

(b) The procedure of Example 1 (b) was repeated except for using the nitro compound obtained in (a) instead of 4-diphenylmethoxy-1-[3-(2-nitrophenoxy)propyl]piperidine to give 4-di(3-thienyl)methoxy-1-[3-(2-aminophenoxy)-2-methylpropyl]piperidine.

¹H-NMR (CDCl₃) δ:1.05 (3H,d), 1.55-1.75 (2H,m), 1.77-1.92 (2H,m), 1.98-2.24 (4H,m), 2.31-2.45 (1H,m), 2.61-2.83 (2H,m), 3.43 (1H,m), 3.68-3.91 (3H,m), 3.92-4.01 (1H,m), 5.65 (1H,s), 6.64-7.31 (10H,m)

(c) The procedure of Example 1 (c) was repeated except for using the amino compound obtained in (b) instead of 4-diphenylmethoxy-1-[3-(2-aminophenoxy)propyl]piperidine to give the desired compound.

¹H-NMR (CDCl₃) δ:1.02 (3H,d), 1.59-1.78 (2H,m), 1.84 (2H,m), 2.03-2.28 (4H,m), 2.29-2.43 (1H,m), 2.67 (1H,m), 2.78 (1H,m), 2.94 (3H,s), 3.45 (1H,m), 3.80-3.90 (1H,m), 3.99-4.08 (1H,m), 5.65 (1H,s), 6.90-7.31 (9H,m), 7.52 (1H,dd)

That the piperidine derivative of the present invention has the excellent inhibitory activity of histamine release and antihistaminic activity and that the piperidine derivative of the present invention is therapeutically effective for ischemic heart disease such as stenocardia or myocardial infarction are illustrated with reference to following Test Examples.

TEST EXAMPLE 1

Inhibition of anaphylactic histamine release

Hartley male guinea pigs weighing about 450 g which were passively sensitized with an anti-DNP-egg albumin guinea pig serum were killed with a thiopentbarbital anesthetia. Their lungs were perfused by way of the pulmonary artery with a Tyrode's solution. The lungs were removed and fragmented. A definite weight of 100 mg lung fragments, which was distributed into individual tubes and suspended in 1 ml of Tyrode's solution, was challenged with the antigen (DNP-egg albumin, final concentration: 0.3 μg/ml) at 37° C. for 15 min. The test compounds obtained in Example, which were dissolved or suspended in Tyrode's solution, were added 10 min before antigen challenge. The reaction was stopped by immersing in ice cold water, and then centrifuged. The amount of histamine in the supernatant fluid was measured by using fluoremetric method according to Shore et al.

From the results described above, an inhibition ratio was calculated as follows and a 25%-inhibitory concentration was obtained:

$$\text{Inhibition ratio} = \left(1 - \frac{A - B}{C - B}\right) \times 100$$

A: amount of histamine released by the antigen stimulation in the presence of a compound of the present invention
B: amount of histamine released spontaneously
C: amount of histamine released by the antigen stimulation.

The results are shown in Table 3.

TEST EXAMPLE 2

Antihistaminic activity

Hartley male guinea pigs weighing 500-600 g were used. Isolated tracheal smooth muscle chain strips were prepared by a usual method and suspended in 2 ml organ bath of Tyrode's solution aerated with 95% $O_2$ 5% $CO_2$ at 37° C. Each strip was attached to an isotonic transducer (made by Nihon Koden Kogyo KK) with a load of 0.5 g. After almost constant contraction, histamine was added cumulatively, until maximum constriction was obtained. The constriction of tracheal strip was recorded by Servocorder (made by Giraphtec KK). The strip was washed with Tyrode's solution and allowed to stabilize. Test compound was to the bath 5 min prior to the addition of histamine and the response curve to the histamine was repeated. The $pA_2$ values were calculated using the techniques of Van Rossum.

The results are shown in Table 3.

TABLE 3

| Test Compound | Test Example 1 (25%-inhibitory conc.) | Test Example 2 ($pA_2$) |
|---|---|---|
| Example 1 | $1 \times 10^{-6}$ M | 8.7 |
| Example 34 (fumarate) | $1 \times 10^{-6}$ M | 9.9 |
| Example 36 (fumarate) | $1 \times 10^{-7}$ M | 8.6 |
| Example 37 | $1 \times 10^{-7}$ M | 8.4 |

TABLE 3-continued

| Test Compound | Test Example 1 (25%-inhibitory conc.) | Test Example 2 (pA$_2$) |
|---|---|---|
| Example 40 | 1 × 10$^{-7}$ M | 8.2 |
| Example 44 (fumarate) | 3 × 10$^{-8}$ M | 8.6 |
| Amlexanox* | 3 × 10$^{-5}$ M | — |
| Oxatomide* | 1 × 10$^{-4}$ M | 8.9 |
| Diphenhyldramine hydrochloride* | — | 8.9 |

*Reference drug

In Test Examples 1 and 2, comparative tests were carried out by using as reference drugs, Amlexanox having the inhibitory activity of histamine release and Oxatomide having the inhibitory activity of histamine release and antihistaminic activity and diphenhydramine hydrochloride having antihistaminic activity.

From the results described in Table 3, the compounds of the present invention were confirmed to have both excellent inhibitory activity of anaphylactic histamine release and antihistaminic activity.

TEST EXAMPLE 3

Hearts were isolated from Std; Wistar male rats weighing 200–300 g (9–10 weeks old). The hearts were perfused using Langendorff's apparatus at a flow rate of 8 ml/min. As a perfusate, Krebs-Henseleit-bicarbonate solution (37° C., pH 7.4) containing 11 mM glucose, oxygenated with a mixed gas of 95% O$_2$ and 5% CO$_2$ was used. The heart was preloaded with an initial resting tension of 2.0 g and paced at 200–300 beats min$^{-1}$. After the hearts were allowed to be stable for 30–60 minutes, 0.1 ml of a solution of each test compound in 10% DMSO was added thereto to be a concentration of 0.1, 1.0, 10 or 100 μg of each compound per heart.

Myocardial contractile force was isometrically measured by means of a force-displacement transducer (Type: TB-612T, made by Nihon Kohden Kogyo KK) connected to the apex of the heart through a thread. Coronary perfusion pressure was monitored by an electric manometer (Type: MPU-0.5, made by Nihon Kohden Kogyo KK) connected to a side branch of the aortic cannule.

From these results, change rates were calculated according to the following expression.

$$\text{Change rate (\%)} = \frac{B - A}{A} \times 100$$

A: value before adding a test compound
B: value after adding a test compound
The results are shown in Table 4.

TABLE 4

| Test compound | Concentration (μg/heart) | Perfusion pressure (Δ %) | Contractive force (Δ %) | Heart rate (Δ %) |
|---|---|---|---|---|
| Example 1 | 0.1 | −8.39 ± 3.4 | 2.0 ± 3.6 | 0.7 ± 1.2 |
| | 1 | −24.8 ± 3.0** | 11.9 ± 2.4 | −0.7 ± 1.2 |
| | 10 | −42.9 ± 3.2** | 11.8 ± 2.3 | −0.7 ± 1.2 |
| | 100 | −49.0 ± 4.8** | −25.0 ± 6.8** | −16.6 ± 15.6** |
| Example 33 | 0.1 | −7.0 ± 6.1 | 5.0 ± 4.3 | −1.2 ± 2.1 |
| | 1 | −19.2 ± 2.2** | 13.3 ± 1.9 | −1.9 ± 1.8 |
| | 10 | −39.1 ± 5.4** | 16.0 ± 4.5 | −4.6 ± 4.7 |
| | 100 | −40.1 ± 5.2** | −46.2 ± 13.4** | −17.2 ± 10.1** |
| Example 44 | 0.1 | −6.0 ± 13.7 | 8.8 ± 2.5 | −5.7 ± 1.4 |
| | 1 | −28.9 ± 3.0** | 19.1 ± 5.7** | −3.6 ± 4.1 |
| | 10 | −47.9 ± 4.8** | 16.2 ± 11.3 | −6.3 ± 1.5 |
| | 100 | −55.8 ± 3.5** | −46.3 ± 19.4** | −59.9 ± 11.1** |
| Control drug Diltiazem hydrochloride | 0.1 | −10.3 ± 4.0 | 3.5 ± 6.9 | −2.7 ± 1.8 |
| | 1 | −32.1 ± 6.9** | 7.0 ± 16.1 | −3.5 ± 2.4 |
| | 10 | −47.1 ± 1.4** | −67.1 ± 17.5** | −25.9 ± 30.3** |
| | 100 | −48.8 ± 1.4** | −86.5 ± 7.0** | −71.4 ± 11.9** |
| Control (10% DMSO) | | −7.1 ± 4.6 | 8.8 ± 4.6 | −1.5 ± 2.4 | means value ± S.D., n = 3–4 (n = 30 in control (10% DMSO))
**p <0.01 significant difference from control (10% DMSO)

The compounds obtained in Examples caused lowerings of perfusion pressure at dosages which do not cause changes of contractive force or heart rates in contrast with diltiazem hydrochloride.

While diltiazem hydrochloride caused significant lowerings of contractive force and heart rates at a dosage of 10 μg/heart, the compounds obtained in Examples did not cause any changes at a dosage of 10 μg/heart. Therefore, the compounds of the present invention are recognized to be safe in wider range of dosage.

From the results as described above, the compounds of the present invention were confirmed to be effective for prevention or treatment of ischemic heart disease such as stenocardia or myocardial infarction.

TEST EXAMPLE 4

The LD$_{50}$ of the compounds obtained in Examples 1, 34, 37, 40 and 44 were more than 500 mg/kg when these compounds were given orally to mice weighing 22–27 g (ddY, male, 5 weeks).

Formulation Examples of the compounds of the present invention are illustrated below, but it should be construed that the formulation using the compounds of the present invention are not limited to these Examples.

FORMULATION EXAMPLE 1

Tablets each containing 10 mg of an effective ingredient were prepared according to the formulation described below.

| (component) | (mg) |
|---|---|
| compound obtained in Example 44 (fumarate) | 10 |
| lactose | 30 |
| corn starch | 40 |
| crystalline cellulose | 15 |
| methyl cellulose | 3 |
| magnesium stearate | 2 |

FORMULATION EXAMPLE 2

A component mixture in an amount of 100 mg containing 10 mg of an effective ingredient according to the formulation described below was encapsulated to give a capsule.

| (component) | (mg) |
|---|---|
| compound obtained in Example 44 (fumarate) | 10 |
| lactose | 50 |
| corn starch | 30 |
| crystalline cellulose | 8 |
| magnesium stearate | 2 |

In addition to the ingredients used in the Examples, other ingredients can be used as set forth in the specification to obtain substantially the same results.

What we claim is:

1. A piperidine compound having the formula (I):

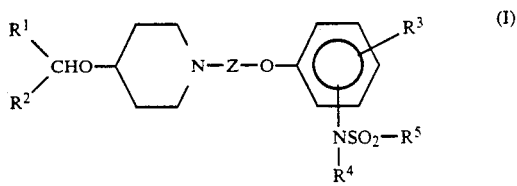

wherein $R^1$ and $R^2$, which may be the same or different from each other, are (i) a phenyl group or a phenyl group substituted by a halogen atom, trifluoromethyl group, a $C_{1-5}$ alkyl group or a $C_{1-5}$ alkoxyl group, (ii) a $C_{3-7}$ cycloalkyl group, (iii) pyridyl group or (iv) thienyl group, $R^3$ is (i) hydrogen atom, (ii) a halogen atom, (iii) a $C_{1-4}$ alkyl group or (iv) a $C_{1-4}$ alkoxyl group, $R^4$ is (i) hydrogen atom or (ii) a $C_{1-4}$ alkyl group. $R^5$ is (i) a $C_{1-5}$ alkyl group or a $C_{1-5}$ alkyl group substituted by a halogen atom, (ii) phenyl group or (iii) thienyl group and Z is (i) a $C_{1-6}$ alkylene group, (ii) a $C_{2-6}$ alkenylene group or (iii) a $C_{3-6}$ alkynylene group or a pharmacologically acceptable salt thereof.

2. A piperidine compound having the formula (II):

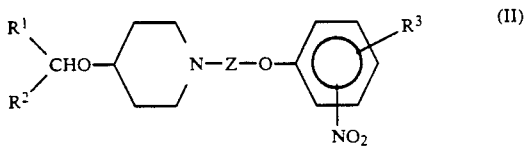

wherein $R^1$ and $R^2$, which may be the same or different from each other, are (i) a phenyl group or a phenyl group substituted by a halogen atom, trifluoromethyl group, a $C_{1-5}$ alkyl group or a $C_{1-5}$ alkoxyl group, (ii) a $C_{3-7}$ cycloalkyl group, (iii) pyridyl group or (iv) thienyl group, $R^3$ is (i) hydrogen atom, (ii) a halogen atom, (iii) a $C_{1-4}$ alkyl group or (iv) a $C_{1-4}$ alkoxyl group, and Z is (i) a $C_{1-6}$ alkylene group, (ii) a $C_{2-6}$ alkenylene group or (iii) a $C_{3-6}$ alkynylene group.

3. A piperidine compound having the formula (III):

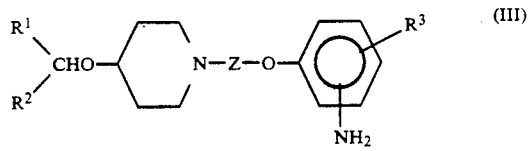

wherein $R^1$ and $R^2$, which may be the same or different from each other, are (i) a phenyl group or a phenyl group substituted by a halogen atom, trifluoromethyl group, a $C_{1-5}$ alkyl group or a $C_{1-5}$ alkoxyl group, (ii) a $C_{3-7}$ cycloalkyl group, (iii) pyridyl group or (iv) thienyl group, $R^3$ is (1) hydrogen atom, (ii) a halogen atom, (iii) a $C_{1-4}$ alkyl group or (iv) a $C_{1-4}$ alkoxyl group, and Z is (i) a $C_{1-6}$ alkylene group, (ii) a $C_{2-6}$ alkenylene group or (iii) a $C_{3-6}$ alkynylene group.

4. A piperidine compound of claim 1, which is 4-[(4-chlorophenyl)-2-pyridylmethoxy]-1-[3-(2-methanesulfonylaminophenoxy)propyl]piperidine or a pharmacologically acceptable salt thereof.

5. A piperidine compound of claim 1, which is 4-(phenyl-2-thienylmethoxy)-1-[3-(2-methanesulfonylaminophenoxy)propyl]piperidine or a pharmacologically acceptable salt thereof.

6. A piperidine compound of claim 1, which is 4-di(3-thienyl)methoxy-1-[3-(2-methanesulfonylaminophenoxy)propyl]piperidine or a pharmacologically acceptable salt thereof.

7. A piperidine compound of claim 1, which is 4-diphenylmethoxy-1-[3-(2-methanesulfonylaminophenoxy)propyl]piperidine or a pharmacologically acceptable salt thereof.

8. A piperidine compound of claim 1, which is 4-di(3-thienyl)methoxy-1-[4-(2-methanesulfonylaminophenoxy)-2(Z)-butenyl]piperidine or a pharmacologically acceptable salt thereof.

9. An anti-allergic composition agent comprising as an effective amount the piperidine compound or a pharmacologically acceptable salt thereof of claim 1 in combination with a pharmaceutically acceptable carrier.

10. A therapeutic composition for ischemic heart disease comprising as an effective amount the piperidine compound or a pharmacologically acceptable salt thereof of claim 1 in combination with a pharmaceutically acceptable carrier.

* * * * *